US009988649B2

(12) United States Patent
De Bont et al.

(10) Patent No.: US 9,988,649 B2
(45) Date of Patent: Jun. 5, 2018

(54) YEAST STRAINS ENGINEERED TO PRODUCE ETHANOL FROM ACETIC ACID AND GLYCEROL

(71) Applicant: DSM IP Assets B.V., Heerlen (NL)

(72) Inventors: Johannes Adrianus Maria De Bont, Echt (NL); Aloysius Wilhelmus Rudolphus Hubertus Teunissen, Echt (NL); Paul Klaassen, Echt (NL); Wouter Willem Antonius Hartman, Echt (NL); Shimaira Van Beusekom, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days. days.

(21) Appl. No.: 14/361,782

(22) PCT Filed: Nov. 26, 2012

(86) PCT No.: PCT/NL2012/050841

§ 371 (c)(1),
(2) Date: May 30, 2014

(87) PCT Pub. No.: WO2013/081456

PCT Pub. Date: Jun. 6, 2013

(65) Prior Publication Data

US 2015/0176032 A1 Jun. 25, 2015

Related U.S. Application Data

(60) Provisional application No. 61/564,932, filed on Nov. 30, 2011.

(30) Foreign Application Priority Data

Nov. 30, 2011 (EP) .................................... 11191333

(51) Int. Cl.

| | |
|---|---|
| ***C12N 1/00*** | (2006.01) |
| ***C12P 7/06*** | (2006.01) |
| ***C07H 21/04*** | (2006.01) |
| ***C12N 1/22*** | (2006.01) |
| ***C12N 9/04*** | (2006.01) |
| ***C12N 9/02*** | (2006.01) |
| ***C12P 7/08*** | (2006.01) |
| ***C12P 7/10*** | (2006.01) |

(52) U.S. Cl.

CPC .................. *C12P 7/06* (2013.01); *C12N 1/22* (2013.01); *C12N 9/0006* (2013.01); *C12N 9/0008* (2013.01); *C12P 7/08* (2013.01); *C12P 7/10* (2013.01); *C12Y 101/01006* (2013.01); *C12Y 102/0101* (2013.01); *C12Y 102/01* (2013.01); *Y02E 50/16* (2013.01); *Y02E 50/17* (2013.01)

(58) Field of Classification Search

None

See application file for complete search history.

(56) References Cited

FOREIGN PATENT DOCUMENTS

| | | | |
|---|---|---|---|
| WO | 2011140386 | A2 | 11/2011 |
| WO | 2011149353 | A1 | 12/2011 |
| WO | 2011153516 | A2 | 12/2011 |
| WO | 2012067510 | A1 | 5/2012 |

OTHER PUBLICATIONS

Whisstock et al. Quaterly Reviews of Biophysics, 2003, "Prediction of protein function from protein sequence and structure", 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36)11643-50.*

Guadalupe Medina V. et al. "Elimination of Glycerol Production in Anaerobic Cultures of a *Saccharomyces cerevisiae* Strain Engineered to Use Acetic Acid as an Electron Acceptor", Applied and Environmental Microbiology, 76:90-195 (Jan. 1, 2010).

Liang Zhang et al. "Improving the ethanol yield by reducing glycerol formation using cofactor regulation in *Saaccharomyces cerevisiae*", Biotechnology Letters, 33:375-1380 (Mar. 13, 2011).

Yu Kyung Ok et al. "Engineering of glycerol utilization pathway for ethanol production by *Saccharomyces cerevisiae*", Bioresource Technology, 101:4157-4161 (Jun. 1, 2010).

Bjorn Holst et al. "GUP1 and its close homologue GUP2, encoding multimembrane-spanning proteins involved in active glycerol uptake in *Saccharomyces cerevisiae*", Molecular Microbiology, 37:108-124, (Jul. 1, 2000).

Luyten Kattie et al. "Fps1, a yeast member of the MIP family of channel proteins, is a facilitator for glycerol uptake and efflux and is inactive under osmotic stress", EMBO Journal 14:1360-1371 (Jan. 1, 1995).

Albertyn J. et al. "Gpd1, which encodes glycerol 3-phosphate dehydrogenase, is essential for growth under osmotic stress in *Saccharomyces cerevisiae*. and its expression is regulated by the high-osmolarity glycerol response pathway", Molecular and Cellular Biology 14:4135-4144 (Jun. 1, 1994).

(Continued)

*Primary Examiner* — Iqbal H Chowdhury

(74) *Attorney, Agent, or Firm* — McBee Moore Woodward & Vanik IP, LLC; Susan McBee; Chester Moore

(57) ABSTRACT

The present invention relates to processes for producing ethanol from lignocellulosic hydrolysates comprising hexoses, pentoses and acetic acid, whereby genetically modified yeast cells are use that comprise an exogenous gene encoding an acetaldehyde dehydrogenase and a bacterial gene encoding an enzyme with $NAD^+$-linked glycerol dehydrogenase activity. The process is further characterized in that glycerol is present in or fed into the culture medium, whereby the modified yeast cell ferments the hexoses, pentoses, acetic acid and glycerol to ethanol. The invention further relates to yeast cells for use in such processes. The yeast cells advantageously comprise genetic modifications that improve glycerol utilization such as modifications that increase one or more of dihydroxyacetone kinase activity and transport of glycerol into the cell. The yeast cell further preferably comprises a functional exogenous xylose isomerase gene and/or functional exogenous genes which confer to the cell the ability to convert L-arabinose into D-xylulose 5-phosphate and they may comprise a genetic modification that increase acetyl-CoA synthetase activity.

16 Claims, 1 Drawing Sheet

(56) References Cited

OTHER PUBLICATIONS

Van Maris A. J. A. et al. "Alcoholic fermentation of carbon sources in biomass hydrolysates by *Saccharomyces cerevisiae*: current status" Antonie Van Leeuwenhoek, 90:391-418 (Oct. 11, 2006).
Shams Yazdani S. et al. "Engineering *Escherichia coli* for the efficient conversion of glycerol to ethanol and co-products" Metabolic Engineering, 10;340-351 (Nov. 1, 2008).
Lee W. et al. "Application of sequential integration for metabolic engineering of 1,2-propanediol production in yeast", Metabolic Engineering, Academic Press, pp. 58-65, vol. 8, No. 1, (Jan. 1, 2006).

* cited by examiner

SEQUENCE LISTING

```
<160> NUMBER OF SEQ ID NOS: 51

<210> SEQ ID NO 1
<211> LENGTH: 316
<212> TYPE: PRT
<213> ORGANISM: Escherichia coli

<400> SEQUENCE: 1

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
            20                  25                  30

Val Met Val Gly Ile Asp Pro Gln Ser Asp Gly Leu Ala Arg Ala Arg
        35                  40                  45

Arg Met Gly Val Ala Thr Thr His Glu Gly Val Ile Gly Leu Met Asn
    50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
```

```
    210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
    290                 295                 300

Ala Gln Ser Leu Ala Arg Lys Ala Gly Glu Ala Ala
305                 310                 315


<210> SEQ ID NO 2
<211> LENGTH: 968
<212> TYPE: DNA
<213> ORGANISM: Artificial
<220> FEATURE:
<223> OTHER INFORMATION: mhpF codon optimised

<400> SEQUENCE: 2

ctgcagtcta gatgtctaag agaaaggttg ctatcatcgg ttctggtaac atcggtactg     60

acttgatgat caagatccta agacacggtc aacacttgga aatggctgtt atggttggta    120

tcgacccaca atctgacggt ttggctagag ctagaagaat gggtgttgct accacccacg    180

aaggtgttat cggtttgatg aacatgccag aattcgctga catcgacatc gttttcgacg    240

ctacctctgc tggtgctcac gttaagaacg acgctgcttt gagagaagct aagccagaca    300

tcagattgat cgacttgacc ccagctgcta tcggtccata ctgtgttcca gttgttaact    360

tggaagctaa cgttgaccaa ttaaacgtta acatggttac ctgtggtggt caagctacca    420

tcccaatggt tgctgctgtt tcaagagttg ctagagttca ctacgctgaa atcatcgctt    480

ctatcgcttc taagtctgct ggtccaggta ccagagctaa catcgacgaa ttcaccgaaa    540

ccacctctag ggctatcgaa gttgttggtg gtgctgctaa gggtaaggct atcatcgttt    600

tgaacccagc tgaaccacca ttgatgatga gagacaccgt ttacgttttg tctgacgaag    660

catctcaaga cgacatcgaa gcttcaatca acgaaatggc tgaagctgtt caagcatacg    720

ttccaggtta cagattgaag caaagagttc aattcgaagt tatcccacaa gacaagccag    780

ttaacttgcc aggtgttggt caattctctg gtttgaagac cgctgtttgg ttggaagttg    840

aaggtgctgc tcactacttg ccagcttacg ctggtaactt ggacattatg acctcttctg    900

ctttggctac cgctgaaaag atggctcaat ctttggctag aaaggctggt gaagctgctt    960

aagcgcgc                                                             968


<210> SEQ ID NO 3
<211> LENGTH: 891
<212> TYPE: PRT
<213> ORGANISM: Escherichia coli

<400> SEQUENCE: 3

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
```

-continued

```
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460
```

-continued

```
Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880
```

Ala Lys Ala Glu Lys Lys Ala Lys Lys Ser Ala
885 890

<210> SEQ ID NO 4
<211> LENGTH: 2690
<212> TYPE: DNA
<213> ORGANISM: Artificial
<220> FEATURE:
<223> OTHER INFORMATION: synthetic codon optimimised adhE

<400> SEQUENCE: 4
tctagaaaat ggctgttacc aacgttgctg aattgaacgc tttggttgaa agggttaaga 60
aggctcaaag agaatacgct tctttcaccc aagaacaagt tgacaagatc ttcagagctg 120
ctgctttggc tgctgctgac gctagaatcc cattggctaa gatggctgtt gctgaatctg 180
gtatgggtat cgttgaagac aaggttatca agaaccactt cgcttctgaa tacatctaca 240
acgcttacaa ggacgaaaag acctgtggtg ttttgtcaga agacgacacc ttcggtacca 300
tcaccatcgc tgaaccaatc ggtatcatct gtggtatcgt tccaaccacc aacccaacct 360
ctaccgctat cttcaagtct ttgatctctt tgaagaccag aaacgctatc atcttctctc 420
cacacccaag agctaaagac gctaccaaca aggctgctga catcgttttg caagctgcta 480
tcgctgctgg tgctccaaag gacttgatcg gttggatcga ccaaccatct gttgaattgt 540
ctaacgcttt gatgcaccac ccagacatca acttgatctt ggctaccggt ggtccaggta 600
tggttaaggc tgcttactct tctggtaagc cagctatcgg tgttggtgct ggtaacaccc 660
cagttgttat cgacgaaacc gctgacatca agagagctgt tgcttctgtt ttgatgtcta 720
agaccttcga caacggtgtt atctgtgctt ctgaacaatc tgttgttgtt gttgactctg 780
tttacgacgc tgttagagaa agattcgcta cccacggtgg ttacttgttg caaggtaagg 840
aattgaaggc tgttcaagac gttatcttga agaacggtgc tttgaacgct gctatcgttg 900
gtcaaccagc ttacaagatc gctgaattag ctggtttctc tgttccagaa aacaccaaga 960
tcttgatcgg tgaagttacc gttgttgacg aatctgaacc attcgctcac gaaaagttgt 1020
ctccaacctt ggctatgtac agagctaagg acttcgaaga cgctgttgaa aaagctgaaa 1080
agttggttgc tatgggtggt attggtcaca cctcttgttt gtacaccgac caagacaacc 1140
aaccagctag agtttcttac ttcggtcaaa agatgaagac cgctagaatc ttgatcaaca 1200
ccccagcttc tcaaggtggt atcggtgact tgtacaactt caagttggct ccatctttga 1260
ccttgggttg tggttcttgg ggtggtaact ctatctctga aaacgttggt ccaaagcact 1320
tgatcaacaa gaagaccgtt gctaagagag ctgaaaacat gttgtggcac aagttgccaa 1380
aatctatcta cttcagaaga ggttctttgc caatcgcttt ggacgaagtt atcaccgacg 1440
gtcacaagag agctttgatc gttaccgaca gattcttgtt caacaacggt tacgctgacc 1500
aaatcacctc tgttttgaag gctgctggtg ttgaaaccga agttttcttc gaagttgaag 1560
ctgacccaac cttgtctatc gttagaaagg gtgctgaatt ggctaactct ttcaagccag 1620
acgttatcat cgctttgggt ggtggttctc caatggacgc tgctaagatc atgtgggtta 1680
tgtacgaaca cccagaaacc cacttcgaag aattggcttt gagattcatg gacatcagaa 1740
agagaatcta caagttccca aagatgggtg ttaaggctaa gatgatcgct gttaccacca 1800
cctctggtac cggttctgaa gttaccccat tcgctgttgt taccgacgac gctaccggtc 1860
aaaagtaccc attggctgac tacgctttga ccccagacat ggctatcgtt gacgctaact 1920
tggttatgga catgccaaag tctttgtgtg ctttcggtgg tttggacgct gttacccacg 1980

```
ctatggaagc ttacgtttct gttttggctt ctgaattctc tgacggtcaa gctttgcaag   2040

ctttgaagtt gttgaaggaa tacttgccag cttcttacca cgaaggttct aagaacccag   2100

ttgctagaga aagagttcac tctgctgcta ccatcgctgg tatcgctttc gctaacgctt   2160

tcttgggtgt ttgtcactct atggctcaca agttgggttc tcaattccac atcccacacg   2220

gtttggctaa cgctttgttg atctgtaacg ttatcagata caacgctaac gacaacccaa   2280

ccaagcaaac cgctttctct caatacgaca gaccacaagc tagaagaaga tacgctgaaa   2340

tcgctgacca cttgggtttg tctgctccag gtgacagaac cgctgcaaag atcgaaaagt   2400

tgttggcttg gttggaaacc ttgaaggctg aattgggtat cccaaagtct atcagagaag   2460

ctggtgttca agaagctgac ttcttggcta acgttgacaa gttgtctgaa gacgctttcg   2520

acgaccaatg taccggtgct aacccaagat acccattgat ctctgaattg aagcaaatct   2580

tgttggacac ctactacggt agagactacg ttgaaggtga aaccgctgct aagaaggaag   2640

ctgctccagc taaggctgaa aagaaggcta agaagtctgc ttagcttaag              2690


<210> SEQ ID NO 5
<211> LENGTH: 870
<212> TYPE: PRT
<213> ORGANISM: Entamoeba histolytica

<400> SEQUENCE: 5

Met Ser Thr Gln Gln Thr Met Thr Val Asp Glu His Ile Asn Gln Leu
1               5                   10                  15

Val Arg Lys Ala Gln Val Ala Leu Lys Glu Tyr Leu Lys Pro Glu Tyr
            20                  25                  30

Thr Gln Glu Lys Ile Asp Tyr Ile Val Lys Lys Ala Ser Val Ala Ala
        35                  40                  45

Leu Asp Gln His Cys Ala Leu Ala Ala Ala Ala Val Glu Glu Thr Gly
    50                  55                  60

Arg Gly Ile Phe Glu Asp Lys Ala Thr Lys Asn Ile Phe Ala Cys Glu
65                  70                  75                  80

His Val Thr His Glu Met Arg His Ala Lys Thr Val Gly Ile Ile Asn
                85                  90                  95

Val Asp Pro Leu Tyr Gly Ile Thr Glu Ile Ala Glu Pro Val Gly Val
            100                 105                 110

Val Cys Gly Val Thr Pro Val Thr Asn Pro Thr Ser Thr Ala Ile Phe
        115                 120                 125

Lys Ser Leu Ile Ser Ile Lys Thr Arg Asn Pro Ile Val Phe Ser Phe
    130                 135                 140

His Pro Ser Ala Leu Lys Cys Ser Ile Met Ala Ala Lys Ile Val Arg
145                 150                 155                 160

Asp Ala Ala Ile Ala Ala Gly Ala Pro Glu Asn Cys Ile Gln Trp Ile
                165                 170                 175

Glu Phe Gly Gly Ile Glu Ala Ser Asn Lys Leu Met Asn His Pro Gly
            180                 185                 190

Val Ala Thr Ile Leu Ala Thr Gly Gly Asn Ala Met Val Lys Ala Ala
        195                 200                 205

Tyr Ser Ser Gly Lys Pro Ala Leu Gly Val Gly Ala Gly Asn Val Pro
    210                 215                 220

Thr Tyr Ile Glu Lys Thr Cys Asn Ile Lys Gln Ala Ala Asn Asp Val
225                 230                 235                 240

Val Met Ser Lys Ser Phe Asp Asn Gly Met Ile Cys Ala Ser Glu Gln
                245                 250                 255
```

-continued

```
Ala Ala Ile Ile Asp Lys Glu Ile Tyr Asp Gln Val Val Glu Glu Met
            260                 265                 270

Lys Thr Leu Gly Ala Tyr Phe Ile Asn Glu Glu Glu Lys Ala Lys Leu
        275                 280                 285

Glu Lys Phe Met Phe Gly Val Asn Ala Tyr Ser Ala Asp Val Asn Asn
    290                 295                 300

Ala Arg Leu Asn Pro Lys Cys Pro Gly Met Ser Pro Gln Trp Phe Ala
305                 310                 315                 320

Glu Gln Val Gly Ile Lys Val Pro Glu Asp Cys Asn Ile Ile Cys Ala
                325                 330                 335

Val Cys Lys Glu Val Gly Pro Asn Glu Pro Leu Thr Arg Glu Lys Leu
            340                 345                 350

Ser Pro Val Leu Ala Ile Leu Lys Ala Glu Asn Thr Gln Asp Gly Ile
        355                 360                 365

Asp Lys Ala Glu Ala Met Val Glu Phe Asn Gly Arg Gly His Ser Ala
    370                 375                 380

Ala Ile His Ser Asn Asp Lys Ala Val Val Glu Lys Tyr Ala Leu Thr
385                 390                 395                 400

Met Lys Ala Cys Arg Ile Leu His Asn Thr Pro Ser Ser Gln Gly Gly
                405                 410                 415

Ile Gly Ser Ile Tyr Asn Tyr Ile Trp Pro Ser Phe Thr Leu Gly Cys
            420                 425                 430

Gly Ser Tyr Gly Gly Asn Ser Val Ser Ala Asn Val Thr Tyr His Asn
        435                 440                 445

Leu Leu Asn Ile Lys Arg Leu Ala Asp Arg Arg Asn Asn Leu Gln Trp
    450                 455                 460

Phe Arg Val Pro Pro Lys Ile Phe Phe Glu Pro His Ser Ile Arg Tyr
465                 470                 475                 480

Leu Ala Glu Leu Lys Glu Leu Ser Lys Ile Phe Ile Val Ser Asp Arg
                485                 490                 495

Met Met Tyr Lys Leu Gly Tyr Val Asp Arg Val Met Asp Val Leu Lys
            500                 505                 510

Arg Arg Ser Asn Glu Val Glu Ile Glu Ile Phe Ile Asp Val Glu Pro
        515                 520                 525

Asp Pro Ser Ile Gln Thr Val Gln Lys Gly Leu Ala Val Met Asn Thr
    530                 535                 540

Phe Gly Pro Asp Asn Ile Ile Ala Ile Gly Gly Gly Ser Ala Met Asp
545                 550                 555                 560

Ala Ala Lys Ile Met Trp Leu Leu Tyr Glu His Pro Glu Ala Asp Phe
                565                 570                 575

Phe Ala Met Lys Gln Lys Phe Ile Asp Leu Arg Lys Arg Ala Phe Lys
            580                 585                 590

Phe Pro Thr Met Gly Lys Lys Ala Arg Leu Ile Cys Ile Pro Thr Thr
        595                 600                 605

Ser Gly Thr Gly Ser Glu Val Thr Pro Phe Ala Val Ile Ser Asp His
    610                 615                 620

Glu Thr Gly Lys Lys Tyr Pro Leu Ala Asp Tyr Ser Leu Thr Pro Ser
625                 630                 635                 640

Val Ala Ile Val Asp Pro Met Phe Thr Met Ser Leu Pro Lys Arg Ala
                645                 650                 655

Ile Ala Asp Thr Gly Leu Asp Val Leu Val His Ala Thr Glu Ala Tyr
            660                 665                 670
```

-continued

```
Val Ser Val Met Ala Asn Glu Tyr Thr Asp Gly Leu Ala Arg Glu Ala
        675                 680                 685

Val Lys Leu Val Phe Glu Asn Leu Leu Lys Ser Tyr Asn Gly Asp Leu
    690                 695                 700

Glu Ala Arg Glu Lys Met His Asn Ala Ala Thr Ile Ala Gly Met Ala
705                 710                 715                 720

Phe Ala Ser Ala Phe Leu Gly Met Asp His Ser Met Ala His Lys Val
                725                 730                 735

Gly Ala Ala Phe His Leu Pro His Gly Arg Cys Val Ala Val Leu Leu
            740                 745                 750

Pro His Val Ile Arg Tyr Asn Gly Gln Lys Pro Arg Lys Leu Ala Met
        755                 760                 765

Trp Pro Lys Tyr Asn Phe Tyr Lys Ala Asp Gln Arg Tyr Met Glu Leu
    770                 775                 780

Ala Gln Met Val Gly Leu Lys Cys Asn Thr Pro Ala Glu Gly Val Glu
785                 790                 795                 800

Ala Phe Ala Lys Ala Cys Glu Glu Leu Met Lys Ala Thr Glu Thr Ile
                805                 810                 815

Thr Gly Phe Lys Lys Ala Asn Ile Asp Glu Ala Ala Trp Met Ser Lys
            820                 825                 830

Val Pro Glu Met Ala Leu Leu Ala Phe Glu Asp Gln Cys Ser Pro Ala
        835                 840                 845

Asn Pro Arg Val Pro Met Val Lys Asp Met Glu Lys Ile Leu Lys Ala
    850                 855                 860

Ala Tyr Tyr Pro Ile Ala
865                 870


<210> SEQ ID NO 6
<211> LENGTH: 2627
<212> TYPE: DNA
<213> ORGANISM: Artificial
<220> FEATURE:
<223> OTHER INFORMATION: synthetic codon optimised ADH2

<400> SEQUENCE: 6

tctagaaaat gtctacccaa caaaccatga ccgttgacga acacatcaac caattagtta      60

gaaaggctca agttgctttg aaggaatact tgaagccaga atacacccaa gaaaagatcg     120

actacatcgt taagaaggct tctgttgctg ctttggacca acactgtgct ttggctgctg     180

ctgctgttga agaaaccggt agaggtatct tcgaagacaa ggctaccaag aacatcttcg     240

cttgtgaaca cgttacccac gaaatgagac acgctaagac cgttggtatc atcaacgttg     300

acccattgta cggtatcacc gaaatcgctg aaccagttgg tgttgtttgt ggtgttaccc     360

cagttaccaa cccaacctct accgctatct tcaagtcttt gatctctatc aagaccagaa     420

acccaatcgt tttctctttc cacccatctg ctttgaagtg ttctattatg gctgctaaaa     480

tcgttagaga cgctgctatc gctgctggtg ctccagaaaa ctgtatccaa tggatcgaat     540

tcggtggtat cgaagcttct aacaagttga tgaaccaccc aggtgttgct actatcttgg     600

ctaccggtgg taacgctatg gttaaggctg catactcttc tggtaagcca gctttgggtg     660

ttggtgctgg taacgttcca acctacatcg aaaagacctg taacatcaag caagctgcta     720

acgacgttgt tatgtctaag tctttcgaca acggtatgat ctgtgcttct gaacaagctg     780

ctatcatcga caaggaaatc tacgaccaag ttgttgaaga aatgaagacc ttgggtgctt     840

acttcatcaa cgaagaagaa aaggctaagt tggaaaagtt catgttcggt gttaacgctt     900
```

-continued

```
actctgctga cgttaacaac gctagattga acccaaagtg tccaggtatg tctccacaat    960
ggttcgctga acaagttggt atcaaggtac cagaagactg taacatcatc tgtgctgttt   1020
gtaaggaagt tggtccaaac gaaccattga ccagagaaaa gttgtctcca gttttggcta   1080
tcttgaaagc tgaaaacacc caagacggta tcgacaaggc tgaagctatg gttgaattta   1140
acggtagagg tcactctgct gctatccact ctaacgacaa ggctgttgtt gaaaagtacg   1200
ctttgaccat gaaggcttgt agaatcttgc acaacacccc atcttctcaa ggtggtatcg   1260
gttctatcta caactacatc tggccatctt tcaccttggg ttgtggttct tacggtggta   1320
actctgtttc tgctaacgtt acctaccaca acttgttgaa catcaagaga ttggctgaca   1380
gaagaaacaa cttgcaatgg ttcagagttc caccaaagat cttcttcgaa ccacactcta   1440
tcagatactt ggctgaattg aaggaattgt ctaagatctt catcgtttct gacagaatga   1500
tgtacaagtt gggttacgtt gacagagtta tggacgtttt gaagagaaga tctaacgaag   1560
ttgaaatcga aatcttcatc gacgttgaac cagacccatc tatccaaacc gttcaaaagg   1620
gtttggctgt tatgaacacc ttcggtccag acaacatcat cgctatcggt ggtggttctg   1680
ctatggacgc tgctaagatc atgtggttgt tgtacgaaca cccagaagct gacttcttcg   1740
ctatgaagca aaagttcatc gacttgagaa agagagcttt caagttccca accatgggta   1800
agaaggctag attgatctgt atcccaacca cctctggtac cggttctgaa gttaccccat   1860
tcgctgttat ctctgaccac gaaaccggta agaagtaccc attggctgac tactctttga   1920
ccccatctgt tgctatcgtt gacccaatgt tcaccatgtc tttgccaaag agagctatcg   1980
ctgacaccgg tttggacgtt ttggttcacg ctaccgaagc ttacgtttct gttatggcta   2040
acgaatacac cgacggtttg gctagagaag ctgttaagtt ggtttttgaa aacttgttga   2100
agtcttacaa cggtgacttg gaagctagag aaaagatgca caacgctgct accatcgctg   2160
gtatggcttt cgcttctgct ttcttgggta tggaccactc tatggctcac aaggttggtg   2220
ctgctttcca cttgccacac ggtagatgtg ttgctgtttt gttgccacac gttatcagat   2280
acaacggtca aaagccaaga aagttggcta tgtggccaaa gtacaacttc tacaaggctg   2340
accaaagata catggaattg gctcaaatgg ttggtttgaa gtgtaacacc ccagctgaag   2400
gtgttgaagc tttcgctaag gcttgtgaag aattgatgaa ggctaccgaa accatcaccg   2460
gtttcaagaa ggctaacatc gacgaagctg cttggatgtc taaggttcca gaaatggctt   2520
tgttggcttt cgaagaccaa tgttctccag ctaacccaag agttccaatg gttaaggaca   2580
tggaaaagat cttgaaggct gcttactacc caatcgctta gcttaag                 2627
```

<210> SEQ ID NO 7
<211> LENGTH: 367
<212> TYPE: PRT
<213> ORGANISM: Escherichia coli

<400> SEQUENCE: 7

```
Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
```

```
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365


<210> SEQ ID NO 8
<211> LENGTH: 584
<212> TYPE: PRT
<213> ORGANISM: Saccharomyces cerevisiae

<400> SEQUENCE: 8

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80
```

```
Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140

Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
            180                 185                 190

Ser Leu Asp His Cys Lys Val Pro Gly Arg Lys Phe Glu Ser Glu Leu
        195                 200                 205

Asn Glu Lys Gln Met Glu Leu Gly Met Gly Ile His Asn Glu Pro Gly
    210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Asp Glu Val Val Leu Leu Val Asn Asn Leu
            260                 265                 270

Gly Gly Val Ser Asn Phe Val Ile Ser Ser Ile Thr Ser Lys Thr Thr
        275                 280                 285

Asp Phe Leu Lys Glu Asn Tyr Asn Ile Thr Pro Val Gln Thr Ile Ala
    290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
            340                 345                 350

Trp Pro Ile Ala Asp Phe Glu Lys Thr Ser Ala Pro Ser Val Asn Asp
        355                 360                 365

Asp Leu Leu His Asn Glu Val Thr Ala Lys Ala Val Gly Thr Tyr Asp
    370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
            420                 425                 430

Leu Asp Lys Leu Ser Lys Asp Ser Leu Ser Gln Ala Val Ala Gln Ile
        435                 440                 445

Ser Asp Phe Ile Glu Gly Ser Met Gly Gly Thr Ser Gly Gly Leu Tyr
    450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495

Ile Ala Leu Asp Thr Leu Tyr Lys Tyr Thr Lys Ala Arg Lys Gly Ser
```

```
            500                 505                 510

Ser Thr Met Ile Asp Ala Leu Glu Pro Phe Val Lys Glu Phe Thr Ala
        515                 520                 525

Ser Lys Asp Phe Asn Lys Ala Val Lys Ala Ala Glu Glu Gly Ala Lys
    530                 535                 540

Ser Thr Ala Thr Phe Glu Ala Lys Phe Gly Arg Ala Ser Tyr Val Gly
545                 550                 555                 560

Asp Ser Ser Gln Val Glu Asp Pro Gly Ala Val Gly Leu Cys Glu Phe
                565                 570                 575

Leu Lys Gly Val Gln Ser Ala Leu
            580


<210> SEQ ID NO 9
<211> LENGTH: 591
<212> TYPE: PRT
<213> ORGANISM: Saccharomyces cerevisiae

<400> SEQUENCE: 9

Met Ser His Lys Gln Phe Lys Ser Asp Gly Asn Ile Val Thr Pro Tyr
1               5                   10                  15

Leu Leu Gly Leu Ala Arg Ser Asn Pro Gly Leu Thr Val Ile Lys His
            20                  25                  30

Asp Arg Val Val Phe Arg Thr Ala Ser Ala Pro Asn Ser Gly Asn Pro
        35                  40                  45

Pro Lys Val Ser Leu Val Ser Gly Gly Gly Ser Gly His Glu Pro Thr
    50                  55                  60

His Ala Gly Phe Val Gly Glu Gly Ala Leu Asp Ala Ile Ala Ala Gly
65                  70                  75                  80

Ala Ile Phe Ala Ser Pro Ser Thr Lys Gln Ile Tyr Ser Ala Ile Lys
                85                  90                  95

Ala Val Glu Ser Pro Lys Gly Thr Leu Ile Ile Val Lys Asn Tyr Thr
            100                 105                 110

Gly Asp Ile Ile His Phe Gly Leu Ala Ala Glu Arg Ala Lys Ala Ala
        115                 120                 125

Gly Met Lys Val Glu Leu Val Ala Val Gly Asp Asp Val Ser Val Gly
    130                 135                 140

Lys Lys Lys Gly Ser Leu Val Gly Arg Arg Gly Leu Gly Ala Thr Val
145                 150                 155                 160

Leu Val His Lys Ile Ala Gly Ala Ala Ala Ser His Gly Leu Glu Leu
                165                 170                 175

Ala Glu Val Ala Glu Val Ala Gln Ser Val Val Asp Asn Ser Val Thr
            180                 185                 190

Ile Ala Ala Ser Leu Asp His Cys Thr Val Pro Gly His Lys Pro Glu
        195                 200                 205

Ala Ile Leu Gly Glu Asn Glu Tyr Glu Ile Gly Met Gly Ile His Asn
    210                 215                 220

Glu Ser Gly Thr Tyr Lys Ser Ser Pro Leu Pro Ser Ile Ser Glu Leu
225                 230                 235                 240

Val Ser Gln Met Leu Pro Leu Leu Leu Asp Glu Asp Glu Asp Arg Ser
                245                 250                 255

Tyr Val Lys Phe Glu Pro Lys Glu Asp Val Val Leu Met Val Asn Asn
            260                 265                 270

Met Gly Gly Met Ser Asn Leu Glu Leu Gly Tyr Ala Ala Glu Val Ile
        275                 280                 285
```

-continued

```
Ser Glu Gln Leu Ile Asp Lys Tyr Gln Ile Val Pro Lys Arg Thr Ile
    290                 295                 300

Thr Gly Ala Phe Ile Thr Ala Leu Asn Gly Pro Gly Phe Gly Ile Thr
305                 310                 315                 320

Leu Met Asn Ala Ser Lys Ala Gly Gly Asp Ile Leu Lys Tyr Phe Asp
                325                 330                 335

Tyr Pro Thr Thr Ala Ser Gly Trp Asn Gln Met Tyr His Ser Ala Lys
            340                 345                 350

Asp Trp Glu Val Leu Ala Lys Gly Gln Val Pro Thr Ala Pro Ser Leu
        355                 360                 365

Lys Thr Leu Arg Asn Glu Lys Gly Ser Gly Val Lys Ala Asp Tyr Asp
    370                 375                 380

Thr Phe Ala Lys Ile Leu Leu Ala Gly Ile Ala Lys Ile Asn Glu Val
385                 390                 395                 400

Glu Pro Lys Val Thr Trp Tyr Asp Thr Ile Ala Gly Asp Gly Asp Cys
                405                 410                 415

Gly Thr Thr Leu Val Ser Gly Gly Glu Ala Leu Glu Glu Ala Ile Lys
            420                 425                 430

Asn His Thr Leu Arg Leu Glu Asp Ala Ala Leu Gly Ile Glu Asp Ile
        435                 440                 445

Ala Tyr Met Val Glu Asp Ser Met Gly Gly Thr Ser Gly Gly Leu Tyr
    450                 455                 460

Ser Ile Tyr Leu Ser Ala Leu Ala Gln Gly Val Arg Asp Ser Gly Asp
465                 470                 475                 480

Lys Glu Leu Thr Ala Glu Thr Phe Lys Lys Ala Ser Asn Val Ala Leu
                485                 490                 495

Asp Ala Leu Tyr Lys Tyr Thr Arg Ala Arg Pro Gly Tyr Arg Thr Leu
            500                 505                 510

Ile Asp Ala Leu Gln Pro Phe Val Glu Ala Leu Lys Ala Gly Lys Gly
        515                 520                 525

Pro Arg Ala Ala Ala Gln Ala Ala Tyr Asp Gly Ala Glu Lys Thr Arg
    530                 535                 540

Lys Met Asp Ala Leu Val Gly Arg Ala Ser Tyr Val Ala Lys Glu Glu
545                 550                 555                 560

Leu Arg Lys Leu Asp Ser Glu Gly Gly Leu Pro Asp Pro Gly Ala Val
                565                 570                 575

Gly Leu Ala Ala Leu Leu Asp Gly Phe Val Thr Ala Ala Gly Tyr
            580                 585                 590


<210> SEQ ID NO 10
<211> LENGTH: 560
<212> TYPE: PRT
<213> ORGANISM: Saccharomyces cerevisiae

<400> SEQUENCE: 10

Met Ser Leu Ile Ser Ile Leu Ser Pro Leu Ile Thr Ser Glu Gly Leu
1               5                   10                  15

Asp Ser Arg Ile Lys Pro Ser Pro Lys Lys Asp Ala Ser Thr Thr Thr
            20                  25                  30

Lys Pro Ser Leu Trp Lys Thr Thr Glu Phe Lys Phe Tyr Tyr Ile Ala
        35                  40                  45

Phe Leu Val Val Val Pro Leu Met Phe Tyr Ala Gly Leu Gln Ala Ser
    50                  55                  60

Ser Pro Glu Asn Pro Asn Tyr Ala Arg Tyr Glu Arg Leu Leu Ser Gln
65                  70                  75                  80
```

-continued

```
Gly Trp Leu Phe Gly Arg Lys Val Asp Asn Ser Asp Ser Gln Tyr Arg
                85                  90                  95

Phe Phe Arg Asp Asn Phe Ala Leu Leu Ser Val Leu Met Leu Val His
            100                 105                 110

Thr Ser Ile Lys Arg Ile Val Leu Tyr Ser Thr Asn Ile Thr Lys Leu
        115                 120                 125

Arg Phe Asp Leu Ile Phe Gly Leu Ile Phe Leu Val Ala Ala His Gly
    130                 135                 140

Val Asn Ser Ile Arg Ile Leu Ala His Met Leu Ile Leu Tyr Ala Ile
145                 150                 155                 160

Ala His Val Leu Lys Asn Phe Arg Arg Ile Ala Thr Ile Ser Ile Trp
                165                 170                 175

Ile Tyr Gly Ile Ser Thr Leu Phe Ile Asn Asp Asn Phe Arg Ala Tyr
            180                 185                 190

Pro Phe Gly Asn Ile Cys Ser Phe Leu Ser Pro Leu Asp His Trp Tyr
        195                 200                 205

Arg Gly Ile Ile Pro Arg Trp Asp Val Phe Phe Asn Phe Thr Leu Leu
    210                 215                 220

Arg Val Leu Ser Tyr Asn Leu Asp Phe Leu Glu Arg Trp Glu Asn Leu
225                 230                 235                 240

Gln Lys Lys Lys Ser Pro Ser Tyr Glu Ser Lys Glu Ala Lys Ser Ala
                245                 250                 255

Ile Leu Leu Asn Glu Arg Ala Arg Leu Thr Ala Ala His Pro Ile Gln
            260                 265                 270

Asp Tyr Ser Leu Met Asn Tyr Ile Ala Tyr Val Thr Tyr Thr Pro Leu
        275                 280                 285

Phe Ile Ala Gly Pro Ile Ile Thr Phe Asn Asp Tyr Val Tyr Gln Ser
    290                 295                 300

Lys His Thr Leu Pro Ser Ile Asn Phe Lys Phe Ile Phe Tyr Tyr Ala
305                 310                 315                 320

Val Arg Phe Val Ile Ala Leu Leu Ser Met Glu Phe Ile Leu His Phe
                325                 330                 335

Leu His Val Val Ala Ile Ser Lys Thr Lys Ala Trp Glu Asn Asp Thr
            340                 345                 350

Pro Phe Gln Ile Ser Met Ile Gly Leu Phe Asn Leu Asn Ile Ile Trp
        355                 360                 365

Leu Lys Leu Leu Ile Pro Trp Arg Leu Phe Arg Leu Trp Ala Leu Leu
    370                 375                 380

Asp Gly Ile Asp Thr Pro Glu Asn Met Ile Arg Cys Val Asp Asn Asn
385                 390                 395                 400

Tyr Ser Ser Leu Ala Phe Trp Arg Ala Trp His Arg Ser Tyr Asn Lys
                405                 410                 415

Trp Val Val Arg Tyr Ile Tyr Ile Pro Leu Gly Gly Ser Lys Asn Arg
            420                 425                 430

Val Leu Thr Ser Leu Ala Val Phe Ser Phe Val Ala Ile Trp His Asp
        435                 440                 445

Ile Glu Leu Lys Leu Leu Leu Trp Gly Trp Leu Ile Val Leu Phe Leu
    450                 455                 460

Leu Pro Glu Ile Phe Ala Thr Gln Ile Phe Ser His Tyr Thr Asp Ala
465                 470                 475                 480

Val Trp Tyr Arg His Val Cys Ala Val Gly Ala Val Phe Asn Ile Trp
                485                 490                 495
```

-continued

```
Val Met Met Ile Ala Asn Leu Phe Gly Phe Cys Leu Gly Ser Asp Gly
            500                 505                 510

Thr Lys Lys Leu Leu Ser Asp Met Phe Cys Thr Val Ser Gly Phe Lys
        515                 520                 525

Phe Val Ile Leu Ala Ser Val Ser Leu Phe Ile Ala Val Gln Ile Met
    530                 535                 540

Phe Glu Ile Arg Glu Glu Glu Lys Arg His Gly Ile Tyr Leu Lys Cys
545                 550                 555                 560


<210> SEQ ID NO 11
<211> LENGTH: 609
<212> TYPE: PRT
<213> ORGANISM: Saccharomyces cerevisiae

<400> SEQUENCE: 11

Met Ser Met Leu Arg Ile Trp Ser Cys Ile Val His Phe Phe Ser Val
1               5                   10                  15

Gln Ala Leu Asp Ser Arg Ile Lys Pro Asp Ile Glu Phe Lys Arg Arg
            20                  25                  30

Gln Arg Ile Phe Ile Asn Ser Ser Lys Glu Glu Asn Gly Ser Ser Ser
        35                  40                  45

Ser Ala Val Thr Val Thr Arg Asn Pro Val Leu Ser Ser Asn Ser Pro
    50                  55                  60

Ser Pro Pro Leu Trp Asn Thr Trp Glu Phe Arg Leu Tyr Tyr Leu Ala
65                  70                  75                  80

Phe Thr Val Val Val Pro Phe Met Ile Lys Ala Ala Leu Ala Thr Ser
                85                  90                  95

Ser Glu Ser Asn Pro Asn Tyr Tyr Lys Phe Ser Gly Leu Leu Ala His
            100                 105                 110

Gly Trp Ile Leu Gly Arg Lys Val Asp Asn Ser Asp Pro Gln Tyr Arg
        115                 120                 125

Phe Phe Arg Ser Asn Phe Phe Leu Leu Ala Ile Leu Ile Leu Leu Gln
    130                 135                 140

Ile Ile Leu Lys Lys Val Phe Val Lys Phe Ser Lys Ile Pro Lys Thr
145                 150                 155                 160

Lys Phe Asp Phe Ala Cys Gly Leu Val Phe Val Cys Phe Met Tyr Gly
                165                 170                 175

Ile Asn Ser Val Lys Leu Phe Thr His Ala Phe Ile Phe Phe Thr Leu
            180                 185                 190

Ala His Ser Leu Lys Arg Lys Arg Leu Ile Ala Ala Phe Ala Ile Trp
        195                 200                 205

Ser Tyr Gly Ile Phe Thr Leu Phe Ile Asn Gln Lys Met Lys Asn Leu
    210                 215                 220

Pro Phe Asn Asn Ile Ala Ile Ile Leu Ser Pro Met Asp Gln Trp Tyr
225                 230                 235                 240

Lys Gly Ile Val Pro Arg Trp Asp Phe Phe Phe Asn Phe Thr Leu Leu
                245                 250                 255

Arg Leu Leu Ser Tyr Ser Met Asp Phe Leu Glu Arg Trp His Glu Gln
            260                 265                 270

Leu Ser Arg Gln Pro Ser Ile Asp Tyr Asp Asp Arg Arg Pro Glu Phe
        275                 280                 285

Arg Lys Ser Leu Ser Gly Ser Thr Leu Gln Thr Ile Tyr Glu Ser Gly
    290                 295                 300

Lys Asn Val Leu Glu Glu Lys Glu Arg Leu Val Ala Glu His His Ile
305                 310                 315                 320
```

```
Gln Asp Tyr Asn Phe Ile Asn Phe Ile Ala Tyr Ile Thr Tyr Ala Pro
                325                 330                 335

Leu Phe Leu Val Gly Pro Ile Ile Thr Phe Asn Asp Tyr Leu Tyr Gln
            340                 345                 350

Ser Glu Asn Lys Leu Pro Ser Leu Thr Lys Lys Asn Ile Gly Phe Tyr
        355                 360                 365

Ala Leu Lys Val Phe Ser Ser Leu Leu Leu Met Glu Ile Ile Leu His
    370                 375                 380

Tyr Ile Tyr Val Gly Ala Ile Ala Arg Thr Lys Ala Trp Asn Asn Asp
385                 390                 395                 400

Thr Pro Leu Gln Gln Ala Met Ile Ala Leu Phe Asn Leu Asn Ile Met
                405                 410                 415

Tyr Leu Lys Leu Leu Ile Pro Trp Arg Leu Phe Arg Leu Trp Ala Met
            420                 425                 430

Val Asp Gly Ile Asp Ala Pro Glu Asn Met Leu Arg Cys Val Asp Asn
        435                 440                 445

Asn Tyr Ser Thr Val Gly Phe Trp Arg Ala Trp His Thr Ser Phe Asn
    450                 455                 460

Lys Trp Val Ile Arg Tyr Ile Tyr Val Pro Phe Gly Gly Ser Asn Asn
465                 470                 475                 480

Lys Ile Leu Thr Ser Phe Ala Val Phe Ser Phe Val Ala Ile Trp His
                485                 490                 495

Asp Ile Gln Leu Arg Val Leu Phe Trp Gly Trp Leu Thr Val Leu Leu
            500                 505                 510

Leu Leu Gly Glu Thr Tyr Ile Thr Asn Cys Phe Ser Arg Tyr Arg Phe
        515                 520                 525

Arg Ser Trp Tyr Arg Phe Val Cys Gly Ile Gly Ala Ala Ile Asn Ile
    530                 535                 540

Cys Met Met Met Ile Ile Asn Val Tyr Gly Phe Cys Leu Gly Ala Glu
545                 550                 555                 560

Gly Thr Lys Leu Leu Leu Lys Gly Ile Phe Asn Asn Ser His Ser Pro
                565                 570                 575

Glu Phe Leu Thr Ala Val Met Val Ser Leu Phe Ile Ala Val Gln Val
            580                 585                 590

Met Phe Glu Ile Arg Glu Glu Glu Lys Arg His Gly Ile Asn Leu Lys
        595                 600                 605

Cys


<210> SEQ ID NO 12
<211> LENGTH: 669
<212> TYPE: PRT
<213> ORGANISM: Saccharomyces cerevisiae

<400> SEQUENCE: 12

Met Ser Asn Pro Gln Lys Ala Leu Asn Asp Phe Leu Ser Ser Glu Ser
1               5                   10                  15

Val His Thr His Asp Ser Ser Arg Lys Gln Ser Asn Lys Gln Ser Ser
            20                  25                  30

Asp Glu Gly Arg Ser Ser Ser Gln Pro Ser His His His Ser Gly Gly
        35                  40                  45

Thr Asn Asn Asn Asn Asn Asn Asn Asn Asn Asn Asn Asn Ser Asn Asn
    50                  55                  60

Asn Asn Asn Gly Asn Asp Gly Gly Asn Asp Asp Asp Tyr Asp Tyr Glu
65                  70                  75                  80
```

```
Met Gln Asp Tyr Arg Pro Ser Pro Gln Ser Ala Arg Pro Thr Pro Thr
                85                  90                  95

Tyr Val Pro Gln Tyr Ser Val Glu Ser Gly Thr Ala Phe Pro Ile Gln
            100                 105                 110

Glu Val Ile Pro Ser Ala Tyr Ile Asn Thr Gln Asp Ile Asn His Lys
        115                 120                 125

Asp Asn Gly Pro Pro Ser Ala Ser Ser Asn Arg Ala Phe Arg Pro Arg
    130                 135                 140

Gly Gln Thr Thr Val Ser Ala Asn Val Leu Asn Ile Glu Asp Phe Tyr
145                 150                 155                 160

Lys Asn Ala Asp Asp Ala His Thr Ile Pro Glu Ser His Leu Ser Arg
                165                 170                 175

Arg Arg Ser Arg Ser Arg Ala Thr Ser Asn Ala Gly His Ser Ala Asn
            180                 185                 190

Thr Gly Ala Thr Asn Gly Arg Thr Thr Gly Ala Gln Thr Asn Met Glu
        195                 200                 205

Ser Asn Glu Ser Pro Arg Asn Val Pro Ile Met Val Lys Pro Lys Thr
    210                 215                 220

Leu Tyr Gln Asn Pro Gln Thr Pro Thr Val Leu Pro Ser Thr Tyr His
225                 230                 235                 240

Pro Ile Asn Lys Trp Ser Ser Val Lys Asn Thr Tyr Leu Lys Glu Phe
                245                 250                 255

Leu Ala Glu Phe Met Gly Thr Met Val Met Ile Ile Phe Gly Ser Ala
            260                 265                 270

Val Val Cys Gln Val Asn Val Ala Gly Lys Ile Gln Gln Asp Asn Phe
        275                 280                 285

Asn Val Ala Leu Asp Asn Leu Asn Val Thr Gly Ser Ser Ala Glu Thr
    290                 295                 300

Ile Asp Ala Met Lys Ser Leu Thr Ser Leu Val Ser Ser Val Ala Gly
305                 310                 315                 320

Gly Thr Phe Asp Asp Val Ala Leu Gly Trp Ala Ala Ala Val Val Met
                325                 330                 335

Gly Tyr Phe Cys Ala Gly Gly Ser Ala Ile Ser Gly Ala His Leu Asn
            340                 345                 350

Pro Ser Ile Thr Leu Ala Asn Leu Val Tyr Arg Gly Phe Pro Leu Lys
        355                 360                 365

Lys Val Pro Tyr Tyr Phe Ala Gly Gln Leu Ile Gly Ala Phe Thr Gly
    370                 375                 380

Ala Leu Ile Leu Phe Ile Trp Tyr Lys Arg Val Leu Gln Glu Ala Tyr
385                 390                 395                 400

Ser Asp Trp Trp Met Asn Glu Ser Val Ala Gly Met Phe Cys Val Phe
                405                 410                 415

Pro Lys Pro Tyr Leu Ser Ser Gly Arg Gln Phe Phe Ser Glu Phe Leu
            420                 425                 430

Cys Gly Ala Met Leu Gln Ala Gly Thr Phe Ala Leu Thr Asp Pro Tyr
        435                 440                 445

Thr Cys Leu Ser Ser Asp Val Phe Pro Leu Met Met Phe Ile Leu Ile
    450                 455                 460

Phe Ile Ile Asn Ala Ser Met Ala Tyr Gln Thr Gly Thr Ala Met Asn
465                 470                 475                 480

Leu Ala Arg Asp Leu Gly Pro Arg Leu Ala Leu Tyr Ala Val Gly Phe
                485                 490                 495
```

-continued

```
Asp His Lys Met Leu Trp Val His His His His Phe Phe Trp Val Pro
            500                 505                 510

Met Val Gly Pro Phe Ile Gly Ala Leu Met Gly Gly Leu Val Tyr Asp
        515                 520                 525

Val Cys Ile Tyr Gln Gly His Glu Ser Pro Val Asn Trp Ser Leu Pro
    530                 535                 540

Val Tyr Lys Glu Met Ile Met Arg Ala Trp Phe Arg Arg Pro Gly Trp
545                 550                 555                 560

Lys Lys Arg Asn Arg Ala Arg Arg Thr Ser Asp Leu Ser Asp Phe Ser
                565                 570                 575

Tyr Asn Asn Asp Asp Asp Glu Glu Phe Gly Glu Arg Met Ala Leu Gln
            580                 585                 590

Lys Thr Lys Thr Lys Ser Ser Ile Ser Asp Asn Glu Asn Glu Ala Gly
        595                 600                 605

Glu Lys Lys Val Gln Phe Lys Ser Val Gln Arg Gly Lys Arg Thr Phe
    610                 615                 620

Gly Gly Ile Pro Thr Ile Leu Glu Glu Glu Asp Ser Ile Glu Thr Ala
625                 630                 635                 640

Ser Leu Gly Ala Thr Thr Thr Asp Ser Ile Gly Leu Ser Asp Thr Ser
                645                 650                 655

Ser Glu Asp Ser His Tyr Gly Asn Ala Lys Lys Val Thr
            660                 665


<210> SEQ ID NO 13
<211> LENGTH: 713
<212> TYPE: PRT
<213> ORGANISM: Saccharomyces cerevisiae

<400> SEQUENCE: 13

Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ala Thr Ala
            20                  25                  30

Gln Gln Lys Lys Glu His Glu Tyr Glu His Leu Thr Ser Val Lys Ile
        35                  40                  45

Val Pro Gln Arg Pro Ile Ser Asp Arg Leu Gln Pro Ala Ile Ala Thr
    50                  55                  60

His Tyr Ser Pro His Leu Asp Gly Leu Gln Asp Tyr Gln Arg Leu His
65                  70                  75                  80

Lys Glu Ser Ile Glu Asp Pro Ala Lys Phe Phe Gly Ser Lys Ala Thr
                85                  90                  95

Gln Phe Leu Asn Trp Ser Lys Pro Phe Asp Lys Val Phe Ile Pro Asp
            100                 105                 110

Pro Lys Thr Gly Arg Pro Ser Phe Gln Asn Asn Ala Trp Phe Leu Asn
        115                 120                 125

Gly Gln Leu Asn Ala Cys Tyr Asn Cys Val Asp Arg His Ala Leu Lys
    130                 135                 140

Thr Pro Asn Lys Lys Ala Ile Ile Phe Glu Gly Asp Glu Pro Gly Gln
145                 150                 155                 160

Gly Tyr Ser Ile Thr Tyr Lys Glu Leu Leu Glu Glu Val Cys Gln Val
                165                 170                 175

Ala Gln Val Leu Thr Tyr Ser Met Gly Val Arg Lys Gly Asp Thr Val
            180                 185                 190

Ala Val Tyr Met Pro Met Val Pro Glu Ala Ile Ile Thr Leu Leu Ala
        195                 200                 205
```

-continued

```
Ile Ser Arg Ile Gly Ala Ile His Ser Val Val Phe Ala Gly Phe Ser
    210                 215                 220

Ser Asn Ser Leu Arg Asp Arg Ile Asn Asp Gly Asp Ser Lys Val Val
225                 230                 235                 240

Ile Thr Thr Asp Glu Ser Asn Arg Gly Gly Lys Val Ile Glu Thr Lys
                245                 250                 255

Arg Ile Val Asp Asp Ala Leu Arg Glu Thr Pro Gly Val Arg His Val
            260                 265                 270

Leu Val Tyr Arg Lys Thr Asn Asn Pro Ser Val Ala Phe His Ala Pro
        275                 280                 285

Arg Asp Leu Asp Trp Ala Thr Glu Lys Lys Lys Tyr Lys Thr Tyr Tyr
    290                 295                 300

Pro Cys Thr Pro Val Asp Ser Glu Asp Pro Leu Phe Leu Leu Tyr Thr
305                 310                 315                 320

Ser Gly Ser Thr Gly Ala Pro Lys Gly Val Gln His Ser Thr Ala Gly
                325                 330                 335

Tyr Leu Leu Gly Ala Leu Leu Thr Met Arg Tyr Thr Phe Asp Thr His
            340                 345                 350

Gln Glu Asp Val Phe Phe Thr Ala Gly Asp Ile Gly Trp Ile Thr Gly
        355                 360                 365

His Thr Tyr Val Val Tyr Gly Pro Leu Leu Tyr Gly Cys Ala Thr Leu
    370                 375                 380

Val Phe Glu Gly Thr Pro Ala Tyr Pro Asn Tyr Ser Arg Tyr Trp Asp
385                 390                 395                 400

Ile Ile Asp Glu His Lys Val Thr Gln Phe Tyr Val Ala Pro Thr Ala
                405                 410                 415

Leu Arg Leu Leu Lys Arg Ala Gly Asp Ser Tyr Ile Glu Asn His Ser
            420                 425                 430

Leu Lys Ser Leu Arg Cys Leu Gly Ser Val Gly Glu Pro Ile Ala Ala
        435                 440                 445

Glu Val Trp Glu Trp Tyr Ser Glu Lys Ile Gly Lys Asn Glu Ile Pro
    450                 455                 460

Ile Val Asp Thr Tyr Trp Gln Thr Glu Ser Gly Ser His Leu Val Thr
465                 470                 475                 480

Pro Leu Ala Gly Gly Val Thr Pro Met Lys Pro Gly Ser Ala Ser Phe
                485                 490                 495

Pro Phe Phe Gly Ile Asp Ala Val Val Leu Asp Pro Asn Thr Gly Glu
            500                 505                 510

Glu Leu Asn Thr Ser His Ala Glu Gly Val Leu Ala Val Lys Ala Ala
        515                 520                 525

Trp Pro Ser Phe Ala Arg Thr Ile Trp Lys Asn His Asp Arg Tyr Leu
    530                 535                 540

Asp Thr Tyr Leu Asn Pro Tyr Pro Gly Tyr Tyr Phe Thr Gly Asp Gly
545                 550                 555                 560

Ala Ala Lys Asp Lys Asp Gly Tyr Ile Trp Ile Leu Gly Arg Val Asp
                565                 570                 575

Asp Val Val Asn Val Ser Gly His Arg Leu Ser Thr Ala Glu Ile Glu
            580                 585                 590

Ala Ala Ile Ile Glu Asp Pro Ile Val Ala Glu Cys Ala Val Val Gly
        595                 600                 605

Phe Asn Asp Asp Leu Thr Gly Gln Ala Val Ala Ala Phe Val Val Leu
    610                 615                 620
```

```
Lys Asn Lys Ser Ser Trp Ser Thr Ala Thr Asp Asp Glu Leu Gln Asp
625                 630                 635                 640

Ile Lys Lys His Leu Val Phe Thr Val Arg Lys Asp Ile Gly Pro Phe
                645                 650                 655

Ala Ala Pro Lys Leu Ile Ile Leu Val Asp Asp Leu Pro Lys Thr Arg
            660                 665                 670

Ser Gly Lys Ile Met Arg Arg Ile Leu Arg Lys Ile Leu Ala Gly Glu
        675                 680                 685

Ser Asp Gln Leu Gly Asp Val Ser Thr Leu Ser Asn Pro Gly Ile Val
    690                 695                 700

Arg His Leu Ile Asp Ser Val Lys Leu
705                 710


<210> SEQ ID NO 14
<211> LENGTH: 683
<212> TYPE: PRT
<213> ORGANISM: Saccharomyces cerevisiae

<400> SEQUENCE: 14

Met Thr Ile Lys Glu His Lys Val Val Tyr Glu Ala His Asn Val Lys
1               5                   10                  15

Ala Leu Lys Ala Pro Gln His Phe Tyr Asn Ser Gln Pro Gly Lys Gly
            20                  25                  30

Tyr Val Thr Asp Met Gln His Tyr Gln Glu Met Tyr Gln Gln Ser Ile
        35                  40                  45

Asn Glu Pro Glu Lys Phe Phe Asp Lys Met Ala Lys Glu Tyr Leu His
    50                  55                  60

Trp Asp Ala Pro Tyr Thr Lys Val Gln Ser Gly Ser Leu Asn Asn Gly
65                  70                  75                  80

Asp Val Ala Trp Phe Leu Asn Gly Lys Leu Asn Ala Ser Tyr Asn Cys
                85                  90                  95

Val Asp Arg His Ala Phe Ala Asn Pro Asp Lys Pro Ala Leu Ile Tyr
            100                 105                 110

Glu Ala Asp Asp Glu Ser Asp Asn Lys Ile Ile Thr Phe Gly Glu Leu
        115                 120                 125

Leu Arg Lys Val Ser Gln Ile Ala Gly Val Leu Lys Ser Trp Gly Val
    130                 135                 140

Lys Lys Gly Asp Thr Val Ala Ile Tyr Leu Pro Met Ile Pro Glu Ala
145                 150                 155                 160

Val Ile Ala Met Leu Ala Val Ala Arg Ile Gly Ala Ile His Ser Val
                165                 170                 175

Val Phe Ala Gly Phe Ser Ala Gly Ser Leu Lys Asp Arg Val Val Asp
            180                 185                 190

Ala Asn Ser Lys Val Val Ile Thr Cys Asp Glu Gly Lys Arg Gly Gly
        195                 200                 205

Lys Thr Ile Asn Thr Lys Lys Ile Val Asp Glu Gly Leu Asn Gly Val
    210                 215                 220

Asp Leu Val Ser Arg Ile Leu Val Phe Gln Arg Thr Gly Thr Glu Gly
225                 230                 235                 240

Ile Pro Met Lys Ala Gly Arg Asp Tyr Trp Trp His Glu Glu Ala Ala
                245                 250                 255

Lys Gln Arg Thr Tyr Leu Pro Pro Val Ser Cys Asp Ala Glu Asp Pro
            260                 265                 270

Leu Phe Leu Leu Tyr Thr Ser Gly Ser Thr Gly Ser Pro Lys Gly Val
        275                 280                 285
```

```
Val His Thr Thr Gly Gly Tyr Leu Leu Gly Ala Ala Leu Thr Thr Arg
    290                 295                 300

Tyr Val Phe Asp Ile His Pro Glu Asp Val Leu Phe Thr Ala Gly Asp
305                 310                 315                 320

Val Gly Trp Ile Thr Gly His Thr Tyr Ala Leu Tyr Gly Pro Leu Thr
                325                 330                 335

Leu Gly Thr Ala Ser Ile Ile Phe Glu Ser Thr Pro Ala Tyr Pro Asp
            340                 345                 350

Tyr Gly Arg Tyr Trp Arg Ile Ile Gln Arg His Lys Ala Thr His Phe
        355                 360                 365

Tyr Val Ala Pro Thr Ala Leu Arg Leu Ile Lys Arg Val Gly Glu Ala
    370                 375                 380

Glu Ile Ala Lys Tyr Asp Thr Ser Ser Leu Arg Val Leu Gly Ser Val
385                 390                 395                 400

Gly Glu Pro Ile Ser Pro Asp Leu Trp Glu Trp Tyr His Glu Lys Val
                405                 410                 415

Gly Asn Lys Asn Cys Val Ile Cys Asp Thr Met Trp Gln Thr Glu Ser
            420                 425                 430

Gly Ser His Leu Ile Ala Pro Leu Ala Gly Ala Val Pro Thr Lys Pro
        435                 440                 445

Gly Ser Ala Thr Val Pro Phe Phe Gly Ile Asn Ala Cys Ile Ile Asp
    450                 455                 460

Pro Val Thr Gly Val Glu Leu Glu Gly Asn Asp Val Glu Gly Val Leu
465                 470                 475                 480

Ala Val Lys Ser Pro Trp Pro Ser Met Ala Arg Ser Val Trp Asn His
                485                 490                 495

His Asp Arg Tyr Met Asp Thr Tyr Leu Lys Pro Tyr Pro Gly His Tyr
            500                 505                 510

Phe Thr Gly Asp Gly Ala Gly Arg Asp His Asp Gly Tyr Tyr Trp Ile
        515                 520                 525

Arg Gly Arg Val Asp Asp Val Val Asn Val Ser Gly His Arg Leu Ser
    530                 535                 540

Thr Ser Glu Ile Glu Ala Ser Ile Ser Asn His Glu Asn Val Ser Glu
545                 550                 555                 560

Ala Ala Val Val Gly Ile Pro Asp Glu Leu Thr Gly Gln Thr Val Val
                565                 570                 575

Ala Tyr Val Ser Leu Lys Asp Gly Tyr Leu Gln Asn Asn Ala Thr Glu
            580                 585                 590

Gly Asp Ala Glu His Ile Thr Pro Asp Asn Leu Arg Arg Glu Leu Ile
        595                 600                 605

Leu Gln Val Arg Gly Glu Ile Gly Pro Phe Ala Ser Pro Lys Thr Ile
    610                 615                 620

Ile Leu Val Arg Asp Leu Pro Arg Thr Arg Ser Gly Lys Ile Met Arg
625                 630                 635                 640

Arg Val Leu Arg Lys Val Ala Ser Asn Glu Ala Glu Gln Leu Gly Asp
                645                 650                 655

Leu Thr Thr Leu Ala Asn Pro Glu Val Val Pro Ala Ile Ile Ser Ala
            660                 665                 670

Val Glu Asn Gln Phe Phe Ser Gln Lys Lys Lys
        675                 680
```

<210> SEQ ID NO 15
<211> LENGTH: 384

-continued

<212> TYPE: PRT
<213> ORGANISM: Saccharomyces cerevisiae

<400> SEQUENCE: 15

```
Met Thr Ala His Thr Asn Ile Lys Gln His Lys His Cys His Glu Asp
1               5                   10                  15

His Pro Ile Arg Arg Ser Asp Ser Ala Val Ser Ile Val His Leu Lys
            20                  25                  30

Arg Ala Pro Phe Lys Val Thr Val Ile Gly Ser Gly Asn Trp Gly Thr
        35                  40                  45

Thr Ile Ala Lys Val Ile Ala Glu Asn Thr Glu Leu His Ser His Ile
    50                  55                  60

Phe Glu Pro Glu Val Arg Met Trp Val Phe Asp Glu Lys Ile Gly Asp
65                  70                  75                  80

Glu Asn Leu Thr Asp Ile Ile Asn Thr Arg His Gln Asn Val Lys Tyr
                85                  90                  95

Leu Pro Asn Ile Asp Leu Pro His Asn Leu Val Ala Asp Pro Asp Leu
            100                 105                 110

Leu His Ser Ile Lys Gly Ala Asp Ile Leu Val Phe Asn Ile Pro His
        115                 120                 125

Gln Phe Leu Pro Asn Ile Val Lys Gln Leu Gln Gly His Val Ala Pro
    130                 135                 140

His Val Arg Ala Ile Ser Cys Leu Lys Gly Phe Glu Leu Gly Ser Lys
145                 150                 155                 160

Gly Val Gln Leu Leu Ser Ser Tyr Val Thr Asp Glu Leu Gly Ile Gln
                165                 170                 175

Cys Gly Ala Leu Ser Gly Ala Asn Leu Ala Pro Glu Val Ala Lys Glu
            180                 185                 190

His Trp Ser Glu Thr Thr Val Ala Tyr Gln Leu Pro Lys Asp Tyr Gln
        195                 200                 205

Gly Asp Gly Lys Asp Val Asp His Lys Ile Leu Lys Leu Leu Phe His
    210                 215                 220

Arg Pro Tyr Phe His Val Asn Val Ile Asp Asp Val Ala Gly Ile Ser
225                 230                 235                 240

Ile Ala Gly Ala Leu Lys Asn Val Val Ala Leu Ala Cys Gly Phe Val
                245                 250                 255

Glu Gly Met Gly Trp Gly Asn Asn Ala Ser Ala Ala Ile Gln Arg Leu
            260                 265                 270

Gly Leu Gly Glu Ile Ile Lys Phe Gly Arg Met Phe Phe Pro Glu Ser
        275                 280                 285

Lys Val Glu Thr Tyr Tyr Gln Glu Ser Ala Gly Val Ala Asp Leu Ile
    290                 295                 300

Thr Thr Cys Ser Gly Gly Arg Asn Val Lys Val Ala Thr Tyr Met Ala
305                 310                 315                 320

Lys Thr Gly Lys Ser Ala Leu Glu Ala Glu Lys Glu Leu Leu Asn Gly
                325                 330                 335

Gln Ser Ala Gln Gly Ile Ile Thr Cys Arg Glu Val His Glu Trp Leu
            340                 345                 350

Gln Thr Cys Glu Leu Thr Gln Glu Phe Pro Ile Ile Arg Gly Ser Leu
        355                 360                 365

Pro Asp Ser Leu Gln Gln Arg Pro His Gly Arg Pro Thr Gly Asp Asp
    370                 375                 380
```

<210> SEQ ID NO 16

<211> LENGTH: 391
<212> TYPE: PRT
<213> ORGANISM: Saccharomyces cerevisiae

<400> SEQUENCE: 16

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
```

385 390

<210> SEQ ID NO 17
<211> LENGTH: 2573
<212> TYPE: DNA
<213> ORGANISM: Artificial
<220> FEATURE:
<223> OTHER INFORMATION: GDP1 disruption

<400> SEQUENCE: 17
ggtacccccg ccttgcttct ctccccttcc ttttcttttt ccagttttcc ctattttgtc 60
cctttttccg cacaacaagt atcagaatgg gttcatcaaa tctatccaac ctaattcgca 120
cgtagactgg cttggtattg gcagtttcgt agttatatat atactaccat gagtgaaact 180
gttacgttac cttaaattct ttctcccttt aattttcttt tatcttactc tcctacataa 240
gacatcaaga aacaattgta tattgtacac cccccccctc cacaaacaca aatattgata 300
atataaagat gtctgctgct gctgatagat taaacttaac ttccggccac ttgaatctag 360
atgcatgctc gagcggccgc cagtgtgatg gatatctgca gaattcgccc ttttgggccc 420
tgtacaccta ggatccgtcg acactggatg gcggcgttag tatcgaatcg acagcagtat 480
agcgaccagc attcacatac gattgacgca tgatattact ttctgcgcac ttaacttcgc 540
atctgggcag atgatgtcga ggcgaaaaaa aatataaatc acgctaacat ttgattaaaa 600
tagaacaact acaatataaa aaaactatac aaatgacaag ttcttgaaaa caagaatctt 660
tttattgtca gtactgatta ttcctttgcc ctcggacgag tgctggggcg tcggtttcca 720
ctatcggcga gtacttctac acagccatcg gtccagacgg ccgcgcttct gcgggcgatt 780
tgtgtacgcc cgacagtccc ggctccggat cggacgattg cgtcgcatcg accctgcgcc 840
caagctgcat catcgaaatt gccgtcaacc aagctctgat agagttggtc aagaccaatg 900
cggagcatat acgcccggag ccgcggcgat cctgcaagct ccggatgcct ccgctcgaag 960
tagcgcgtct gctgctccat acaagccaac cacggcctcc agaagaagat gttggcgacc 1020
tcgtattggg aatccccgaa catcgcctcg ctccagtcaa tgaccgctgt tatgcggcca 1080
ttgtccgtca ggacattgtt ggagccgaaa tccgcgtgca cgaggtgccg gacttcgggg 1140
cagtcctcgg cccaaagcat cagctcatcg agagcctgcg cgacggacgc actgacggtg 1200
tcgtccatca cagtttgcca gtgatacaca tggggatcag caatcgcgca tatgaaatca 1260
cgccatgtag tgtattgacc gattccttgc ggtccgaatg ggccgaaccc gctcgtctgg 1320
ctaagatcgg ccgcagcgat cgcatccatg gcctccgcga ccggctgcag aacagcgggc 1380
agttcggttt caggcaggtc ttgcaacgtg acaccctgtg cacggcggga gatgcaatag 1440
gtcaggctct cgctgaattc cccaatgtca agcacttccg gaatcgggag cgcggccgat 1500
gcaaagtgcc gataaacata acgatctttg tagaaaccat cggcgcagct atttacccgc 1560
aggacatatc cacgccctcc tacatcgaag ctgaaagcac gagattcttc gccctccgag 1620
agctgcatca ggtcggagac gctgtcgaac ttttcgatca gaaacttctc gacagacgtc 1680
gcggtgagtt caggcttttt acccatggtt gtttatgttc ggatgtgatg tgagaactgt 1740
atcctagcaa gattttaaaa ggaagtatat gaaagaagaa cctcagtggc aaatcctaac 1800
cttttatatt tctctacagg ggcgcggcgt ggggacaatt cacgcgtctg tgaggggagc 1860
gtttccctgc tcgcaggtct gcagcgagga gccgtaattt ttgcttcgcg ccgtgcggcc 1920
atcaaaatgt atggatgcaa atgattatac atggggatgt atgggctaaa tgtacgggcg 1980
acagtcacat catgcccctg agctgcgcac gtcaagactg tcaaggaggg tattctgggc 2040

```
ctccatgtcg ctggccgggt gacccggcgg ggacgaggcc ttaagttcga acgtacggag   2100

ttgttgaatg gccaatccgc tcaaggttta attacctgca aagaagttca cgaatggttg   2160

gaaacatgtg gctctgtcga agacttccca ttatttgaag ccgtatacca aatcgtttac   2220

aacaactacc caatgaagaa cctgccggac atgattgaag aattagatct acatgaagat   2280

tagatttatt ggagaaagat aacatatcat actttccccc actttttttcg aggctcttct   2340

atatcatatt cataaattag cattatgtca tttctcataa ctactttatc acgttagaaa   2400

ttacttatta ttattaaatt aatacaaaat ttagtaacca aataaatata aataaatatg   2460

tatatttaaa ttttaaaaaa aaaatcctat agagcaaaag gattttccat tataatatta   2520

gctgtacacc tcttccgcat tttttgaggg tggttacaac accactcggt acc          2573
```

<210> SEQ ID NO 18
<211> LENGTH: 2058
<212> TYPE: DNA
<213> ORGANISM: Artificial
<220> FEATURE:
<223> OTHER INFORMATION: GPD2 disruption

<400> SEQUENCE: 18

```
agatcttttg cggcgaggtg ccgatgggtt gctgaggggga agagtgttta gcttacggac     60

ctattgccat tgttattccg attaatctat tgttcagcag ctcttctcta ccctgtcatt    120

ctagtatttt tttttttttt ttttggtttt acttttttttt cttcttgcct ttttttcttg    180

ttactttttt tctagttttt tttccttcca ctaagctttt tccttgattt atccttgggt    240

tcttctttct actcctttag atttttttttt tatatattaa tttttaagtt tatgtatttt    300

ggtagattca attctctttc cctttccttt tccttcgctc cccttcctta tcaatgcttg    360

ctgtcagaag attaacaaga tacacattcc ttaaggcctc gtccccgccg ggtcacccgg    420

ccagcgacat ggaggcccag aataccctcc ttgacagtct tgacgtgcgc agctcagggg    480

catgatgtga ctgtcgcccg tacatttagc ccatacatcc ccatgtataa tcatttgcat    540

ccatacattt tgatggccgc acggcgcgaa gcaaaaaatta cggctcctcg ctgcagacct    600

gcgagcaggg aaacgctccc ctcacagacg cgttgaattg tccccacgcc gcgcccctgt    660

agagaaatat aaaaggttag gatttgccac tgaggttctt ctttcatata cttcctttta    720

aaatcttgct aggatacagt tctcacatca catccgaaca taaacaacca tgtaaaatga    780

ccactcttga cgacacggct taccggtacc gcaccagtgt cccgggggac gccgaggcca    840

tcgaggcact ggatgggtcc ttcaccaccg acaccgtctt ccgcgtcacc gccaccgggg    900

acggcttcac cctgcgggag gtgccggtgg acccgcccct gaccaaggtg ttccccgacg    960

acgaatcgga cgacgaatcg gacgccgggg aggacggcga cccggactcc cggacgttcg   1020

tcgcgtacgg ggacgacggc gacctggcgg gcttcgtggt cgtctcgtac tccggctgga   1080

accgccggct gaccgtcgag gacatcgagg tcgccccgga gcaccggggg cacggggtcg   1140

ggcgcgcgtt gatggggctc gcgacggagt tcgcccgcga gcggggcgcc gggcacctct   1200

ggctggaggt caccaacgtc aacgcaccgg cgatccacgc gtaccggcgg atggggttca   1260

ccctctgcgg cctggacacc gccctgtacg acggcaccgc ctcggacggc gagcaggcgc   1320

tctacatgag catgccctgc ccctagtact gacaataaaa agattcttgt tttcaagaac   1380

ttgtcatttg tatagttttt ttatattgta gttgttctat tttaatcaaa tgttagcgtg   1440

atttatattt tttttcgcct cgacatcatc tgcccagatg cgaagttaag tgcgcagaaa   1500
```

gtaatatcat gcgtcaatcg tatgtgaatg ctggtcgcta tactgctgtc gattcgatac 1560
taacgccgcc atccagtgtc gacggatcct aggtgtacag ggcccaaaag ggcgaattct 1620
gcagatatcc atcacactgg cggccgctcg aggatagtct acaacaacgt ccgcatggaa 1680
gacctaccgg agatgattga agagctagac atcgatgacg aatagacact ctcccccccc 1740
ctccccctct gatctttcct gttgcctctt tttcccccaa ccaatttatc attatacaca 1800
agttctacaa ctactactag taacattact acagttatta taattttcta ttctcttttt 1860
ctttaagaat ctatcattaa cgttaatttc tatatataca taactaccat tatacacgct 1920
attatcgttt acatatcaca tcaccgttaa tgaaagatac gacaccctgt acactaacac 1980
aattaaataa tcgccataac cttttctgtt atctatagcc cttaaagctg tttcttcgag 2040
ctttttcact gcagatct 2058

<210> SEQ ID NO 19
<211> LENGTH: 816
<212> TYPE: DNA
<213> ORGANISM: Saccharomyces cerevisiae

<400> SEQUENCE: 19
ccatatgatc atgtgtcgtc gcacacatat atatatgcct gtatgtgtca gcactaaagt 60
tgcctggcca tccacgctat atatacacgc ctggcggatc tgctcgagga ttgcctacgc 120
gtgggcttga tccaccaacc aacgctcgcc aaatgaactg gcgctttggt cttctgccat 180
cgtccgtaaa ccccggccaa agagaccgga aagatcggtg aaaacatctt gatcttgctc 240
ccgggaattt tagattcagg taggaaattg attacatcaa tactgttacc ctgaatcata 300
ttcgacgatg tcgtctcaca cggaaatata attcatttct tggttttcca aaaaaatttt 360
catttttttt cacttttttg tttcgtcctc cttttttttt tttttttttt attttttttc 420
ctgtgttcac cttttttttt ttcagttgac atctttctgc attcttttct gtgttttttt 480
tttttttttt cgtttttcca ttgttcgttc gttgcctgtt ttttcgccct attgttctcg 540
agcctaaaaa ttttttcctt tcctgctttc ctttcttcgt tcaaagtttc ctattccatt 600
gttctctttg gtaaactcat tgttgtcgga actcagatat attcaggtca atttactgta 660
cttcaattga cttttttctt gaaatttcaa cttgcctttt caacttgttc ttctttttta 720
atcttattct acactttagt tcccttacct tgttcctaat tattgtctag caaaaagaaa 780
acatacacct atttcattca cacactgcag aaaatg 816

<210> SEQ ID NO 20
<211> LENGTH: 12350
<212> TYPE: DNA
<213> ORGANISM: Artificial
<220> FEATURE:
<223> OTHER INFORMATION: pRN500

<400> SEQUENCE: 20
tcgatgataa gctgtcaaag atgagaatta attccacgga ctatagacta tactagatac 60
tccgtctact gtacgataca cttccgctca ggtccttgtc ctttaacgag gccttaccac 120
tcttttgtta ctctattgat ccagctcagc aaaggcagtg tgatctaaga ttctatcttc 180
gcgatgtagt aaaactagct agaccgagaa agagactaga aatgcaaaag gcacttctac 240
aatggctgcc atcattatta tccgatgtga cgctgcagct tctcaatgat attcgaatac 300
gctttgagga gatacagcct aatatccgac aaactgtttt acagatttac gatcgtactt 360
gttacccatc attgaatttt gaacatccga acctgggagt tttccctgaa acagatagta 420

-continued

```
tatttgaacc tgtataataa tatatagtct agcgctttac ggaagacaat gtatgtattt    480
cggttcctgg agaaactatt gcatctattg cataggtaat cttgcacgtc gcatccccgg    540
ttcattttct gcgtttccat cttgcacttc aatagcatat ctttgttaac gaagcatctg    600
tgcttcattt tgtagaacaa aaatgcaacg cgagagcgct aatttttcaa acaaagaatc    660
tgagctgcat ttttacagaa cagaaatgca acgcgaaagc gctattttac caacgaagaa    720
tctgtgcttc atttttgtaa aacaaaaatg caacgcgacg agagcgctaa tttttcaaac    780
aaagaatctg agctgcattt ttacagaaca gaaatgcaac gcgagagcgc tattttacca    840
acaaagaatc tatacttctt ttttgttcta caaaaatgca tcccgagagc gctatttttc    900
taacaaagca tcttagatta cttttttct cctttgtgcg ctctataatg cagtctcttg    960
ataacttttt gcactgtagg tccgttaagg ttagaagaag gctactttgg tgtctatttt   1020
ctcttccata aaaaaagcct gactccactt cccgcgttta ctgattacta gcgaagctgc   1080
gggtgcattt tttcaagata aaggcatccc cgattatatt ctataccgat gtggattgcg   1140
catactttgt gaacagaaag tgatagcgtt gatgattctt cattggtcag aaaattatga   1200
acggtttctt ctattttgtc tctatatact acgtatagga aatgtttaca ttttcgtatt   1260
gttttcgatt cactctatga atagttctta ctacaatttt tttgtctaaa gagtaatact   1320
agagataaac ataaaaaatg tagaggtcga gtttagatgc aagttcaagg agcgaaaggt   1380
ggatgggtag gttatatagg gatatagcac agagatatat agcaaagaga tacttttgag   1440
caatgtttgt ggaagcggta ttcgcaatgc cggctttccc cgtcaagctc taaatcgggg   1500
gctcccttta gggttccgat ttagtgcttt acggcacctc gaccccaaaa aacttgatta   1560
gggtgatggt tcacgtagtg ggccatcgcc ctgatagacg gtttttcgcc ctttgacgtt   1620
ggagtccacg ttctttaata gtggactctt gttccaaact ggaacaacac tcaaccctat   1680
ctcggtctat tcttttgatt tataagggat tttgccgatt tcggcctatt ggttaaaaaa   1740
tgagctgatt taacaaaaat ttaacgcgaa ttttaacaaa atattaacgt ttacaatttc   1800
ctgatgcggt attttctcct tacgcatctg tgcggtattt cacaccgcag ggtaataact   1860
gatataatta aattgaagct ctaatttgtg agtttagtat acatgcattt acttataata   1920
cagtttttta gttttgctgg ccgcatcttc tcaaatatgc ttcccagcct gcttttctgt   1980
aacgttcacc ctctacctta gcatcccttc cctttgcaaa tagtcctctt ccaacaataa   2040
taatgtcaga tcctgtagag accacatcat ccacggttct atactgttga cccaatgcgt   2100
ctcccttgtc atctaaaccc acaccgggtg tcataatcaa ccaatcgtaa ccttcatctc   2160
ttccacccat gtctctttga gcaataaagc cgataacaaa atctttgtcg ctcttcgcaa   2220
tgtcaacagt acccttagta tattctccag tagataggga gcccttgcat gacaattctg   2280
ctaacatcaa aaggcctcta ggttcctttg ttacttcttc tgccgcctgc ttcaaaccgc   2340
taacaatacc tgggcccacc acaccgtgtg cattcgtaat gtctgcccat tctgctattc   2400
tgtatacacc cgcagagtac tgcaatttga ctgtattacc aatgtcagca aattttctgt   2460
cttcgaagag taaaaaattg tacttggcgg ataatgcctt tagcggctta actgtgccct   2520
ccatggaaaa atcagtcaag atatccacat gtgtttttag taaacaaatt ttgggaccta   2580
atgcttcaac taactccagt aattccttgg tggtacgaac atccaatgaa gcacacaagt   2640
ttgtttgctt ttcgtgcatg atattaaata gcttggcagc aacaggacta ggatgagtag   2700
cagcacgttc cttatatgta gctttcgaca tgatttatct tcgtttcctg caggtttttg   2760
```

-continued

```
ttctgtgcag ttgggttaag aatactgggc aatttcatgt ttcttcaaca ctacatatgc   2820
gtatatatac caatctaagt ctgtgctcct tccttcgttc ttccttctgt tcggagatta   2880
ccgaatcaaa aaaatttcaa agaaaccgaa atcaaaaaaa agaataaaaa aaaaatgatg   2940
aattgaattg aaaagcgtgg tgcactctca gtacaatctg ctctgatgcc gcatagttaa   3000
gccagccccg acacccgcca acacccgctg acgcgccctg acgggcttgt ctgctcccgg   3060
catccgctta cagacaagct gtgaccgtct ccgggagctg catgtgtcag aggttttcac   3120
cgtcatcacc gaaacgcgcg agacgaaagg gcctcgtgat acgcctattt ttataggtta   3180
atgtcatgat aataatggtt tcttagacgt caggtggcac ttttcgggga aatgtgcgcg   3240
gaacccctat ttgtttattt ttctaaatac attcaaatat gtatccgctc atgagacaat   3300
aaccctgata aatgcttcaa taatattgaa aaaggaagag tatgagtatt caacatttcc   3360
gtgtcgccct tattcccttt tttgcggcat tttgccttcc tgtttttgct cacccagaaa   3420
cgctggtgaa agtaaaagat gctgaagatc agttgggtgc acgagtgggt tacatcgaac   3480
tggatctcaa cagcggtaag atccttgaga gttttcgccc cgaagaacgt tttccaatga   3540
tgagcacttt taaagttctg ctatgtggcg cggtattatc ccgtattgac gccgggcaag   3600
agcaactcgg tcgccgcata cactattctc agaatgactt ggttgagtac tcaccagtca   3660
cagaaaagca tcttacggat ggcatgacag taagagaatt atgcagtgct gccataacca   3720
tgagtgataa cactgcggcc aacttacttc tgacaacgat cggaggaccg aaggagctaa   3780
ccgctttttt tcacaacatg ggggatcatg taactcgcct tgatcgttgg gaaccggagc   3840
tgaatgaagc cataccaaac gacgagcgtg acaccacgat gcctgtagca atggcaacaa   3900
cgttgcgcaa actattaact ggcgaactac ttactctagc ttcccggcaa caattaatag   3960
actggatgga ggcggataaa gttgcaggac cacttctgcg ctcggccctt ccggctggct   4020
ggtttattgc tgataaatct ggagccggtg agcgtgggtc tcgcggtatc attgcagcac   4080
tggggccaga tggtaagccc tcccgtatcg tagttatcta cacgacgggc agtcaggcaa   4140
ctatggatga acgaaataga cagatcgctg agataggtgc ctcactgatt aagcattggt   4200
aactgtcaga ccaagtttac tcatatatac tttagattga tttaaaactt catttttaat   4260
ttaaaaggat ctaggtgaag atcctttttg ataatctcat gaccaaaatc ccttaacgtg   4320
agttttcgtt ccactgagcg tcagaccccg tagaaaagat caaaggatct tcttgagatc   4380
cttttttttct gcgcgtaatc tgctgcttgc aaacaaaaaa accaccgcta ccagcggtgg   4440
tttgtttgcc ggatcaagag ctaccaactc tttttccgaa ggtaactggc ttcagcagag   4500
cgcagatacc aaatactgtc cttctagtgt agccgtagtt aggccaccac ttcaagaact   4560
ctgtagcacc gcctacatac ctcgctctgc taatcctgtt accagtggct gctgccagtg   4620
gcgataagtc gtgtcttacc gggttggact caagacgata gttaccggat aaggcgcagc   4680
ggtcgggctg aacggggggt tcgtgcacac agcccagctt ggagcgaacg acctacaccg   4740
aactgagata cctacagcgt gagcattgag aaagcgccac gcttcccgaa gggagaaagg   4800
cggacaggta tccggtaagc ggcagggtcg gaacaggaga gcgcacgagg gagcttccag   4860
ggggaaacgc ctggtatctt tatagtcctg tcgggtttcg ccacctctga cttgagcgtc   4920
gatttttgtg atgctcgtca ggggggcgga gcctatggaa aaacgccagc aacgcggcct   4980
ttttacggtt cctggccttt tgctggcctt ttgctcacat gttctttcct gcgttatccc   5040
ctgattctgt ggataaccgt attaccgcct ttgagtgagc tgataccgct cgccgcagcc   5100
gaacgaccga gcgcagcgag tcagtgagcg aggaagcgga agagcgccca atacgcaaac   5160
```

```
cgcctctccc cgcgcgttgg ccgattcatt aatgcagctg gcacgacagg tttcccgact   5220
ggaaagcggg cagtgagcgc aacgcaatta atgtgagtta cctcactcat taggcacccc   5280
aggctttaca ctttatgctt ccggctccta tgttgtgtgg aattgtgagc ggataacaat   5340
ttcacacagg aaacagctat gaccatgatt acgccaagct cggaattaac cctcactaaa   5400
gggaacaaaa gctgggtacc gggccccccc tcgaccggtc ccacacacca tagcttcaaa   5460
atgtttctac tcctttttta ctcttccaga ttttctcgga ctccgcgcat cgccgtacca   5520
cttcaaaaca cccaagcaca gcatactaaa tttcccctct ttcttcctct agggtgtcgt   5580
taattacccg tactaaaggt ttggaaaaga aaaaagagac cgcctcgttt ctttttcttc   5640
gtcgaaaaag gcaataaaaa tttttatcac gtttcttttt cttgaaaatt tttttttttg   5700
atttttttct ctttcgatga cctcccattg atatttaagt taataaacgg tcttcaattt   5760
ctcaagtttc agtttcattt ttcttgttct attacaactt tttttacttc ttgctcatta   5820
gaaagaaagc atagcaatct aatctaagct gcagaagctt aaaatgtcgc cctctgccgt   5880
acaatcatca aaactagaag aacagtcaag tgaaattgac aagttgaaag caaaaatgtc   5940
ccagtctgcc gccactgcgc agcagaagaa ggaacatgag tatgaacatt tgacttcggt   6000
caagatcgtg ccacaacggc ccatctcaga tagactgcag cccgcaattg ctacccacta   6060
ttctccacac ttggacgggt tgcaggacta tcagcgcttg cacaaggagt ctattgaaga   6120
ccctgctaag ttcttcggtt ctaaagctac ccaatttta aactggtcta agccattcga   6180
taaggtgttc atcccagacc ctaaaacggg caggccctcc ttccagaaca atgcatggtt   6240
cctcaacggc caattaaacg cctgttacaa ctgtgttgac agacatgcct tgaagactcc   6300
taacaagaaa gccattattt tcgaaggtga cgagcctggc caaggctatt ccattaccta   6360
caaggaacta cttgaagaag tttgtcaagt ggcacaagtg ctgacttact ctatgggcgt   6420
tcgcaagggc gatactgttg ccgtgtacat gcctatggtc ccagaagcaa tcataacctt   6480
gttggccatt tcccgtatcg gtgccattca ctccgtagtc tttgccgggt tttcttccaa   6540
ctccttgaga gatcgtatca acgatgggga ctctaaagtt gtcatcacta cagatgaatc   6600
caacagaggt ggtaaagtca ttgagactaa aagaattgtt gatgacgcgc taagagagac   6660
cccaggcgtg agacacgtct tggtttatag aaagaccaac aatccatctg ttgctttcca   6720
tgcccccaga gatttggatt gggcaacaga aaagaagaaa tacaagacct actatccatg   6780
cacacccgtt gattctgagg atccattatt cttgttgtat acgtctggtt ctactggtgc   6840
ccccaagggt gttcaacatt ctaccgcagg ttacttgctg ggagctttgt tgaccatgcg   6900
ctacactttt gacactcacc aagaagacgt tttcttcaca gctggagaca ttggctggat   6960
tacaggccac acttatgtgg tttatggtcc cttactatat ggttgtgcca ctttggtctt   7020
tgaagggact cctgcgtacc caaattactc ccgttattgg gatattattg atgaacacaa   7080
agtcacccaa ttttatgttg cgccaactgc tttgcgtttg ttgaaaagag ctggtgattc   7140
ctacatcgaa aatcattcct taaaatcttt gcgttgcttg ggttcggtcg gtgagccaat   7200
tgctgctgaa gtttgggagt ggtactctga aaaaataggt aaaaatgaaa tccccattgt   7260
agacacctac tggcaaacag aatctggttc gcatctggtc accccgctgg ctggtggtgt   7320
tacaccaatg aaaccgggtt ctgcctcatt ccccttcttc ggtattgatg cagttgttct   7380
tgaccctaac actggtgaag aacttaacac cagccacgca gagggtgtcc ttgccgtcaa   7440
agctgcatgg ccatcatttg caagaactat ttggaaaaat catgataggt atctagacac   7500
```

-continued ttatttgaac ccttaccctg gctactattt cactggtgat ggtgctgcaa aggataagga 7560
tggttatatc tggattttgg gtcgtgtaga cgatgtggtg aacgtctctg gtcaccgtct 7620
gtctaccgct gaaattgagg ctgctattat cgaagatcca attgtggccg agtgtgctgt 7680
tgtcggattc aacgatgact tgactggtca agcagttgct gcatttgtgg tgttgaaaaa 7740
caaatctagt tggtccaccg caacagatga tgaattacaa gatatcaaga agcatttggt 7800
ctttactgtt agaaaagaca tcgggccatt tgccgcacca aaattgatca ttttagtgga 7860
tgacttgccc aagacaagat ccggcaaaat tatgagacgt attttaagaa aaatcctagc 7920
aggagaaagt gaccaactag gcgacgtttc tacattgtca aaccctggca ttgttagaca 7980
tctaattgat tcggtcaagt tgtaacttaa gcgcgcgaat ttcttatgat ttatgatttt 8040
tattattaaa taagttataa aaaaaataag tgtatacaaa ttttaaagtg actcttaggt 8100
tttaaaacga aaattcttat tcttgagtaa ctctttcctg taggtcaggt tgctttctca 8160
ggtatagcat gaggtcgctc ttattgacca cacctctacc ggcatgccga gcaaatgcct 8220
gcaaatcgct ccccatttca cccaattgta gatatgctaa ctccagcaat gagttgatga 8280
atctcggtgt gtattttatg tcctcagagg acaacacctg ttgtaatcgt tcttccacac 8340
gtacgtttta aacagttgat gagaaccttt ttcgcaagtt caaggtgctc taatttttaa 8400
aatttttact tttcgcgaca caataaagtc ttcacgacgc taaactatta gtgcacataa 8460
tgtagttact tggacgctgt tcaataatgt ataaaattta tttcctttgc attacgtaca 8520
ttatataacc aaatcttaaa aatatagaaa tatgatatgt gtataataat ataagcaaaa 8580
tttacgtatc tttgcttata atatagcttt aatgttcttt aggtatatat ttaagagcga 8640
tttgtctcga cttatttctt tttttgagag aaaaattggt tctctacagc agaaatgatg 8700
gcaggtacaa cttctgggtt ggccaaagta gttaggtcac ctagctgttc ggcttcgtta 8760
gaagcaacct ttcttagaac tcttctcata atctttcctg accttgttct tggtagatct 8820
ctaactagaa taatggtttt tggtgaggcg aaaggaccaa tctcacccct aacttgtaag 8880
atcaattctc tacgtaaatt atctggtgtg atgtgttctg catcaccttc agtagcgttg 8940
ttttgtagat aaccatcttt tagggaaaca tatgcaacga cggtttgacc ggtcaattca 9000
tctggaatac cgacaacagc agcttccgag acgttttcgt gatttgagat agatgcttca 9060
atttctgatg tggataatct atgaccggaa acatttacaa cgtcgtcaac tctacccctg 9120
atccagtagt aaccatcatg atctctacca gcaccatcac ctgtgaaata gtgaccagga 9180
taaggtttca agtaagtatc catgtaacgg tcgtggtggt tccaaacaga tctagccatt 9240
gatggccatg gtgatttaac ggcaaggaca ccttcgacat cattaccttc taattccaca 9300
cctgtaacag ggtcaatgat acaagcgtta ataccaaaga atggcacggt agcagaacca 9360
ggttttgttg ggacagcacc tgccaaagga gcaattaaat gagaaccaga ctctgtttgc 9420
cacatagtgt cacaaatgac acagtttttg ttacccactt tttcatgata ccattcccat 9480
aagtctggag agattggttc accgacggaa cccaagacac gtaatgagga agtgtcatat 9540
ttggcaattt cggcttcacc tacacgtttg attaatctta aagcagttgg agccacatag 9600
aaatgggtag ccttgtgacg ttggataatt ctccaatatc taccataatc tgggtaggca 9660
ggagtggatt cgaaaattat tgaggcggta cccaaggtta atggaccata tagagcatag 9720
gtgtgacccg tgatccagcc gacgtcaccg gcagtgaaga gaacatcttc tgggtgaata 9780
tcaaaaacgt atctagttgt taaagcggca cctaataaat aaccacctgt agtgtgaacg 9840
acaccctttg gagaaccagt ggaaccggaa gtgtataata aaaatagagg atcttcagcg 9900

```
tcacatgaaa caggaggtag gtaagttctc tgcttagcgg cctcctcatg ccaccagtaa    9960
tctctaccgg ccttcattgg aataccttca gtaccagttc tttggaaaac caagatacgg   10020
gaaaccaaat cgactccgtt caaaccttcg tcaacaattt ttttagtgtt gatggtctta   10080
ccacctcttt taccttcatc acaagtgatg accactttag aattagcgtc aacgacacga   10140
tctttcaacg aaccagcgga gaacccagca aagacaacag agtgaatagc accaatacga   10200
gccacagcca acatagcaat gaccgcttct ggaatcattg gcaaatagat agccactgtg   10260
tcacctttct taacgcccca gctttttaag acaccagcga tttgggaaac ttttctgagt   10320
aattcaccaa atgtgatgat tttgttgtcg gattcgtcat cagcttcata gatcaaagct   10380
ggcttgtcgg gattagcaaa ggcatgtctg tcaacacaat tgtatgatgc attcaattta   10440
ccgttcaaaa accatgcaac atcaccattg ttcaatgaac cagattgaac tttggtgtat   10500
ggagcatccc aatgcaagta ttccttagcc atcttatcaa agaatttttc tggctcattg   10560
atagattgtt gatacatttc ttgataatgt tgcatatcag taacgtaacc cttgccgggt   10620
tggctgttgt aaaaatgttg aggagcctta agagccttta cgttgtgagc ttcataaact   10680
actttatgtt ccttgattgt cattttctgc agtctagata tatttgttgt aaaaagtaga   10740
taattacttc cttgatgatc tgtaaaaaag agaaaaagaa agcatctaag aacttgaaaa   10800
actacgaatt agaaaagacc aaatatgtat ttcttgcatt gaccaattta tgcaagttta   10860
tatatatgta aatgtaagtt tcacgaggtt ctactaaact aaaccacccc cttggttaga   10920
agaaaagagt gtgtgagaac aggctgttgt tgtcacacga ttcggacaat tctgtttgaa   10980
agagagagag taacagtacg atcgaacgaa ctttgctctg gagatcacag tgggcatcat   11040
agcatgtggt actaaaccct ttcccgccat tccagaacct tcgattgctt gttacaaaac   11100
ctgtgagccg tcgctaggac cttgttgtgt gacgaaattg gaagctgcaa tcaataggaa   11160
gacaggaagt cgagcgtgtc tgggtttttt cagttttgtt ctttttgcaa acaaatcacg   11220
agcgacggta atttctttct cgataagagg ccacgtgctt tatgagggta acatcaattc   11280
aagaaggagg gaaacacttc ctttttctgg ccctgataat agtatgaggg tgaagccaaa   11340
ataaaggatt cgcgcccaaa tcggcatctt taaatgcagg tatgcgatag ttcctcactc   11400
tttccttact cacgagtaat tcttgcaaat gcctattatg cagatgttat aatatctgtg   11460
cgtcttgagt tgaagagctc gagactagat gcatgctcga gcggccgcca gtgtgatgga   11520
tatctgcaga attcgccctt ttgggccctg tacacctagg atccgtcgac actggatggc   11580
ggcgttagta tcgaatcgac agcagtatag cgaccagcat tcacatacga ttgacgcatg   11640
atattacttt ctgcgcactt aacttcgcat ctgggcagat gatgtcgagg cgaaaaaaaa   11700
tataaatcac gctaacattt gattaaaata gaacaactac aatataaaaa aactatacaa   11760
atgacaagtt cttgaaaaca agaatctttt tattgtcagt actgattaga aaaactcatc   11820
gagcatcaaa tgaaactgca atttattcat atcaggatta tcaataccat atttttgaaa   11880
aagccgtttc tgtaatgaag gagaaaactc accgaggcag ttccatagga tggcaagatc   11940
ctggtatcgg tctgcgattc cgactcgtcc aacatcaata caacctatta atttcccctc   12000
gtcaaaaata aggttatcaa gtgagaaatc accatgagtg acgactgaat ccggtgagaa   12060
tggcaaaagc ttatgcattt ctttccagac ttgttcaaca ggccagccat tacgctcgtc   12120
atcaaaatca ctcgcatcaa ccaaaccgtt attcattcgt gattgcgcct gagcgagacg   12180
aaatacgcga tcgctgttaa aaggacaatt acaaacagga atcgaatgca accggcgcag   12240
```

gaacactgcc agcgcatcaa caatattttc acctgaatca ggatattctt ctaatacctg 12300
gaatgctgtt ttgccgggga tcgcagtggt gagtaaccat gcatcatcag 12350

<210> SEQ ID NO 21
<211> LENGTH: 1120
<212> TYPE: DNA
<213> ORGANISM: Artificial
<220> FEATURE:
<223> OTHER INFORMATION: nucleotide seqeunce encoding E.coli gldA codon-optimised for yeast

<400> SEQUENCE: 21
ctgcagaaaa tggacagaat catccaatct ccaggtaagt acatccaagg tgctgacgtt 60
atcaacagat tgggtgaata cttgaagcca ttggctgaaa gatggttggt tgttggtgac 120
aagttcgttt tgggtttcgc tcaatctacc gttgaaaagt ctttcaagga cgctggtttg 180
gttgttgaaa tcgctccatt cggtggtgaa tgttctcaaa acgaaatcga cagattgaga 240
ggtatcgctg aaaccgctca atgtggtgct atcttgggta tcggtggtgg taagaccttg 300
gacaccgcta aggctttggc tcacttcatg ggtgttccag ttgctatcgc tccaaccatc 360
gcttctaccg acgctccatg ttctgctttg tctgttatct acaccgacga aggtgaattc 420
gacagatact tgttgttgcc aaacaaccca aacatggtta tcgttgacac caagatcgtt 480
gctggtgctc cagctagatt gttggcagct ggtatcggtg acgctttggc tacctggttc 540
gaagctagag cttgttctag atctggtgct accaccatgg ctggtggtaa gtgtacccaa 600
gctgctttgg ctttggctga attgtgttac aacaccttgt tggaagaagg tgaaaaggct 660
atgttggctg ctgaacaaca cgttgttacc ccagctttgg aaagagttat cgaagctaac 720
acctacttgt ctggtgttgg tttcgaatct ggtggtttgg ctgctgctca cgctgttcac 780
aacggtttga ccgctatccc agacgctcac cactactacc acggtgaaaa ggttgctttc 840
ggtaccttga cccaattggt tttggaaaac gctccagttg aagaaatcga aaccgttgct 900
gctttgtctc acgctgttgg tttgccaatc accttggctc aattggacat caaggaagac 960
gttccagcta agatgagaat cgttgctgaa gctgcttgtg ctgaaggtga aaccatccac 1020
aacatgccag gtggtgctac cccagaccaa gtttacgctg ctttgttggt tgctgaccaa 1080
tacggtcaaa gattcctaca agaatgggaa taaggcgcgc 1120

<210> SEQ ID NO 22
<211> LENGTH: 1450
<212> TYPE: DNA
<213> ORGANISM: Artificial
<220> FEATURE:
<223> OTHER INFORMATION: DAK1 PCR fragment

<400> SEQUENCE: 22
tctagaaaat gtccgctaaa tcgtttgaag tcacagatcc agtcaattca agtctcaaag 60
ggtttgccct tgctaacccc tccattacgc tggtccctga agaaaaaatt ctcttcagaa 120
agaccgattc cgacaagatc gcattaattt ctggtggtgg tagtggacat gaacctacac 180
acgccggttt cattggtaag ggtatgttga gtggcgccgt ggttggcgaa atttttgcat 240
ccccttcaac aaaacagatt ttaaatgcaa tccgtttagt caatgaaaat gcgtctggcg 300
ttttattgat tgtgaagaac tacacaggtg atgttttgca ttttggtctg tccgctgaga 360
gagcaagagc cttgggtatt aactgccgcg ttgctgtcat aggtgatgat gttgcagttg 420
gcagagaaaa gggtggtatg gttggtagaa gagcattggc aggtaccgtt ttggttcata 480

-continued

```
agattgtagg tgccttcgca gaagaatatt ctagtaagta tggcttagac ggtacagcta    540
aagtggctaa aattatcaac gacaatttgg tgaccattgg atcttcttta gaccattgta    600
aagttcctgg caggaaattc gaaagtgaat taaacgaaaa acaaatggaa ttgggtatgg    660
gtattcataa cgaacctggt gtgaaagttt tagaccctat tccttctacc gaagacttga    720
tctccaagta tatgctacca aaactattgg atccaaacga taaggataga gcttttgtaa    780
agtttgatga agatgatgaa gttgtcttgt tagttaacaa tctcggcggt gtttctaatt    840
ttgttattag ttctatcact tccaaaacta cggatttctt aaaggaaaat tacaacataa    900
ccccggttca aacaattgct ggcacattga tgacctcctt caatggtaat gggttcagta    960
tcacattact aaacgccact aaggctacaa aggctttgca atctgatttt gaggagatca   1020
aatcagtact agacttgttg aacgcattta cgaacgcacc gggctggcca attgcagatt   1080
ttgaaaagac ttctgcccca tctgttaacg atgacttgtt acataatgaa gtaacagcaa   1140
aggccgtcgg tacctatgac tttgacaagt ttgctgagtg gatgaagagt ggtgctgaac   1200
aagttatcaa gagcgaaccg cacattacgg aactagacaa tcaagttggt gatggtgatt   1260
gtggttacac tttagtggca ggagttaaag gcatcaccga aaaccttgac aagctgtcga   1320
aggactcatt atctcaggcg gttgcccaaa tttcagattt cattgaaggc tcaatgggag   1380
gtacttctgg tggtttatat tctattcttt tgtcgggttt ttcacacgga ttaattcagg   1440
tttgtaaatc                                                          1450
```

<210> SEQ ID NO 23
<211> LENGTH: 1698
<212> TYPE: DNA
<213> ORGANISM: Artificial
<220> FEATURE:
<223> OTHER INFORMATION: GUP1 PCR fragment

<400> SEQUENCE: 23

```
gaattcaaaa tgtcgctgat cagcatcctg tctcccctaa ttacttccga gggcttagat     60
tcaagaatca aaccttcacc aaaaaaggat gcctctacta ccactaagcc atcactatgg    120
aaaactactg agttcaaatt ctactacatt gcatttctgg tcgtggttcc cttgatgttc    180
tatgctgggt tacaagctag ttcgcccgaa aatccaaact atgcaagata cgaacgtctc    240
ctatctcaag gttggttatt tggcagaaaa gtagacaata gtgattctca atataggttt    300
ttcagggaca attttgcgct attgtcagtt ttaatgctag tccacacttc tataaaacgc    360
attgtacttt attcaacaaa tatcactaaa ttgaggtttg atctgatatt tggtttgatc    420
tttttagtgg ccgctcatgg tgtcaattcg ataagaattt tagcccatat gctaatttta    480
tatgccatcg cccatgtact aaagaacttt agaagaatag ccaccatcag catttggatt    540
tatggtattt ctacgctttt tattaacgac aacttcagag catatccatt tggtaatatt    600
tgctcttttt taagcccatt ggaccattgg tatagaggta tcattccaag atgggatgtc    660
tttttcaatt ttactctttt gagagtctta agttacaact tggacttctt agagaggtgg    720
gagaatttac aaaagaagaa aagtccatcc tatgaatcaa aagaagctaa atcagccatt    780
ttgctcaatg aacgtgctag attaactgct gcacacccca tacaggacta cagcttaatg    840
aattatattg catatgttac ttacacgcca cttttcattg ccggccccat tataacattc    900
aatgattatg tttaccaatc gaaacatacc ttgccatcaa taaatttcaa attcattttt    960
tactatgcgg tgagattcgt tattgctctc ttatctatgg agttcatttt acactttctc   1020
cacgttgtgg caatctcaaa aaccaaagcg tgggaaaatg acacaccttt ccagatttcc   1080
```

```
atgattggct tatttaattt gaatattatt tggctaaaac tactgattcc gtggaggctg   1140
tttaggctgt gggctttgct agacggaatc gatacacctg aaaatatgat caggtgtgtt   1200
gataacaatt acagttcact agcattctgg agagcttggc atagaagcta caataagtgg   1260
gttgtccgtt acatatatat tcctctaggt ggttcaaaaa atagagtttt gacatcacta   1320
gcagtctttt ccttcgtagc tatatggcat gacatcgaac taaagttatt attatggggt   1380
tggctaatag ttttgttcct cttaccagaa atttttgcta cccaaatttt ctctcattat   1440
accgacgcag tctggtacag acacgtttgc gctgtcggtg ctgttttcaa catatgggtt   1500
atgatgatcg ctaatctttt tggattctgc ttgggctctg acggtactaa aaaattacta   1560
agcgatatgt tctgtaccgt atctggtttc aaatttgtaa ttttggcaag cgttagttta   1620
ttcatcgcag tacaaataat gtttgaaatc agagaagaag aaaagaggca cggaatttac   1680
ctaaaatgct gaggatcc                                                 1698
```

<210> SEQ ID NO 24
<211> LENGTH: 3037
<212> TYPE: DNA
<213> ORGANISM: Artificial
<220> FEATURE:
<223> OTHER INFORMATION: FPS1 PCR fragment

<400> SEQUENCE: 24

```
aagagctccg gactagtcgt acgaattcta tccttttgtt gtttccgggt gtacaatatg     60
gacttcctct tttctggcaa ccaaacccat acatcgggat tcctataata ccttcgttgg    120
tctccctaac atgtaggtgg cggaggggag atatacaata gaacagatac cagacaagac    180
ataatgggct aaacaagact acaccaatta cactgcctca ttgatggtgg tacataacga    240
actaatactg tagccctaga cttgatagcc atcatcatat cgaagtttca ctaccctttt    300
tccatttgcc atctattgaa gtaataatag gcgcatgcaa cttcttttct tttttttct     360
tttctctctc ccccgttgtt gtctcaccat atccgcaatg acaaaaaaat gatggaagac    420
actaaaggaa aaaattaacg acaaagacag caccaacaga tgtcgttgtt ccagagctga    480
tgaggggtat ctcgaagcac acgaaacttt ttccttcctt cattcacgca cactactctc    540
taatgagcaa cggtatacgg ccttccttcc agttacttga atttgaaata aaaaaagttt    600
gctgtcttgc tatcaagtat aaatagacct gcaattatta atcttttgtt tcctcgtcat    660
tgttctcgtt ccctttcttc cttgtttctt tttctgcaca atatttcaag ctataccaag    720
catacaatca actccagctg cattaaaatg agtaatcctc aaaaagctct aaacgacttt    780
ctgtccagtg aatctgttca tacacatgat agttctagga aacaatctaa taagcagtca    840
tccgacgaag gacgctcttc atcacaacct tcacatcatc actctggtgg tactaacaac    900
aataataaca ataataataa taataataac agtaacaaca acaacaacgg caacgatggg    960
ggaaatgatg acgactatga ttatgaaatg caagattata gaccttctcc gcaaagtgcg   1020
cggcctactc ccacgtatgt tccacaatat tctgtagaaa gtgggactgc tttcccgatt   1080
caagaggtta ttcctagcgc atacattaac acacaagata taaaccataa agataacggt   1140
ccgccgagtg caagcagtaa tagagcattc aggcctagag ggcagaccac agtgtcggcc   1200
aacgtgctta acattgaaga tttttacaaa aatgcagacg atgcgcatac catcccggag   1260
tcacatttat cgagaaggag aagtaggtcg agggctacga gtaatgctgg gcacagtgcc   1320
aatacaggcg ccacgaatgg caggactact ggtgcccaaa ctaatatgga aagcaatgaa   1380
```

-continued

```
tcaccacgta acgtccccat tatggtgaag ccaaagacat tataccagaa ccctcaaaca   1440
cctacagtct tgccctccac ataccatcca attaataaat ggtcttccgt caaaaacact   1500
tatttgaagg aatttttagc cgagtttatg ggaacaatgg ttatgattat tttcggtagt   1560
gctgttgttt gtcaggtcaa tgttgctggg aaaatacagc aggacaattt caacgtggct   1620
ttggataacc ttaacgttac cgggtcttct gcagaaacga tagacgctat gaagagttta   1680
acatccttgg tttcatccgt tgcgggcggt acctttgatg atgtggcatt gggctgggct   1740
gctgccgtgg tgatgggcta tttctgcgct ggtggtagtg ccatctcagg tgctcatttg   1800
aatccgtcta ttacattagc caatttggtg tatagaggtt ttccccctgaa gaaagttcct   1860
tattactttg ctggacaatt gatcggtgcc ttcacaggcg ctttgatctt gtttatttgg   1920
tacaaaaggg tgttacaaga ggcatatagc gattggtgga tgaatgaaag tgttgcggga   1980
atgttttgcg tttttccaaa gccttatcta agttcaggac ggcaattttt ttccgaattt   2040
ttatgtggag ctatgttaca agcaggaaca tttgcgctga ccgatcctta tacgtgtttg   2100
tcctctgatg ttttcccatt gatgatgttt attttgattt tcattatcaa tgcttccatg   2160
gcttatcaga caggtacagc aatgaatttg gctcgtgatc tgggcccacg tcttgcacta   2220
tatgcagttg gatttgatca taaaatgctt tgggtgcatc atcatcattt cttttgggtt   2280
cccatggtag gcccatttat tggtgcgtta atggggggggt tggtttacga tgtctgtatt   2340
tatcagggtc atgaatctcc agtcaactgg tctttaccag tttataagga aatgattatg   2400
agagcctggt ttagaaggcc tggttggaag aagagaaata gagcaagaag aacatcggac   2460
ctgagtgact tctcatacaa taacgatgat gatgaggaat ttggagaaag aatggctctt   2520
caaaagacaa agaccaagtc atctatttca gacaacgaaa atgaagcagg agaaaagaaa   2580
gtgcaattta aatctgttca gcgcggcaaa agaacgtttg gtggtatacc aacaattctt   2640
gaagaagaag attccattga aactgcttcg ctaggtgcga cgacgactga ttctattggg   2700
ttatccgaca catcatcaga agattcgcat tatggtaatg ctaagaaggt aacatgagga   2760
tccccttttc ctttgtcgat atcatgtaat tagttatgtc acgcttacat tcacgccctc   2820
ctcccacatc cgctctaacc gaaaaggaag gagttagaca acctgaagtc taggtcccta   2880
tttatttttt ttaatagtta tgttagtatt aagaacgtta tttatatttc aaatttttct   2940
ttttttctg tacaaacgcg tgtacgcatg taacattata ctgaaaacct tgcttgagaa   3000
ggttttggga cgctcgaagg cttcctaggc tcgagtt                             3037
```

<210> SEQ ID NO 25
<211> LENGTH: 552
<212> TYPE: PRT
<213> ORGANISM: Citrobacter freundii

<400> SEQUENCE: 25

```
Met Ser Gln Phe Phe Phe Asn Gln Arg Thr His Leu Val Ser Asp Val
1               5                   10                  15

Ile Asp Gly Thr Ile Ile Ala Ser Pro Trp Asn Asn Leu Ala Arg Leu
            20                  25                  30

Glu Ser Asp Pro Ala Ile Arg Ile Val Val Arg Arg Asp Leu Asn Lys
        35                  40                  45

Asn Asn Val Ala Val Ile Ser Gly Gly Gly Ser Gly His Glu Pro Ala
    50                  55                  60

His Val Gly Phe Ile Gly Lys Gly Met Leu Thr Ala Ala Val Cys Gly
65                  70                  75                  80
```

```
Asp Val Phe Ala Ser Pro Ser Val Asp Ala Val Leu Thr Ala Ile Gln
                85                  90                  95

Ala Val Thr Gly Glu Ala Gly Cys Leu Leu Ile Val Lys Asn Tyr Thr
            100                 105                 110

Gly Asp Arg Leu Asn Phe Gly Leu Ala Ala Glu Lys Ala Arg Arg Leu
        115                 120                 125

Gly Tyr Asn Val Glu Met Leu Ile Val Gly Asp Asp Ile Ser Leu Pro
    130                 135                 140

Asp Asn Lys His Pro Arg Gly Ile Ala Gly Thr Ile Leu Val His Lys
145                 150                 155                 160

Ile Ala Gly Tyr Phe Ala Glu Arg Gly Tyr Asn Leu Ala Thr Val Leu
                165                 170                 175

Arg Glu Ala Gln Tyr Ala Ala Asn Asn Thr Phe Ser Leu Gly Val Ala
            180                 185                 190

Leu Ser Ser Cys His Leu Pro Gln Glu Ala Asp Ala Ala Pro Arg His
        195                 200                 205

His Pro Gly His Ala Glu Leu Gly Met Gly Ile His Gly Glu Pro Gly
    210                 215                 220

Ala Ser Val Ile Asp Thr Gln Asn Ser Ala Gln Val Val Asn Leu Met
225                 230                 235                 240

Val Asp Lys Leu Met Ala Ala Leu Pro Glu Thr Gly Arg Leu Ala Val
                245                 250                 255

Met Ile Asn Asn Leu Gly Gly Val Ser Val Ala Glu Met Ala Ile Ile
            260                 265                 270

Thr Arg Glu Leu Ala Ser Ser Pro Leu His Pro Arg Ile Asp Trp Leu
        275                 280                 285

Ile Gly Pro Ala Ser Leu Val Thr Ala Leu Asp Met Lys Ser Phe Ser
    290                 295                 300

Leu Thr Ala Ile Val Leu Glu Glu Ser Ile Glu Lys Ala Leu Leu Thr
305                 310                 315                 320

Glu Val Glu Thr Ser Asn Trp Pro Thr Pro Val Pro Pro Arg Glu Ile
                325                 330                 335

Ser Cys Val Pro Ser Ser Gln Arg Ser Ala Arg Val Glu Phe Gln Pro
            340                 345                 350

Ser Ala Asn Ala Met Val Ala Gly Ile Val Glu Leu Val Thr Thr Thr
        355                 360                 365

Leu Ser Asp Leu Glu Thr His Leu Asn Ala Leu Asp Ala Lys Val Gly
    370                 375                 380

Asp Gly Asp Thr Gly Ser Thr Phe Ala Ala Gly Ala Arg Glu Ile Ala
385                 390                 395                 400

Ser Leu Leu His Arg Gln Gln Leu Pro Leu Asp Asn Leu Ala Thr Leu
                405                 410                 415

Phe Ala Leu Ile Gly Glu Arg Leu Thr Val Val Met Gly Gly Ser Ser
            420                 425                 430

Gly Val Leu Met Ser Ile Phe Phe Thr Ala Ala Gly Gln Lys Leu Glu
        435                 440                 445

Gln Gly Ala Ser Val Ala Glu Ser Leu Asn Thr Gly Leu Ala Gln Met
    450                 455                 460

Lys Phe Tyr Gly Gly Ala Asp Glu Gly Asp Arg Thr Met Ile Asp Ala
465                 470                 475                 480

Leu Gln Pro Ala Leu Thr Ser Leu Leu Thr Gln Pro Gln Asn Leu Gln
                485                 490                 495

Ala Ala Phe Asp Ala Ala Gln Ala Gly Ala Glu Arg Thr Cys Leu Ser
```

-continued

```
            500                 505                 510

Ser Lys Ala Asn Ala Gly Arg Ala Ser Tyr Leu Ser Ser Glu Ser Leu
        515                 520                 525

Leu Gly Asn Met Asp Pro Gly Ala His Ala Val Ala Met Val Phe Lys
    530                 535                 540

Ala Leu Ala Glu Ser Glu Leu Gly
545                 550


<210> SEQ ID NO 26
<211> LENGTH: 1678
<212> TYPE: DNA
<213> ORGANISM: Artificial
<220> FEATURE:
<223> OTHER INFORMATION: nucleotide sequence encoding the C. freundii
      dhaK codon-optimised for yeast

<400> SEQUENCE: 26

tctagaaaaa tgtctcaatt cttcttcaac cagagaaccc acttggtttc tgacgttatc     60

gacggtgcta tcatcgcttc accatggaac aatttggcta gattggaatc tgacccagct    120

atcagaatcg ttgttagaag agacttgaac aagaacaacg ttgctgttat ctctggtggt    180

ggttctggtc acgaaccagc tcacgttggt ttcatcggta agggtatgtt gaccgctgct    240

gtttgtggtg acgttttcgc ttctccatct gttgacgctg ttttgactgc tatccaagct    300

gttaccggtg aagctggttg tttgttgatc gttaagaact acaccggtga cagattgaac    360

ttcggtttgg ctgctgaaaa ggctagaaga ttgggttaca acgttgaaat gttgatcgtt    420

ggtgacgaca tctctttgcc agacaacaag cacccaagag gtatcgctgg taccatcttg    480

gttcacaaga tcgctggtta cttcgctgaa agaggttaca acttagctac cgttttgaga    540

gaagctcaat acgctgcttc taacaccttc tctttgggtg ttgctttgtc ttcttgtcac    600

ttgccacaag aaaccgacgc tgctccaaga caccacccag gtcacgctga attgggtatg    660

ggtatccacg gtgaaccagg tgcttctgtt atcgacaccc aaaactctgc tcaagttgtt    720

aacttgatgg ttgacaagtt gttggctgct ttgccagaaa ccggtagatt ggctgttatg    780

atcaacaact tgggtggtgt ttctgttgct gaaatggcta tcatcaccag agaattggct    840

tcttctccat tgcactcaag aatcgactgg ttgatcggtc cagcttcttt ggtaaccgct    900

ttggacatga agggtttctc tttgaccgct atcgttttgg aagaatctat cgaaaaggct    960

ttgttgaccg aagttgaaac ctctaactgg ccaaccccag ttccaccaag agaaatcacc   1020

tgtgttgttt cttctcacgc ttctgctaga gttgaattcc aaccatctgc taacgctttg   1080

gttgctggta tcgttgaatt ggttaccgct accttgtctg acttggaaac ccacttgaac   1140

gctttggacg ctaaggttgg tgacggtgac accggttcta ccttcgctgc tgctgctaga   1200

gaaatcgctt ctttgttgca cagacaacaa ttgccattga acaacttggc taccttgttc   1260

gctttgatcg gtgaaagatt gaccgttgtt atgggtggtt cttctggtgt tttgatgtct   1320

atcttcttca ccgctgctgg tcaaaagttg gaacaaggtg ctaacgttgt tgaagctttg   1380

aacaccggtt tggctcaaat gaagttctac ggtggtgctg acgaaggtga cagaaccatg   1440

atcgacgctt tgcaaccagc tttgacctct ttgttggctc aaccaaagaa cttgcaagct   1500

gctttcgacg ctgctcaagc tggtgctgaa agaacctgtt tgtcttctaa ggctaacgct   1560

ggtagagctt cttacttgtc ttctgaatct ttgttgggta acatggaccc aggtgctcaa   1620

agattggcta tggttttcaa ggctttggct gaatctgaat tgggttaata aggtcgac     1678
```

<210> SEQ ID NO 27
<211> LENGTH: 2951
<212> TYPE: DNA
<213> ORGANISM: Artificial
<220> FEATURE:
<223> OTHER INFORMATION: pRNdhaK

<400> SEQUENCE: 27
ggatccacta gtaacggccg ccagtgtgct ggaattcgcc cttctcgagc ttaagacgcg 60
tttcttcttc agattccctc atggagaaag tgcggcagat gtatatgaca gagtcgccag 120
tttccaagag actttattca ggcacttcca tgataggcaa gagagaagac ccagagatgt 180
tgttgtccta gttacacatg gtatttattc cagagtattc ctgatgaaat ggtttagatg 240
gacatacgaa gagtttgaat cgtttaccaa tgttcctaac gggagcgtaa tggtgatgga 300
actggacgaa tccatcaata gatacgtcct gaggaccgtg ctacccaaat ggactgattg 360
tgagggagac ctaactacat agtgtttaaa gattacggat atttaactta cttagaataa 420
tgccattttt ttgagttata ataatcctac gttagtgtga gcgggattta aactgtgagg 480
accttaatac attcagacac ttctgcggta tcaccctact tattcccttc gagattatat 540
ctaggaaccc atcaggttgg tggaagatta cccgttctaa gacttttcag cttcctctat 600
tgatgttaca cctggacacc ccttttctgg catccagttt ttaatcttca gtggcatgtg 660
agattctccg aaattaatta aagcaatcac acaattctct cggataccac ctcggttgaa 720
actgacaggt ggtttgttac gcatgctaat gcaaaggagc ctatatacct ttggctcggc 780
tgctgtaaca gggaatataa agggcagcat aatttaggag tttagtgaac ttgcaacatt 840
tactattttc ccttcttacg taaatatttt tctttttaat tctaaatcaa tctttttcaa 900
ttttttgttt gtattctttt cttgcttaaa tctataacta caaaaaacac atacataaat 960
ctagaaaaat gtctcaattc ttcttcaacc agagaaccca cttggtttct gacgttatcg 1020
acggtgctat catcgcttca ccatggaaca atttggctag attggaatct gacccagcta 1080
tcagaatcgt tgttagaaga gacttgaaca agaacaacgt tgctgttatc tctggtggtg 1140
gttctggtca cgaaccagct cacgttggtt tcatcggtaa gggtatgttg accgctgctg 1200
tttgtggtga cgttttcgct tctccatctg ttgacgctgt tttgactgct atccaagctg 1260
ttaccggtga agctggttgt ttgttgatcg ttaagaacta caccggtgac agattgaact 1320
tcggtttggc tgctgaaaag gctagaagat tgggttacaa cgttgaaatg ttgatcgttg 1380
gtgacgacat ctctttgcca gacaacaagc acccaagagg tatcgctggt accatcttgg 1440
ttcacaagat cgctggttac ttcgctgaaa gaggttacaa cttagctacc gttttgagag 1500
aagctcaata cgctgcttct aacaccttct ctttgggtgt tgctttgtct tcttgtcact 1560
tgccacaaga aaccgacgct gctccaagac accacccagg tcacgctgaa ttgggtatgg 1620
gtatccacgg tgaaccaggt gcttctgtta tcgacaccca aaactctgct caagttgtta 1680
acttgatggt tgacaagttg ttggctgctt tgccagaaac cggtagattg gctgttatga 1740
tcaacaactt gggtggtgtt tctgttgctg aaatggctat catcaccaga gaattggctt 1800
cttctccatt gcactcaaga atcgactggt tgatcggtcc agcttctttg gtaaccgctt 1860
tggacatgaa gggtttctct ttgaccgcta tcgttttgga agaatctatc gaaaaggctt 1920
tgttgaccga agttgaaacc tctaactggc caaccccagt tccaccaaga gaaatcacct 1980
gtgttgtttc ttctcacgct tctgctagag ttgaattcca accatctgct aacgctttgg 2040
ttgctggtat cgttgaattg gttaccgcta ccttgtctga cttggaaacc cacttgaacg 2100

-continued

```
ctttggacgc taaggttggt gacggtgaca ccggttctac cttcgctgct gctgctagag   2160
aaatcgcttc tttgttgcac agacaacaat tgccattgaa caacttggct accttgttcg   2220
ctttgatcgg tgaaagattg accgttgtta tgggtggttc ttctggtgtt ttgatgtcta   2280
tcttcttcac cgctgctggt caaaagttgg aacaaggtgc taacgttgtt gaagctttga   2340
acaccggttt ggctcaaatg aagttctacg gtggtgctga cgaaggtgac agaaccatga   2400
tcgacgcttt gcaaccagct ttgacctctt tgttggctca accaaagaac ttgcaagctg   2460
ctttcgacgc tgctcaagct ggtgctgaaa gaacctgttt gtcttctaag gctaacgctg   2520
gtagagcttc ttacttgtct tctgaatctt tgttgggtaa catggaccca ggtgctcaaa   2580
gattggctat ggttttcaag gctttggctg aatctgaatt gggttaataa ggtcgagaca   2640
aatcgctctt aaatatatac ctaaagaaca ttaaagctat attataagca aagatacgta   2700
aattttgctt atattattat acacatatca tatttctata tttttaagat ttggttatat   2760
aatgtacgta atgcaaagga aataaatttt atacattatt gaacagcgtc caagtaacta   2820
cattatgtgc actaatagtt tagcgtcgtg aagactttat tgtgtcgcga aaagtaaaaa   2880
ttttaaaaat tagagcacct tgaacttgcg aaaaaggttc tcatcaactg tttaaaacgt   2940
acgaagctta a                                                        2951
```

<210> SEQ ID NO 28
<211> LENGTH: 1949
<212> TYPE: DNA
<213> ORGANISM: Artificial
<220> FEATURE:
<223> OTHER INFORMATION: pRNgldA

<400> SEQUENCE: 28

```
actagtaaat gtgtggggaa gcgggtaagc tgccacagca attaatgcac aacatttaac     60
ctacattctt ccttatcgga tcctcaaaac ccttaaaaac atatgcctca ccctaacata    120
ttttccaatt aaccctcaat atttctctgt cacccggcct ctattttcca ttttcttctt    180
tacccgccac gcgttttttt ctttcaaatt tttttcttcc ttcttctttt tcttccacgt    240
cctcttgcat aaataaataa accgttttga aaccaaactc gcctctctct ctccttttttg   300
aaatattttt gggtttgttt gatcctttcc ttcccaatct ctcttgttta atatatattc    360
atttatatca cgctctcttt ttatcttcct ttttttcctc tctcttgtat tcttccttcc    420
cctttctact caaaccaaga agaaaaagaa aaggtcaatc tttgttaaag aataggatct    480
tctactacat cagcttttag atttttcacg cttactgctt ttttcttccc aagatcgaaa    540
atttactgaa ttaactgcag aaaatggaca gaatcatcca atctccaggt aagtacatcc    600
aaggtgctga cgttatcaac agattgggtg aatacttgaa gccattggct gaaagatggt    660
tggttgttgg tgacaagttc gttttgggtt tcgctcaatc taccgttgaa aagtctttca    720
aggacgctgg tttggttgtt gaaatcgctc cattcggtgg tgaatgttct caaaacgaaa    780
tcgacagatt gagaggtatc gctgaaaccg ctcaatgtgg tgctatcttg ggtatcggtg    840
gtggtaagac cttggacacc gctaaggctt tggctcactt catgggtgtt ccagttgcta    900
tcgctccaac catcgcttct accgacgctc catgttctgc tttgtctgtt atctacaccg    960
acgaaggtga attcgacaga tacttgttgt tgccaaacaa cccaaacatg gttatcgttg   1020
acaccaagat cgttgctggt gctccagcta gattgttggc agctggtatc ggtgacgctt   1080
tggctacctg gttcgaagct agagcttgtt ctagatctgg tgctaccacc atggctggtg   1140
gtaagtgtac ccaagctgct ttggctttgg ctgaattgtg ttacaacacc ttgttggaag   1200
```

aaggtgaaaa ggctatgttg gctgctgaac aacacgttgt taccccagct ttggaaagag 1260
ttatcgaagc taacacctac ttgtctggtg ttggtttcga atctggtggt ttggctgctg 1320
ctcacgctgt tcacaacggt ttgaccgcta tcccagacgc tcaccactac taccacggtg 1380
aaaaggttgc tttcggtacc ttgacccaat tggttttgga aaacgctcca gttgaagaaa 1440
tcgaaaccgt tgctgctttg tctcacgctg ttggtttgcc aatcaccttg gctcaattgg 1500
acatcaagga agacgttcca gctaagatga gaatcgttgc tgaagctgct tgtgctgaag 1560
gtgaaaccat ccacaacatg ccaggtggtg ctaccccaga ccaagtttac gctgctttgt 1620
tggttgctga ccaatacggt caaagattcc tacaagaatg ggaataaggc gcgccccttt 1680
tcctttgtcg atatcatgta attagttatg tcacgcttac attcacgccc tcctccccaca 1740 tccgctctaa ccgaaaagga aggagttaga caacctgaag tctaggtccc tatttatttt 1800
ttttaatagt tatgttagta ttaagaacgt tatttatatt tcaaattttt cttttttttc 1860
tgtacaaacg cgtgtacgca tgtaacatta tactgaaaac cttgcttgag aaggttttgg 1920
gacgctcgaa ggcttcctag gcgtacgtt 1949

<210> SEQ ID NO 29
<211> LENGTH: 7690
<212> TYPE: DNA
<213> ORGANISM: Artificial
<220> FEATURE:
<223> OTHER INFORMATION: pRN558

<400> SEQUENCE: 29
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataattc cgttttaaga gcttggtgag cgctaggagt cactgccagg tatcgtttga 240
acacggcatt agtcagggaa gtcataacac agtcctttcc cgcaattttc tttttctatt 300
actcttggcc tcctctagta cactctatat ttttttatgc ctcggtaatg attttcattt 360
ttttttttcc acctagcgga tgactctttt tttttcttag cgattggcat tatcacataa 420
tgaattatac attatataaa gtaatgtgat ttcttcgaag aatatactaa aaaatgagca 480
ggcaagataa acgaaggcaa agatgacaga gcagaaagcc ctagtaaagc gtattacaaa 540
tgaaaccaag attcagattg cgatctcttt aaagggtggt cccctagcga tagagcactc 600
gatcttccca gaaaaagagg cagaagcagt agcagaacag gccacacaat cgcaagtgat 660
taacgtccac acaggtatag ggtttctgga ccatatgata catgctctgg ccaagcattc 720
cggctggtcg ctaatcgttg agtgcattgg tgacttacac atagacgacc atcacaccac 780
tgaagactgc gggattgctc tcggtcaagc ttttaaagag gccctactgg cgcgtggagt 840
aaaaaggttt ggatcaggat ttgcgccttt ggatgaggca ctttccagag cggtggtaga 900
tctttcgaac aggccgtacg cagttgtcga acttggtttg caaagggaga aagtaggaga 960
tctctcttgc gagatgatcc cgcattttct tgaaagcttt gcagaggcta gcagaattac 1020
cctccacgtt gattgtctgc gaggcaagaa tgatcatcac cgtagtgaga gtgcgttcaa 1080
ggctcttgcg gttgccataa gagaagccac ctcgcccaat ggtaccaacg atgttccctc 1140
caccaaaggt gttcttatgt agtgacaccg attatttaaa gctgcagcat acgatatata 1200
tacatgtgta tatatgtata cctatgaatg tcagtaagta tgtatacgaa cagtatgata 1260

-continued

```
ctgaagatga caaggtaatg catcattcta tacgtgtcat tctgaacgag gcgcgctttc   1320
cttttttctt tttgcttttt cttttttttt ctcttgaact cgacggatca tatgcggtgt   1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcattgcga ataccgcttc cacaaacatt gctcaaaagt atctctttgc   1800
tatatatctc tgtgctatat ccctatataa cctacccatc cacctttcgc tccttgaact   1860
tgcatctaaa ctcgacctct acatttttta tgtttatctc tagtattact ctttagacaa   1920
aaaaattgta gtaagaacta ttcatagagt gaatcgaaaa caatacgaaa atgtaaacat   1980
ttcctatacg tagtatatag agacaaaata gaagaaaccg ttcataattt tctgaccaat   2040
gaagaatcat caacgctatc actttctgtt cacaaagtat gcgcaatcca catcggtata   2100
gaatataatc ggggatgcct ttatcttgaa aaaatgcacc cgcagcttcg ctagtaatca   2160
gtaaacgcgg gaagtggagt caggcttttt ttatggaaga gaaaatagac accaaagtag   2220
ccttcttcta accttaacgg acctacagtg caaaaagtta tcaagagact gcattataga   2280
gcgcacaaag gagaaaaaaa gtaatctaag atgctttgtt agaaaaatag cgctctcggg   2340
atgcattttt gtagaacaaa aaagaagtat agattctttg ttggtaaaat agcgctctcg   2400
cgttgcattt ctgttctgta aaaatgcagc tcagattctt tgtttgaaaa attagcgctc   2460
tcgtcgcgtt gcatttttgt tttacaaaaa tgaagcacag attcttcgtt ggtaaaatag   2520
cgctttcgcg ttgcatttct gttctgtaaa aatgcagctc agattctttg tttgaaaaat   2580
tagcgctctc gcgttgcatt tttgttctac aaaatgaagc acagatgctt cgttaacaaa   2640
gatatgctat tgaagtgcaa gatggaaacg cagaaaatga accggggatg cgacgtgcaa   2700
gattacctat gcaatagatg caatagtttc tccaggaacc gaaatacata cattgtcttc   2760
cgtaaagcgc tagactatat attattatac aggttcaaat atactatctg tttcagggaa   2820
aactcccagg ttcggatgtt caaaattcaa tgatgggtaa caagtacgat cgtaaatctg   2880
taaaacagtt tgtcggatat taggctgtat ctcctcaaag cgtattcgaa tatcattgag   2940
aagctgcagc gtcacatcgg ataataatga tggcagccat tgtagaagtg ccttttgcat   3000
ttctagtctc tttctcggtc tagctagttt tactacatcg cgaagataga atcttagatc   3060
acactgcctt tgctgagctg gatcaataga gtaacaaaag agtggtaagg cctcgttaaa   3120
ggacaaggac ctgagcggaa gtgtatcgta cagtagacgg agtatctagt atagtctata   3180
gtccgtggaa ttaattctca tctttgacag cttatcatcg ataatccgga gctagcatgc   3240
ggccgccagt gtgatggata tctgcagaat tcgccctttt aagcttcgta cgtgtggaag   3300
aacgattaca acaggtgttg tcctctgagg acataaaata cacaccgaga ttcatcaact   3360
cattgctgga gttagcatat ctacaattgg gtgaaatggg gagcgatttg caggcatttg   3420
ctcggcatgc cggtagaggt gtggtcaata agagcgacct catgctatac ctgagaaagc   3480
aacctgacct acaggaaaga gttactcaag aataagaatt ttcgttttaa aacctaagag   3540
tcactttaaa atttgtatac acttattttt tttataactt atttaataat aaaaatcata   3600
aatcataaga aattcgcgcg cttaagcagc ttcaccagcc tttctagcca aagattgagc   3660
```

catcttttca gcggtagcca aagcagaaga ggtcataatg tccaagttac cagcgtaagc 3720
tggcaagtag tgagcagcac cttcaacttc caaccaaaca gcggtcttca aaccagagaa 3780
ttgaccaaca cctggcaagt taactggctt gtcttgtggg ataacttcga attgaactct 3840
ttgcttcaat ctgtaacctg gaacgtatgc ttgaacagct tcagccattt cgttgattga 3900
agcttcgatg tcgtcttgag atgcttcgtc agacaaaacg taaacggtgt ctctcatcat 3960
caatggtggt tcagctgggt tcaaaacgat gatagcctta cccttagcag caccaccaac 4020
aacttcgata gccctagagg tggtttcggt gaattcgtcg atgttagctc tggtacctgg 4080
accagcagac ttagaagcga tagaagcgat gatttcagcg tagtgaactc tagcaactct 4140
tgaaacagca gcaaccattg ggatggtagc ttgaccacca caggtaacca tgttaacgtt 4200
taattggtca acgttagctt ccaagttaac aactggaaca cagtatggac cgatagcagc 4260
tggggtcaag tcgatcaatc tgatgtctgg cttagcttct ctcaaagcag cgtcgttctt 4320
aacgtgagca ccagcagagg tagcgtcgaa aacgatgtcg atgtcagcga attctggcat 4380
gttcatcaaa ccgataacac cttcgtgggt ggtagcaaca cccattcttc tagctctagc 4440
caaaccgtca gattgtgggt cgataccaac cataacagcc atttccaagt gttgaccgtg 4500
tcttaggatc ttgatcatca agtcagtacc gatgttacca gaaccgatga tagcaacctt 4560
tctcttagac atctgcagtc tagatatatt tgttgtaaaa agtagataat tacttccttg 4620
atgatctgta aaaaagagaa aaagaaagca tctaagaact tgaaaaacta cgaattagaa 4680
aagaccaaat atgtatttct tgcattgacc aatttatgca agtttatata tatgtaaatg 4740
taagtttcac gaggttctac taaactaaac caccccccttg gttagaagaa aagagtgtgt 4800
gagaacaggc tgttgttgtc acacgattcg gacaattctg tttgaaagag agagagtaac 4860
agtacgatcg aacgaacttt gctctggaga tcacagtggg catcatagca tgtggtacta 4920
aacccttcc cgccattcca gaaccttcga ttgcttgtta caaaacctgt gagccgtcgc 4980
taggaccttg ttgtgtgacg aaattggaag ctgcaatcaa taggaagaca ggaagtcgag 5040
cgtgtctggg ttttttcagt tttgttcttt ttgcaaacaa atcacgagcg acggtaattt 5100
ctttctcgat aagaggccac gtgctttatg agggtaacat caattcaaga aggagggaaa 5160
cacttccttt ttctggccct gataatagta tgagggtgaa gccaaaataa aggattcgcg 5220
cccaaatcgg catctttaaa tgcaggtatg cgatagttcc tcactctttc cttactcacg 5280
agtaattctt gcaaatgcct attatgcaga tgttataata tctgtgcgtc ttgagttgaa 5340
gagctcgaga ctagtggatc ccccgggctg caggaattcg atatcaagct tatcgatacc 5400
gtcgacctcg aggggggggcc cggtacccag cttttgttcc ctttagtgag ggttaattcc 5460
gagcttggcg taatcatggt catagctgtt tcctgtgtga aattgttatc cgctcacaat 5520
tccacacaac ataggagccg gaagcataaa gtgtaaagcc tggggtgcct aatgagtgag 5580
gtaactcaca ttaattgcgt tgcgctcact gcccgctttc cagtcgggaa acctgtcgtg 5640
ccagctgcat taatgaatcg gccaacgcgc ggggagaggc ggtttgcgta ttgggcgctc 5700
ttccgcttcc tcgctcactg actcgctgcg ctcggtcgtt cggctgcggc gagcggtatc 5760
agctcactca aaggcggtaa tacggttatc cacagaatca ggggataacg caggaaagaa 5820
catgtgagca aaaggccagc aaaaggccag gaaccgtaaa aaggccgcgt tgctggcgtt 5880
tttccatagg ctcggccccc ctgacgagca tcacaaaaat cgacgctcaa gtcagaggtg 5940
gcgaaacccg acaggactat aaagatacca ggcgttcccc cctggaagct ccctcgtgcg 6000

-continued

```
ctctcctgtt ccgaccctgc cgcttaccgg atacctgtcc gcctttctcc cttcgggaag   6060

cgtggcgctt tctcaatgct cacgctgtag gtatctcagt tcggtgtagg tcgttcgctc   6120

caagctgggc tgtgtgcacg aaccccccgt tcagcccgac cgctgcgcct tatccggtaa   6180

ctatcgtctt gagtccaacc cggtaagaca cgacttatcg ccactggcag cagccactgg   6240

taacaggatt agcagagcga ggtatgtagg cggtgctaca gagttcttga agtggtggcc   6300

taactacggc tacactagaa ggacagtatt tggtatctgc gctctgctga agccagttac   6360

cttcggaaaa agagttggta gctcttgatc cggcaaacaa accaccgctg gtagcggtgg   6420

tttttttgtt tgcaagcagc agattacgcg cagaaaaaaa ggatctcaag aagatccttt   6480

gatcttttct acggggtctg acgctcagtg gaacgaaaac tcacgttaag ggattttggt   6540

catgagatta tcaaaaagga tcttcaccta gatcctttta aattaaaaat gaagttttaa   6600

atcaatctaa agtatatatg agtaaacttg gtctgacagt taccaatgct taatcagtga   6660

ggcacctatc tcagcgatct gtctatttcg ttcatccata gttgcctgac tgcccgtcgt   6720

gtagataact acgatacggg agggcttacc atctggcccc agtgctgcaa tgataccgcg   6780

agacccacgc tcaccggctc cagatttatc agcaataaac cagccagccg gaagggccga   6840

gcgcagaagt ggtcctgcaa ctttatccgc ctccatccag tctattaatt gttgccggga   6900

agctagagta agtagttcgc cagttaatag tttgcgcaac gttgttgcca ttgctacagg   6960

catcgtggtg tcacgctcgt cgtttggtat ggcttcattc agctccggtt cccaacgatc   7020

aaggcgagtt acatgatccc ccatgttgtg aaaaaaagcg gttagctcct tcggtcctcc   7080

gatcgttgtc agaagtaagt tggccgcagt gttatcactc atggttatgg cagcactgca   7140

taattctctt actgtcatgc catccgtaag atgcttttct gtgactggtg agtactcaac   7200

caagtcattc tgagaatagt gtatgcggcg accgagttgc tcttgcccgg cgtcaatacg   7260

ggataatacc gcgccacata gcagaacttt aaaagtgctc atcattggaa aacgttcttc   7320

ggggcgaaaa ctctcaagga tcttaccgct gttgagatcc agttcgatgt aacccactcg   7380

tgcacccaac tgatcttcag catcttttac tttcaccagc gtttctgggt gagcaaaaac   7440

aggaaggcaa aatgccgcaa aaaagggaat aagggcgaca cggaaatgtt gaatactcat   7500

actcttcctt tttcaatatt attgaagcat ttatcagggt tattgtctca tgagcggata   7560

catatttgaa tgtatttaga aaaataaaca aataggggtt ccgcgcacat ttccccgaaa   7620

agtgccacct gacgtcttat tatcatgaca ttaacctata aaaataggcg tatcacgagg   7680

ccctttcgtc                                                          7690
```

<210> SEQ ID NO 30
<211> LENGTH: 9416
<212> TYPE: DNA
<213> ORGANISM: Artificial
<220> FEATURE:
<223> OTHER INFORMATION: pRN595

<400> SEQUENCE: 30

```
gacgaaaggg cctcgtgata cgcctatttt tataggttaa tgtcatgata ataagacgtc     60

aggtggcact tttcggggaa atgtgcgcgg aacccctatt tgtttatttt tctaaataca    120

ttcaaatatg tatccgctca tgagacaata accctgataa atgcttcaat aatattgaaa    180

aaggaagagt atgagtattc aacatttccg tgtcgccctt attccctttt ttgcggcatt    240

ttgccttcct gtttttgctc acccagaaac gctggtgaaa gtaaaagatg ctgaagatca    300

gttgggtgca cgagtgggtt acatcgaact ggatctcaac agcggtaaga tccttgagag    360
```

-continued

```
ttttcgcccc gaagaacgtt ttccaatgat gagcactttt aaagttctgc tatgtggcgc    420
ggtattatcc cgtattgacg ccgggcaaga gcaactcggt cgccgcatac actattctca    480
gaatgacttg gttgagtact caccagtcac agaaaagcat cttacggatg gcatgacagt    540
aagagaatta tgcagtgctg ccataaccat gagtgataac actgcggcca acttacttct    600
gacaacgatc ggaggaccga aggagctaac cgcttttttt cacaacatgg gggatcatgt    660
aactcgcctt gatcgttggg aaccggagct gaatgaagcc ataccaaacg acgagcgtga    720
caccacgatg cctgtagcaa tggcaacaac gttgcgcaaa ctattaactg gcgaactact    780
tactctagct tcccggcaac aattaataga ctggatggag gcggataaag ttgcaggacc    840
acttctgcgc tcggcccttc cggctggctg gtttattgct gataaatctg gagccggtga    900
gcgtgggtct cgcggtatca ttgcagcact ggggccagat ggtaagccct cccgtatcgt    960
agttatctac acgacgggca gtcaggcaac tatggatgaa cgaaatagac agatcgctga   1020
gataggtgcc tcactgatta agcattggta actgtcagac caagtttact catatatact   1080
ttagattgat ttaaaacttc atttttaatt taaaaggatc taggtgaaga tcctttttga   1140
taatctcatg accaaaatcc cttaacgtga gttttcgttc cactgagcgt cagaccccgt   1200
agaaaagatc aaaggatctt cttgagatcc tttttttctg cgcgtaatct gctgcttgca   1260
aacaaaaaaa ccaccgctac cagcggtggt ttgtttgccg gatcaagagc taccaactct   1320
ttttccgaag gtaactggct tcagcagagc gcagatacca aatactgtcc ttctagtgta   1380
gccgtagtta ggccaccact tcaagaactc tgtagcaccg cctacatacc tcgctctgct   1440
aatcctgtta ccagtggctg ctgccagtgg cgataagtcg tgtcttaccg ggttggactc   1500
aagacgatag ttaccggata aggcgcagcg gtcgggctga acggggggtt cgtgcacaca   1560
gcccagcttg gagcgaacga cctacaccga actgagatac ctacagcgtg agcattgaga   1620
aagcgccacg cttcccgaag ggagaaaggc ggacaggtat ccggtaagcg gcagggtcgg   1680
aacaggagag cgcacgaggg agcttccagg gggaaacgcc tggtatcttt atagtcctgt   1740
cgggtttcgc cacctctgac ttgagcgtcg atttttgtga tgctcgtcag gggggccgag   1800
cctatggaaa aacgccagca acgcggcctt tttacggttc ctggcctttt gctggccttt   1860
tgctcacatg ttctttcctg cgttatcccc tgattctgtg gataaccgta ttaccgcctt   1920
tgagtgagct gataccgctc gccgcagccg aacgaccgag cgcagcgagt cagtgagcga   1980
ggaagcggaa gagcgcccaa tacgcaaacc gcctctcccc gcgcgttggc cgattcatta   2040
atgcagctgg cacgacaggt ttcccgactg gaaagcgggc agtgagcgca acgcaattaa   2100
tgtgagttac ctcactcatt aggcacccca ggctttacac tttatgcttc cggctcctat   2160
gttgtgtgga attgtgagcg gataacaatt tcacacagga aacagctatg accatgatta   2220
cgccaagctc ggaattaacc ctcactaaag ggaacaaaag ctgggtaccg ggccccccct   2280
cgaggtcgac ggtatcgata agcttgatat cgaattcctg cagcccgggg gatccactag   2340
tctcgagctc ttcaactcaa gacgcacaga tattataaca tctgcataat aggcatttgc   2400
aagaattact cgtgagtaag gaaagagtga ggaactatcg catacctgca tttaaagatg   2460
ccgatttggg cgcgaatcct ttattttggc ttcaccctca tactattatc agggccagaa   2520
aaaggaagtg tttccctcct tcttgaattg atgttaccct cataaagcac gtggcctctt   2580
atcgagaaag aaattaccgt cgctcgtgat ttgtttgcaa aaagaacaaa actgaaaaaa   2640
cccagacacg ctcgacttcc tgtcttccta ttgattgcag cttccaattt cgtcacacaa   2700
```

-continued

```
caaggtccta gcgacggctc acaggttttg taacaagcaa tcgaaggttc tggaatggcg   2760
ggaaagggtt tagtaccaca tgctatgatg cccactgtga tctccagagc aaagttcgtt   2820
cgatcgtact gttactctct ctctttcaaa cagaattgtc cgaatcgtgt gacaacaaca   2880
gcctgttctc acacactctt ttcttctaac caagggggtg gtttagttta gtagaacctc   2940
gtgaaactta catttacata tatataaact tgcataaatt ggtcaatgca agaaatacat   3000
atttggtctt ttctaattcg tagtttttca agttcttaga tgctttcttt ttctcttttt   3060
tacagatcat caaggaagta attatctact ttttacaaca aatatatcta gaaaatggct   3120
gttaccaacg ttgctgaatt gaacgctttg gttgaaaggg ttaagaaggc tcaaagagaa   3180
tacgcttctt tcacccaaga acaagttgac aagatcttca gagctgctgc tttggctgct   3240
gctgacgcta gaatcccatt ggctaagatg gctgttgctg aatctggtat gggtatcgtt   3300
gaagacaagg ttatcaagaa ccacttcgct tctgaataca tctacaacgc ttacaaggac   3360
gaaaagacct gtggtgtttt gtcagaagac gacaccttcg gtaccatcac catcgctgaa   3420
ccaatcggta tcatctgtgg tatcgttcca accaccaacc caacctctac cgctatcttc   3480
aagtctttga tctctttgaa gaccagaaac gctatcatct tctctccaca cccaagagct   3540
aaagacgcta ccaacaaggc tgctgacatc gttttgcaag ctgctatcgc tgctggtgct   3600
ccaaaggact tgatcggttg gatcgaccaa ccatctgttg aattgtctaa cgctttgatg   3660
caccacccag acatcaactt gatcttggct accggtggtc caggtatggt taaggctgct   3720
tactcttctg gtaagccagc tatcggtgtt ggtgctggta acaccccagt tgttatcgac   3780
gaaaccgctg acatcaagag agctgttgct tctgttttga tgtctaagac cttcgacaac   3840
ggtgttatct gtgcttctga acaatctgtt gttgttgttg actctgttta cgacgctgtt   3900
agagaaagat tcgctaccca cggtggttac ttgttgcaag gtaaggaatt gaaggctgtt   3960
caagacgtta tcttgaagaa cggtgctttg aacgctgcta tcgttggtca accagcttac   4020
aagatcgctg aattagctgg tttctctgtt ccagaaaaca ccaagatctt gatcggtgaa   4080
gttaccgttg ttgacgaatc tgaaccattc gctcacgaaa agttgtctcc aaccttggct   4140
atgtacagag ctaaggactt cgaagacgct gttgaaaaag ctgaaaagtt ggttgctatg   4200
ggtggtattg gtcacacctc ttgtttgtac accgaccaag acaaccaacc agctagagtt   4260
tcttacttcg gtcaaaagat gaagaccgct agaatcttga tcaacacccc agcttctcaa   4320
ggtggtatcg gtgacttgta caacttcaag ttggctccat ctttgacctt gggttgtggt   4380
tcttggggtg gtaactctat ctctgaaaac gttggtccaa agcacttgat caacaagaag   4440
accgttgcta agagagctga aaacatgttg tggcacaagt tgccaaaatc tatctacttc   4500
agaagaggtt ctttgccaat cgctttggac gaagttatca ccgacggtca caagagagct   4560
ttgatcgtta ccgacagatt cttgttcaac aacggttacg ctgaccaaat cacctctgtt   4620
ttgaaggctg ctggtgttga aaccgaagtt ttcttcgaag ttgaagctga cccaaccttg   4680
tctatcgtta gaaagggtgc tgaattggct aactctttca agccagacgt tatcatcgct   4740
ttgggtggtg gttctccaat ggacgctgct aagatcatgt gggttatgta cgaacaccca   4800
gaaacccact tcgaagaatt ggctttgaga ttcatggaca tcagaaagag aatctacaag   4860
ttcccaaaga tgggtgttaa ggctaagatg atcgctgtta ccaccacctc tggtaccggt   4920
tctgaagtta ccccattcgc tgttgttacc gacgacgcta ccggtcaaaa gtacccattg   4980
gctgactacg ctttgacccc agacatggct atcgttgacg ctaacttggt tatggacatg   5040
ccaaagtctt tgtgtgcttt cggtggtttg gacgctgtta cccacgctat ggaagcttac   5100
```

-continued

```
gtttctgttt tggcttctga attctctgac ggtcaagctt tgcaagcttt gaagttgttg   5160
aaggaatact tgccagcttc ttaccacgaa ggttctaaga acccagttgc tagagaaaga   5220
gttcactctg ctgctaccat cgctggtatc gctttcgcta acgctttctt gggtgtttgt   5280
cactctatgg ctcacaagtt gggttctcaa ttccacatcc cacacggttt ggctaacgct   5340
ttgttgatct gtaacgttat cagatacaac gctaacgaca acccaaccaa gcaaaccgct   5400
ttctctcaat acgacagacc acaagctaga agaagatacg ctgaaatcgc tgaccacttg   5460
ggtttgtctg ctccaggtga cagaaccgct gcaaagatcg aaaagttgtt ggcttggttg   5520
gaaaccttga aggctgaatt gggtatccca aagtctatca gagaagctgg tgttcaagaa   5580
gctgacttct tggctaacgt tgacaagttg tctgaagacg ctttcgacga ccaatgtacc   5640
ggtgctaacc caagataccc attgatctct gaattgaagc aaatcttgtt ggacacctac   5700
tacggtagag actacgttga aggtgaaacc gctgctaaga aggaagctgc tccagctaag   5760
gctgaaaaga aggctaagaa gtctgcttag cttaagcgcg cgaatttctt atgatttatg   5820
atttttatta ttaaataagt tataaaaaaa ataagtgtat acaaatttta aagtgactct   5880
taggttttaa aacgaaaatt cttattcttg agtaactctt tcctgtaggt caggttgctt   5940
tctcaggtat agcatgaggt cgctcttatt gaccacacct ctaccggcat gccgagcaaa   6000
tgcctgcaaa tcgctcccca tttcacccaa ttgtagatat gctaactcca gcaatgagtt   6060
gatgaatctc ggtgtgtatt ttatgtcctc agaggacaac acctgttgta atcgttcttc   6120
cacacgtacg aagcttaaaa gggcgaattc tgcagatatc catcacactg gcggccgcat   6180
gctagctccg gattatcgat gataagctgt caaagatgag aattaattcc acggactata   6240
gactatacta gatactccgt ctactgtacg atacacttcc gctcaggtcc ttgtccttta   6300
acgaggcctt accactcttt tgttactcta ttgatccagc tcagcaaagg cagtgtgatc   6360
taagattcta tcttcgcgat gtagtaaaac tagctagacc gagaaagaga ctagaaatgc   6420
aaaaggcact tctacaatgg ctgccatcat tattatccga tgtgacgctg cagcttctca   6480
atgatattcg aatacgcttt gaggagatac agcctaatat ccgacaaact gttttacaga   6540
tttacgatcg tacttgttac ccatcattga attttgaaca tccgaacctg ggagttttcc   6600
ctgaaacaga tagtatattt gaacctgtat aataatatat agtctagcgc tttacggaag   6660
acaatgtatg tatttcggtt cctggagaaa ctattgcatc tattgcatag gtaatcttgc   6720
acgtcgcatc cccggttcat ttttctgcgtt tccatcttgc acttcaatag catatctttg   6780
ttaacgaagc atctgtgctt cattttgtag aacaaaaatg caacgcgaga gcgctaattt   6840
ttcaaacaaa gaatctgagc tgcattttta cagaacagaa atgcaacgcg aaagcgctat   6900
tttaccaacg aagaatctgt gcttcatttt tgtaaaacaa aaatgcaacg cgacgagagc   6960
gctaattttt caaacaaaga atctgagctg catttttaca gaacagaaat gcaacgcgag   7020
agcgctattt taccaacaaa gaatctatac ttcttttttg ttctacaaaa atgcatcccg   7080
agagcgctat ttttctaaca aagcatctta gattactttt tttctccttt gtgcgctcta   7140
taatgcagtc tcttgataac tttttgcact gtaggtccgt taaggttaga agaaggctac   7200
tttggtgtct attttctctt ccataaaaaa agcctgactc cacttcccgc gtttactgat   7260
tactagcgaa gctgcgggtg catttttca agataaaggc atccccgatt atattctata   7320
ccgatgtgga ttgcgcatac tttgtgaaca gaaagtgata gcgttgatga ttcttcattg   7380
gtcagaaaat tatgaacggt ttcttctatt ttgtctctat atactacgta taggaaatgt   7440
```

```
ttacattttc gtattgtttt cgattcactc tatgaatagt tcttactaca atttttttgt   7500

ctaaagagta atactagaga taaacataaa aaatgtagag gtcgagttta gatgcaagtt   7560

caaggagcga aaggtggatg ggtaggttat atagggatat agcacagaga tatatagcaa   7620

agagatactt ttgagcaatg tttgtggaag cggtattcgc aatgccggct ttccccgtca   7680

agctctaaat cgggggctcc ctttagggtt ccgatttagt gctttacggc acctcgaccc   7740

caaaaaactt gattagggtg atggttcacg tagtgggcca tcgccctgat agacggtttt   7800

tcgccctttg acgttggagt ccacgttctt taatagtgga ctcttgttcc aaactggaac   7860

aacactcaac cctatctcgg tctattcttt tgatttataa gggattttgc cgatttcggc   7920

ctattggtta aaaaatgagc tgatttaaca aaaatttaac gcgaatttta acaaaatatt   7980

aacgtttaca atttcctgat gcggtatttt ctccttacgc atctgtgcgg tatttcacac   8040

cgcatatgat ccgtcgagtt caagagaaaa aaaaagaaaa agcaaaaaga aaaaaggaaa   8100

gcgcgcctcg ttcagaatga cacgtataga atgatgcatt accttgtcat cttcagtatc   8160

atactgttcg tatacatact tactgacatt cataggtata catatataca catgtatata   8220

tatcgtatgc tgcagcttta aataatcggt gtcactacat aagaacacct ttggtggagg   8280

gaacatcgtt ggtaccattg ggcgaggtgg cttctcttat ggcaaccgca agagccttga   8340

acgcactctc actacggtga tgatcattct tgcctcgcag acaatcaacg tggagggtaa   8400

ttctgctagc ctctgcaaag ctttcaagaa aatgcgggat catctcgcaa gagagatctc   8460

ctactttctc cctttgcaaa ccaagttcga caactgcgta cggcctgttc gaaagatcta   8520

ccaccgctct ggaaagtgcc tcatccaaag gcgcaaatcc tgatccaaac ctttttactc   8580

cacgcgccag tagggcctct ttaaaagctt gaccgagagc aatcccgcag tcttcagtgg   8640

tgtgatggtc gtctatgtgt aagtcaccaa tgcactcaac gattagcgac cagccggaat   8700

gcttggccag agcatgtatc atatggtcca gaaaccctat acctgtgtgg acgttaatca   8760

cttgcgattg tgtggcctgt tctgctactg cttctgcctc tttttctggg aagatcgagt   8820

gctctatcgc taggggacca ccctttaaag agatcgcaat ctgaatcttg gtttcatttg   8880

taatacgctt tactagggct ttctgctctg tcatctttgc cttcgtttat cttgcctgct   8940

catttttag tatattcttc gaagaaatca cattacttta tataatgtat aattcattat   9000

gtgataatgc caatcgctaa gaaaaaaaaa gagtcatccg ctaggtggaa aaaaaaaaat   9060

gaaaatcatt accgaggcat aaaaaaatat agagtgtact agaggaggcc aagagtaata   9120

gaaaaagaaa attgcgggaa aggactgtgt tatgacttcc ctgactaatg ccgtgttcaa   9180

acgatacctg gcagtgactc ctagcgctca ccaagctctt aaaacggaat tatggtgcac   9240

tctcagtaca atctgctctg atgccgcata gttaagccag ccccgacacc cgccaacacc   9300

cgctgacgcg ccctgacggg cttgtctgct cccggcatcc gcttacagac aagctgtgac   9360

cgtctccggg agctgcatgt gtcagaggtt ttcaccgtca tcaccgaaac gcgcga       9416
```

<210> SEQ ID NO 31
<211> LENGTH: 9352
<212> TYPE: DNA
<213> ORGANISM: Artificial
<220> FEATURE:
<223> OTHER INFORMATION: pRN596

<400> SEQUENCE: 31

```
gacgaaaggg cctcgtgata cgcctatttt tataggttaa tgtcatgata ataagacgtc     60

aggtggcact tttcggggaa atgtgcgcgg aacccctatt tgtttatttt tctaaataca    120
```

-continued

```
ttcaaatatg tatccgctca tgagacaata accctgataa atgcttcaat aatattgaaa    180
aaggaagagt atgagtattc aacatttccg tgtcgccctt attccctttt ttgcggcatt    240
ttgccttcct gtttttgctc acccagaaac gctggtgaaa gtaaaagatg ctgaagatca    300
gttgggtgca cgagtgggtt acatcgaact ggatctcaac agcggtaaga tccttgagag    360
ttttcgcccc gaagaacgtt ttccaatgat gagcactttt aaagttctgc tatgtggcgc    420
ggtattatcc cgtattgacg ccgggcaaga gcaactcggt cgccgcatac actattctca    480
gaatgacttg gttgagtact caccagtcac agaaaagcat cttacggatg gcatgacagt    540
aagagaatta tgcagtgctg ccataaccat gagtgataac actgcggcca acttacttct    600
gacaacgatc ggaggaccga aggagctaac cgcttttttt cacaacatgg gggatcatgt    660
aactcgcctt gatcgttggg aaccggagct gaatgaagcc ataccaaacg acgagcgtga    720
caccacgatg cctgtagcaa tggcaacaac gttgcgcaaa ctattaactg gcgaactact    780
tactctagct tcccggcaac aattaataga ctggatggag gcggataaag ttgcaggacc    840
acttctgcgc tcggcccttc cggctggctg gtttattgct gataaatctg gagccggtga    900
gcgtgggtct cgcggtatca ttgcagcact ggggccagat ggtaagccct cccgtatcgt    960
agttatctac acgacgggca gtcaggcaac tatggatgaa cgaaatagac agatcgctga   1020
gataggtgcc tcactgatta agcattggta actgtcagac caagtttact catatatact   1080
ttagattgat ttaaaacttc atttttaatt taaaaggatc taggtgaaga tcctttttga   1140
taatctcatg accaaaatcc cttaacgtga gttttcgttc cactgagcgt cagaccccgt   1200
agaaaagatc aaaggatctt cttgagatcc tttttttctg cgcgtaatct gctgcttgca   1260
aacaaaaaaa ccaccgctac cagcggtggt ttgtttgccg gatcaagagc taccaactct   1320
ttttccgaag gtaactggct tcagcagagc gcagatacca aatactgtcc ttctagtgta   1380
gccgtagtta ggccaccact tcaagaactc tgtagcaccg cctacatacc tcgctctgct   1440
aatcctgtta ccagtggctg ctgccagtgg cgataagtcg tgtcttaccg ggttggactc   1500
aagacgatag ttaccggata aggcgcagcg gtcgggctga acggggggtt cgtgcacaca   1560
gcccagcttg gagcgaacga cctacaccga actgagatac ctacagcgtg agcattgaga   1620
aagcgccacg cttcccgaag ggagaaaggc ggacaggtat ccggtaagcg gcagggtcgg   1680
aacaggagag cgcacgaggg agcttccagg gggaacgcc tggtatcttt atagtcctgt    1740
cgggtttcgc cacctctgac ttgagcgtcg atttttgtga tgctcgtcag gggggccgag   1800
cctatggaaa aacgccagca acgcggcctt tttacggttc ctggcctttt gctggccttt   1860
tgctcacatg ttctttcctg cgttatcccc tgattctgtg gataaccgta ttaccgcctt   1920
tgagtgagct gataccgctc gccgcagccg aacgaccgag cgcagcgagt cagtgagcga   1980
ggaagcggaa gagcgcccaa tacgcaaacc gcctctcccc gcgcgttggc cgattcatta   2040
atgcagctgg cacgacaggt ttcccgactg gaaagcgggc agtgagcgca acgcaattaa   2100
tgtgagttac ctcactcatt aggcacccca ggctttacac tttatgcttc cggctcctat   2160
gttgtgtgga attgtgagcg gataacaatt tcacacagga aacagctatg accatgatta   2220
cgccaagctc ggaattaacc ctcactaaag ggaacaaaag ctgggtaccg ggccccccct   2280
cgaggtcgac ggtatcgata agcttgatat cgaattcctg cagcccgggg gatccactag   2340
tctcgagctc ttcaactcaa gacgcacaga tattataaca tctgcataat aggcatttgc   2400
aagaattact cgtgagtaag gaaagagtga ggaactatcg catacctgca tttaaagatg   2460
```

-continued

```
ccgatttggg cgcgaatcct ttattttggc ttcaccctca tactattatc agggccagaa   2520
aaaggaagtg tttccctcct tcttgaattg atgttaccct cataaagcac gtggcctctt   2580
atcgagaaag aaattaccgt cgctcgtgat ttgtttgcaa aaagaacaaa actgaaaaaa   2640
cccagacacg ctcgacttcc tgtcttccta ttgattgcag cttccaattt cgtcacacaa   2700
caaggtccta gcgacggctc acaggttttg taacaagcaa tcgaaggttc tggaatggcg   2760
ggaaagggtt tagtaccaca tgctatgatg cccactgtga tctccagagc aaagttcgtt   2820
cgatcgtact gttactctct ctctttcaaa cagaattgtc cgaatcgtgt gacaacaaca   2880
gcctgttctc acacactctt ttcttctaac caagggggtg gtttagttta gtagaacctc   2940
gtgaaactta catttacata tatataaact tgcataaatt ggtcaatgca agaaatacat   3000
atttggtctt ttctaattcg tagtttttca agttcttaga tgctttcttt ttctcttttt   3060
tacagatcat caaggaagta attatctact ttttacaaca aatatatcta gaaaatgtct   3120
acccaacaaa ccatgaccgt tgacgaacac atcaaccaat tagttagaaa ggctcaagtt   3180
gctttgaagg aatacttgaa gccagaatac acccaagaaa agatcgacta catcgttaag   3240
aaggcttctg ttgctgcttt ggaccaacac tgtgctttgg ctgctgctgc tgttgaagaa   3300
accggtagag gtatcttcga agacaaggct accaagaaca tcttcgcttg tgaacacgtt   3360
acccacgaaa tgagacacgc taagaccgtt ggtatcatca acgttgaccc attgtacggt   3420
atcaccgaaa tcgctgaacc agttggtgtt gtttgtggtg ttaccccagt taccaaccca   3480
acctctaccg ctatcttcaa gtctttgatc tctatcaaga ccagaaaccc aatcgttttc   3540
tctttccacc catctgcttt gaagtgttct attatggctg ctaaaatcgt tagagacgct   3600
gctatcgctg ctggtgctcc agaaaactgt atccaatgga tcgaattcgg tggtatcgaa   3660
gcttctaaca agttgatgaa ccacccaggt gttgctacta tcttggctac cggtggtaac   3720
gctatggtta aggctgcata ctcttctggt aagccagctt tgggtgttgg tgctggtaac   3780
gttccaacct acatcgaaaa gacctgtaac atcaagcaag ctgctaacga cgttgttatg   3840
tctaagtctt tcgacaacgg tatgatctgt gcttctgaac aagctgctat catcgacaag   3900
gaaatctacg accaagttgt tgaagaaatg aagaccttgg gtgcttactt catcaacgaa   3960
gaagaaaagg ctaagttgga aaagttcatg ttcggtgtta acgcttactc tgctgacgtt   4020
aacaacgcta gattgaaccc aaagtgtcca ggtatgtctc cacaatggtt cgctgaacaa   4080
gttggtatca aggtaccaga agactgtaac atcatctgtg ctgtttgtaa ggaagttggt   4140
ccaaacgaac cattgaccag agaaaagttg tctccagttt tggctatctt gaaagctgaa   4200
aacacccaag acggtatcga caaggctgaa gctatggttg aatttaacgg tagaggtcac   4260
tctgctgcta tccactctaa cgacaaggct gttgttgaaa agtacgcttt gaccatgaag   4320
gcttgtagaa tcttgcacaa caccccatct tctcaaggtg gtatcggttc tatctacaac   4380
tacatctggc catctttcac cttgggttgt ggttcttacg gtggtaactc tgtttctgct   4440
aacgttacct accacaactt gttgaacatc aagagattgg ctgacagaag aaacaacttg   4500
caatggttca gagttccacc aaagatcttc ttcgaaccac actctatcag atacttggct   4560
gaattgaagg aattgtctaa gatcttcatc gtttctgaca gaatgatgta caagttgggt   4620
tacgttgaca gagttatgga cgttttgaag agaagatcta acgaagttga aatcgaaatc   4680
ttcatcgacg ttgaaccaga cccatctatc caaaccgttc aaaagggttt ggctgttatg   4740
aacaccttcg gtccagacaa catcatcgct atcggtggtg gttctgctat ggacgctgct   4800
aagatcatgt ggttgttgta cgaacaccca gaagctgact tcttcgctat gaagcaaaag   4860
```

```
ttcatcgact tgagaaagag agctttcaag ttcccaacca tgggtaagaa ggctagattg   4920
atctgtatcc caaccacctc tggtaccggt tctgaagtta ccccattcgc tgttatctct   4980
gaccacgaaa ccggtaagaa gtacccattg gctgactact ctttgacccc atctgttgct   5040
atcgttgacc caatgttcac catgtctttg ccaaagagag ctatcgctga caccggtttg   5100
gacgttttgg ttcacgctac cgaagcttac gtttctgtta tggctaacga atacaccgac   5160
ggtttggcta gagaagctgt taagttggtt tttgaaaact tgttgaagtc ttacaacggt   5220
gacttggaag ctagagaaaa gatgcacaac gctgctacca tcgctggtat ggctttcgct   5280
tctgctttct tgggtatgga ccactctatg gctcacaagg ttggtgctgc tttccacttg   5340
ccacacggta gatgtgttgc tgttttgttg ccacacgtta tcagatacaa cggtcaaaag   5400
ccaagaaagt tggctatgtg gccaaagtac aacttctaca aggctgacca aagatacatg   5460
gaattggctc aaatggttgg tttgaagtgt aacaccccag ctgaaggtgt tgaagctttc   5520
gctaaggctt gtgaagaatt gatgaaggct accgaaacca tcaccggttt caagaaggct   5580
aacatcgacg aagctgcttg gatgtctaag gttccagaaa tggctttgtt ggctttcgaa   5640
gaccaatgtt ctccagctaa cccaagagtt ccaatggtta aggacatgga aaagatcttg   5700
aaggctgctt actacccaat cgcttagctt aagcgcgcga atttcttatg atttatgatt   5760
tttattatta aataagttat aaaaaaaata agtgtataca aattttaaag tgactcttag   5820
gttttaaaac gaaaattctt attcttgagt aactctttcc tgtaggtcag gttgctttct   5880
caggtatagc atgaggtcgc tcttattgac cacacctcta ccggcatgcc gagcaaatgc   5940
ctgcaaatcg ctccccattt cacccaattg tagatatgct aactccagca atgagttgat   6000
gaatctcggt gtgtatttta tgtcctcaga ggacaacacc tgttgtaatc gttcttccac   6060
acgtacgaag ctaaaagggc gaattctgca gatatccatc acactggcgg ccgcatgcta   6120
gctccggatt atcgatgata agctgtcaaa gatgagaatt aattccacgg actatagact   6180
atactagata ctccgtctac tgtacgatac acttccgctc aggtccttgt cctttaacga   6240
ggccttacca ctcttttgtt actctattga tccagctcag caaaggcagt gtgatctaag   6300
attctatctt cgcgatgtag taaaactagc tagaccgaga aagagactag aaatgcaaaa   6360
ggcacttcta caatggctgc catcattatt atccgatgtg acgctgcagc ttctcaatga   6420
tattcgaata cgctttgagg agatacagcc taatatccga caaactgttt tacagattta   6480
cgatcgtact tgttacccat cattgaattt tgaacatccg aacctgggag ttttccctga   6540
aacagatagt atatttgaac ctgtataata atatatagtc tagcgcttta cggaagacaa   6600
tgtatgtatt tcggttcctg gagaaactat tgcatctatt gcataggtaa tcttgcacgt   6660
cgcatccccg gttcattttc tgcgtttcca tcttgcactt caatagcata tctttgttaa   6720
cgaagcatct gtgcttcatt ttgtagaaca aaaatgcaac gcgagagcgc taatttttca   6780
aacaaagaat ctgagctgca tttttacaga acagaaatgc aacgcgaaag cgctatttta   6840
ccaacgaaga atctgtgctt catttttgta aaacaaaaat gcaacgcgac gagagcgcta   6900
atttttcaaa caaagaatct gagctgcatt tttacagaac agaaatgcaa cgcgagagcg   6960
ctattttacc aacaaagaat ctatacttct tttttgttct acaaaaatgc atcccgagag   7020
cgctattttt ctaacaaagc atcttagatt acttttttc tcctttgtgc gctctataat    7080
gcagtctctt gataactttt tgcactgtag gtccgttaag gttagaagaa ggctactttg   7140
gtgtctattt tctcttccat aaaaaaagcc tgactccact tcccgcgttt actgattact   7200
```

-continued agcgaagctg cgggtgcatt ttttcaagat aaaggcatcc ccgattatat tctataccga 7260
tgtggattgc gcatactttg tgaacagaaa gtgatagcgt tgatgattct tcattggtca 7320
gaaaattatg aacggtttct tctattttgt ctctatatac tacgtatagg aaatgtttac 7380
attttcgtat tgttttcgat tcactctatg aatagttctt actacaattt ttttgtctaa 7440
agagtaatac tagagataaa cataaaaaat gtagaggtcg agtttagatg caagttcaag 7500
gagcgaaagg tggatgggta ggttatatag ggatatagca cagagatata tagcaaagag 7560
atacttttga gcaatgtttg tggaagcggt attcgcaatg ccggctttcc ccgtcaagct 7620
ctaaatcggg ggctcccttt agggttccga tttagtgctt tacggcacct cgaccccaaa 7680
aaacttgatt agggtgatgg ttcacgtagt gggccatcgc cctgatagac ggtttttcgc 7740
cctttgacgt tggagtccac gttctttaat agtggactct tgttccaaac tggaacaaca 7800
ctcaacccta tctcggtcta ttcttttgat ttataaggga ttttgccgat ttcggcctat 7860
tggttaaaaa atgagctgat ttaacaaaaa tttaacgcga attttaacaa aatattaacg 7920
tttacaattt cctgatgcgg tattttctcc ttacgcatct gtgcggtatt tcacaccgca 7980
tatgatccgt cgagttcaag agaaaaaaaa agaaaaagca aaaagaaaaa aggaaagcgc 8040
gcctcgttca gaatgacacg tatagaatga tgcattacct tgtcatcttc agtatcatac 8100
tgttcgtata catacttact gacattcata ggtatacata tatacacatg tatatatatc 8160
gtatgctgca gctttaaata atcggtgtca ctacataaga acacctttgg tggagggaac 8220
atcgttggta ccattgggcg aggtggcttc tcttatggca accgcaagag ccttgaacgc 8280
actctcacta cggtgatgat cattcttgcc tcgcagacaa tcaacgtgga gggtaattct 8340
gctagcctct gcaaagcttt caagaaaatg cgggatcatc tcgcaagaga gatctcctac 8400
tttctccctt tgcaaaccaa gttcgacaac tgcgtacggc ctgttcgaaa gatctaccac 8460
cgctctggaa agtgcctcat ccaaaggcgc aaatcctgat ccaaaccttt ttactccacg 8520
cgccagtagg gcctctttaa aagcttgacc gagagcaatc ccgcagtctt cagtggtgtg 8580
atggtcgtct atgtgtaagt caccaatgca ctcaacgatt agcgaccagc cggaatgctt 8640
ggccagagca tgtatcatat ggtccagaaa ccctatacct gtgtggacgt taatcacttg 8700
cgattgtgtg gcctgttctg ctactgcttc tgcctctttt tctgggaaga tcgagtgctc 8760
tatcgctagg ggaccaccct ttaaagagat cgcaatctga atcttggttt catttgtaat 8820
acgctttact agggctttct gctctgtcat ctttgccttc gtttatcttg cctgctcatt 8880
ttttagtata ttcttcgaag aaatcacatt actttatata atgtataatt cattatgtga 8940
taatgccaat cgctaagaaa aaaaaagagt catccgctag gtggaaaaaa aaaaatgaaa 9000
atcattaccg aggcataaaa aaatatagag tgtactagag gaggccaaga gtaatagaaa 9060
aagaaaattg cgggaaagga ctgtgttatg acttccctga ctaatgccgt gttcaaacga 9120
tacctggcag tgactcctag cgctcaccaa gctcttaaaa cggaattatg gtgcactctc 9180
agtacaatct gctctgatgc cgcatagtta agccagcccc gacacccgcc aacacccgct 9240
gacgcgccct gacgggcttg tctgctcccg gcatccgctt acagacaagc tgtgaccgtc 9300
tccgggagct gcatgtgtca gaggttttca ccgtcatcac cgaaacgcgc ga 9352

<210> SEQ ID NO 32
<211> LENGTH: 29
<212> TYPE: DNA
<213> ORGANISM: Artificial
<220> FEATURE:
<223> OTHER INFORMATION: Primer GPD2uf

<400> SEQUENCE: 32
ggtaccagat cttttgcggc gaggtgccg 29

<210> SEQ ID NO 33
<211> LENGTH: 42
<212> TYPE: DNA
<213> ORGANISM: Artificial
<220> FEATURE:
<223> OTHER INFORMATION: Primer GPD2ur

<400> SEQUENCE: 33
tctagactta aggaatgtgt atcttgttaa tcttctgaca gc 42

<210> SEQ ID NO 34
<211> LENGTH: 28
<212> TYPE: DNA
<213> ORGANISM: Artificial
<220> FEATURE:
<223> OTHER INFORMATION: Primer GPD2df

<400> SEQUENCE: 34
ctcgagatag tctacaacaa cgtccgca 28

<210> SEQ ID NO 35
<211> LENGTH: 39
<212> TYPE: DNA
<213> ORGANISM: Artificial
<220> FEATURE:
<223> OTHER INFORMATION: Primer GPD2dr

<400> SEQUENCE: 35
ccatggagat ctgcagtgaa aaagctcgaa gaaacagct 39

<210> SEQ ID NO 36
<211> LENGTH: 4397
<212> TYPE: DNA
<213> ORGANISM: Artificial
<220> FEATURE:
<223> OTHER INFORMATION: pRN594

<400> SEQUENCE: 36
gacgacggcg acctggcggg cttcgtggtc gtctcgtact ccggctggaa ccgccggctg 60
accgtcgagg acatcgaggt cgccccggag caccgggggc acggggtcgg gcgcgcgttg 120
atggggctcg cgacggagtt cgcccgcgag cggggcgccg ggcacctctg gctggaggtc 180
accaacgtca acgcaccggc gatccacgcg taccggcgga tggggttcac cctctgcggc 240
ctggacaccg ccctgtacga cggcaccgcc tcggacggcg agcaggcgct ctacatgagc 300
atgccctgcc cctagtactg acaataaaaa gattcttgtt ttcaagaact tgtcatttgt 360
atagtttttt tatattgtag ttgttctatt ttaatcaaat gttagcgtga tttatatttt 420
ttttcgcctc gacatcatct gcccagatgc gaagttaagt gcgcagaaag taatatcatg 480
cgtcaatcgt atgtgaatgc tggtcgctat actgctgtcg attcgatact aacgccgcca 540
tccagtgtcg acggatccta ggtgtacagg gcccaaaagg gcgaattctg cagatatcca 600
tcacactggc ggccgctcga gatagtctac aacaacgtcc gcatggaaga cctaccggag 660
atgattgaag agctagacat cgatgacgaa tagacactct cccccccct ccccctctga 720 tctttcctgt tgcctctttt tcccccaacc aatttatcat tatacacaag ttctacaact 780
actactagta acattactac agttattata attttctatt ctctttttct ttaagaatct 840

-continued

```
atcattaacg ttaatttcta tatatacata actaccatta tacacgctat tatcgtttac    900
atatcacatc accgttaatg aaagatacga caccctgtac actaacacaa ttaaataatc    960
gccataacct tttctgttat ctatagccct taaagctgtt tcttcgagct tttcactgc    1020
agatctccat ggcgatgcct gcttgccgaa tatcatggtg gaaaatggcc gcttttctgg   1080
attcatcgac tgtggccggc tgggtgtggc ggaccgctat caggacatag cgttggctac   1140
ccgtgatatt gctgaagagc ttggcggcga atgggctgac cgcttcctcg tgctttacgg   1200
tatcgccgct cccgattcgc agcgcatcgc cttctatcgc cttcttgacg agttcttctg   1260
aattgaaaaa ggaagagtat gagtattcaa catttccgtg tcgcccttat tccctttttt   1320
gcggcatttt gccttcctgt ttttgctcac ccagaaacgc tggtgaaagt aaaagatgct   1380
gaagatcagt tgggtgcacg agtgggttac atcgaactgg atctcaacag cggtaagatc   1440
cttgagagtt ttcgccccga agaacgtttt ccaatgatga gcacttttaa agttctgcta   1500
tgtggcgcgg tattatcccg tattgacgcc gggcaagagc aactcggtcg ccgcatacac   1560
tattctcaga atgacttggt tgagtactca ccagtcacag aaaagcatct tacggatggc   1620
atgacagtaa gagaattatg cagtgctgcc ataaccatga gtgataacac tgcggccaac   1680
ttacttctga caacgatcgg aggaccgaag gagctaaccg cttttttgca caacatgggg   1740
gatcatgtaa ctcgccttga tcgttgggaa ccggagctga atgaagccat accaaacgac   1800
gagcgtgaca ccacgatgcc tgtagcaatg gcaacaacgt tgcgcaaact attaactggc   1860
gaactactta ctctagcttc ccggcaacaa ttaatagact ggatggaggc ggataaagtt   1920
gcaggaccac ttctgcgctc ggcccttccg gctggctggt ttattgctga taaatctgga   1980
gccggtgagc gtgggtctcg cggtatcatt gcagcactgg ggccagatgg taagccctcc   2040
cgtatcgtag ttatctacac gacggggagt caggcaacta tggatgaacg aaatagacag   2100
atcgctgaga taggtgcctc actgattaag cattggtaac tgtcagacca agtttactca   2160
tatatacttt agattgattt aaaacttcat ttttaattta aaaggatcta ggtgaagatc   2220
ctttttgata atctcatgac caaaatccct taacgtgagt tttcgttcca ctgagcgtca   2280
gaccccgtag aaaagatcaa aggatcttct tgagatcctt tttttctgcg cgtaatctgc   2340
tgcttgcaaa caaaaaaacc accgctacca gcggtggttt gtttgccgga tcaagagcta   2400
ccaactcttt ttccgaaggt aactggcttc agcagagcgc agataccaaa tactgttctt   2460
ctagtgtagc cgtagttagg ccaccacttc aagaactctg tagcaccgcc tacatacctc   2520
gctctgctaa tcctgttacc agtggctgct gccagtggcg ataagtcgtg tcttaccggg   2580
ttggactcaa gacgatagtt accggataag gcgcagcggt cgggctgaac ggggggttcg   2640
tgcacacagc ccagcttgga gcgaacgacc tacaccgaac tgagatacct acagcgtgag   2700
ctatgagaaa gcgccacgct tcccgaaggg agaaaggcgg acaggtatcc ggtaagcggc   2760
agggtcggaa caggagagcg cacgagggag cttccagggg gaaacgcctg gtatctttat   2820
agtcctgtcg ggtttcgcca cctctgactt gagcgtcgat ttttgtgatg ctcgtcaggg   2880
gggcggagcc tatggaaaaa cgccagcaac gcggcctttt tacggttcct ggccttttgc   2940
tggccttttg ctcacatgtt ctttcctgcg ttatcccctg attctgtgga taaccgtatt   3000
accgcctttg agtgagctga taccgctcgc cgcagccgaa cgaccgagcg cagcgagtca   3060
gtgagcgagg aagcggaaga gcgcccaata cgcaaaccgc ctctccccgc gcgttggccg   3120
attcattaat gcagctggca cgacaggttt cccgactgga aagcgggcag tgagcgcaac   3180
gcaattaatg tgagttagct cactcattag gcaccccagg ctttacactt tatgcttccg   3240
```

```
gctcgtatgt tgtgtggaat tgtgagcgga taacaatttc acacaggaaa cagctatgac   3300

catgattacg ccaagctatt taggtgacac tatagaatac tcaagctatg catcaagctt   3360

ggtaccagat cttttgcggc gaggtgccga tgggttgctg aggggaagag tgtttagctt   3420

acggacctat tgccattgtt attccgatta atctattgtt cagcagctct tctctaccct   3480

gtcattctag tatttttttt tttttttttt ggttttactt tttttcttc ttgccttttt   3540

ttcttgttac ttttttcta gtttttttc cttccactaa gctttttcct tgatttatcc   3600

ttgggttctt ctttctactc ctttagattt tttttttata tattaatttt taagtttatg   3660

tattttggta gattcaattc tctttccctt tccttttcct tcgctcccct tccttatcaa   3720

tgcttgctgt cagaagatta acaagataca cattccttaa ggcctcgtcc ccgccgggtc   3780

acccggccag cgacatggag gcccagaata ccctccttga cagtcttgac gtgcgcagct   3840

caggggcatg atgtgactgt cgcccgtaca tttagcccat acatccccat gtataatcat   3900

ttgcatccat acattttgat ggccgcacgg cgcgaagcaa aaattacggc tcctcgctgc   3960

agacctgcga gcagggaaac gctcccctca cagacgcgtt gaattgtccc cacgccgcgc   4020

ccctgtagag aaatataaaa ggttaggatt tgccactgag gttcttcttt catatacttc   4080

cttttaaaat cttgctagga tacagttctc acatcacatc cgaacataaa caaccatgta   4140

aaatgaccac tcttgacgac acggcttacc ggtaccgcac cagtgtcccg gggggacgccg   4200

aggccatcga ggcactggat gggtccttca ccaccgacac cgtcttccgc gtcaccgcca   4260

ccggggacgg cttcaccctg cgggaggtgc cggtggaccc gcccctgacc aaggtgttcc   4320

ccgacgacga atcggacgac gaatcggacg ccggggagga cggcgacccg gactcccgga   4380

cgttcgtcgc gtacggg                                                  4397
```

<210> SEQ ID NO 37
<211> LENGTH: 14200
<212> TYPE: DNA
<213> ORGANISM: Artificial
<220> FEATURE:
<223> OTHER INFORMATION: pRN957

<400> SEQUENCE: 37

```
gacgaaaggg cctcgtgata cgcctatttt tataggttaa tgtcatgata ataagacgtc     60

aggtggcact tttcggggaa atgtgcgcgg aacccctatt tgtttatttt tctaaataca    120

ttcaaatatg tatccgctca tgagacaata accctgataa atgcttcaat aatattgaaa    180

aaggaagagt atgagtattc aacatttccg tgtcgccctt attccctttt ttgcggcatt    240

ttgccttcct gtttttgctc acccagaaac gctggtgaaa gtaaaagatg ctgaagatca    300

gttgggtgca cgagtgggtt acatcgaact ggatctcaac agcggtaaga tccttgagag    360

ttttcgcccc gaagaacgtt ttccaatgat gagcactttt aaagttctgc tatgtggcgc    420

ggtattatcc cgtattgacg ccgggcaaga gcaactcggt cgccgcatac actattctca    480

gaatgacttg gttgagtact caccagtcac agaaaagcat cttacggatg gcatgacagt    540

aagagaatta tgcagtgctg ccataaccat gagtgataac actgcggcca acttacttct    600

gacaacgatc ggaggaccga aggagctaac cgcttttttt cacaacatgg gggatcatgt    660

aactcgcctt gatcgttggg aaccggagct gaatgaagcc ataccaaacg acgagcgtga    720

caccacgatg cctgtagcaa tggcaacaac gttgcgcaaa ctattaactg gcgaactact    780

tactctagct tcccggcaac aattaataga ctggatggag gcggataaag ttgcaggacc    840
```

-continued

```
acttctgcgc tcggcccttc cggctggctg gtttattgct gataaatctg gagccggtga    900
gcgtgggtct cgcggtatca ttgcagcact ggggccagat ggtaagccct cccgtatcgt    960
agttatctac acgacgggca gtcaggcaac tatggatgaa cgaaatagac agatcgctga   1020
gataggtgcc tcactgatta agcattggta actgtcagac caagtttact catatatact   1080
ttagattgat ttaaaacttc atttttaatt taaaaggatc taggtgaaga tcctttttga   1140
taatctcatg accaaaatcc cttaacgtga gttttcgttc cactgagcgt cagaccccgt   1200
agaaaagatc aaaggatctt cttgagatcc tttttttctg cgcgtaatct gctgcttgca   1260
aacaaaaaaa ccaccgctac cagcggtggt ttgtttgccg gatcaagagc taccaactct   1320
ttttccgaag gtaactggct tcagcagagc gcagatacca aatactgtcc ttctagtgta   1380
gccgtagtta ggccaccact tcaagaactc tgtagcaccg cctacatacc tcgctctgct   1440
aatcctgtta ccagtggctg ctgccagtgg cgataagtcg tgtcttaccg ggttggactc   1500
aagacgatag ttaccggata aggcgcagcg gtcgggctga acggggggtt cgtgcacaca   1560
gcccagcttg gagcgaacga cctacaccga actgagatac ctacagcgtg agcattgaga   1620
aagcgccacg cttcccgaag ggagaaaggc ggacaggtat ccggtaagcg gcagggtcgg   1680
aacaggagag cgcacgaggg agcttccagg ggggaacgcc tggtatcttt atagtcctgt   1740
cgggtttcgc cacctctgac ttgagcgtcg atttttgtga tgctcgtcag gggggccgag   1800
cctatggaaa aacgccagca acgcggcctt tttacggttc ctggcctttt gctggccttt   1860
tgctcacatg ttctttcctg cgttatcccc tgattctgtg gataaccgta ttaccgcctt   1920
tgagtgagct gataccgctc gccgcagccg aacgaccgag cgcagcgagt cagtgagcga   1980
ggaagcggaa gagcgcccaa tacgcaaacc gcctctcccc gcgcgttggc cgattcatta   2040
atgcagctgg cacgacaggt ttcccgactg gaaagcgggc agtgagcgca acgcaattaa   2100
tgtgagttac ctcactcatt aggcacccca ggctttacac tttatgcttc cggctcctat   2160
gttgtgtgga attgtgagcg gataacaatt tcacacagga aacagctatg accatgatta   2220
cgccaagctc ggaattaacc ctcactaaag ggaacaaaag ctgggtaccg ggccccccct   2280
cgaggtcgag cttaagacgc gtttcttctt cagattccct catggagaaa gtgcggcaga   2340
tgtatatgac agagtcgcca gtttccaaga gactttattc aggcacttcc atgataggca   2400
agagagaaga cccagagatg ttgttgtcct agttacacat ggtatttatt ccagagtatt   2460
cctgatgaaa tggtttagat ggacatacga agagtttgaa tcgtttacca atgttcctaa   2520
cgggagcgta atggtgatgg aactggacga atccatcaat agatacgtcc tgaggaccgt   2580
gctacccaaa tggactgatt gtgagggaga cctaactaca tagtgtttaa agattacgga   2640
tatttaactt acttagaata atgccatttt tttgagttat aataatccta cgttagtgtg   2700
agcgggattt aaactgtgag gaccttaata cattcagaca cttctgcggt atcaccctac   2760
ttattccctt cgagattata tctaggaacc catcaggttg gtggaagatt acccgttcta   2820
agacttttca gcttcctcta ttgatgttac acctggacac ccctttctg gcatccagtt   2880
tttaatcttc agtggcatgt gagattctcc gaaattaatt aaagcaatca cacaattctc   2940
tcggatacca cctcggttga aactgacagg tggtttgtta cgcatgctaa tgcaaaggag   3000
cctatatacc tttggctcgg ctgctgtaac agggaatata aagggcagca taatttagga   3060
gtttagtgaa cttgcaacat ttactatttt cccttcttac gtaaatattt ttctttttaa   3120
ttctaaatca atctttttca attttttgtt tgtattcttt tcttgcttaa atctataact   3180
acaaaaaaca catacataaa tctagaaaaa tgtctcaatt cttcttcaac cagagaaccc   3240
```

```
acttggtttc tgacgttatc gacggtgcta tcatcgcttc accatggaac aatttggcta   3300
gattggaatc tgacccagct atcagaatcg ttgttagaag agacttgaac aagaacaacg   3360
ttgctgttat ctctggtggt ggttctggtc acgaaccagc tcacgttggt ttcatcggta   3420
agggtatgtt gaccgctgct gtttgtggtg acgttttcgc ttctccatct gttgacgctg   3480
ttttgactgc tatccaagct gttaccggtg aagctggttg tttgttgatc gttaagaact   3540
acaccggtga cagattgaac ttcggtttgg ctgctgaaaa ggctagaaga ttgggttaca   3600
acgttgaaat gttgatcgtt ggtgacgaca tctctttgcc agacaacaag cacccaagag   3660
gtatcgctgg taccatcttg gttcacaaga tcgctggtta cttcgctgaa agaggttaca   3720
acttagctac cgttttgaga gaagctcaat acgctgcttc taacaccttc tctttgggtg   3780
ttgctttgtc ttcttgtcac ttgccacaag aaaccgacgc tgctccaaga caccacccag   3840
gtcacgctga attgggtatg ggtatccacg gtgaaccagg tgcttctgtt atcgacaccc   3900
aaaactctgc tcaagttgtt aacttgatgg ttgacaagtt gttggctgct ttgccagaaa   3960
ccggtagatt ggctgttatg atcaacaact tgggtggtgt ttctgttgct gaaatggcta   4020
tcatcaccag agaattggct tcttctccat tgcactcaag aatcgactgg ttgatcggtc   4080
cagcttcttt ggtaaccgct ttggacatga agggtttctc tttgaccgct atcgttttgg   4140
aagaatctat cgaaaaggct ttgttgaccg aagttgaaac ctctaactgg ccaaccccag   4200
ttccaccaag agaaatcacc tgtgttgttt cttctcacgc ttctgctaga gttgaattcc   4260
aaccatctgc taacgctttg gttgctggta tcgttgaatt ggttaccgct accttgtctg   4320
acttggaaac ccacttgaac gctttggacg ctaaggttgg tgacggtgac accggttcta   4380
ccttcgctgc tgctgctaga gaaatcgctt ctttgttgca cagacaacaa ttgccattga   4440
acaacttggc taccttgttc gctttgatcg gtgaaagatt gaccgttgtt atgggtggtt   4500
cttctggtgt tttgatgtct atcttcttca ccgctgctgg tcaaaagttg gaacaaggtg   4560
ctaacgttgt tgaagctttg aacaccggtt tggctcaaat gaagttctac ggtggtgctg   4620
acgaaggtga cagaaccatg atcgacgctt tgcaaccagc tttgacctct ttgttggctc   4680
aaccaaagaa cttgcaagct gctttcgacg ctgctcaagc tggtgctgaa agaacctgtt   4740
tgtcttctaa ggctaacgct ggtagagctt cttacttgtc ttctgaatct ttgttgggta   4800
acatggaccc aggtgctcaa agattggcta tggttttcaa ggctttggct gaatctgaat   4860
tgggttaata aggtcgagac aaatcgctct taaatatata cctaaagaac attaaagcta   4920
tattataagc aaagatacgt aaattttgct tatattatta tacacatatc atatttctat   4980
atttttaaga tttggttata taatgtacgt aatgcaaagg aaataaattt tatacattat   5040
tgaacagcgt ccaagtaact acattatgtg cactaatagt ttagcgtcgt gaagacttta   5100
ttgtgtcgcg aaaagtaaaa attttaaaaa ttagagcacc ttgaacttgc gaaaaaggtt   5160
ctcatcaact gtttaaaacg tacgcctagg aagccttcga gcgtcccaaa accttctcaa   5220
gcaaggtttt cagtataatg ttacatgcgt acacgcgttt gtacagaaaa aaaagaaaaa   5280
tttgaaatat aaataacgtt cttaatacta acataactat taaaaaaaat aaatagggac   5340
ctagacttca ggttgtctaa ctccttcctt ttcggttaga gcggatgtgg gaggagggcg   5400
tgaatgtaag cgtgacataa ctaattacat gatatcgaca aaggaaaagg ggcgcgcctt   5460
attcccattc ttgtaggaat ctttgaccgt attggtcagc aaccaacaaa gcagcgtaaa   5520
cttggtctgg ggtagcacca cctggcatgt tgtggatggt ttcaccttca gcacaagcag   5580
```

-continued

```
cttcagcaac gattctcatc ttagctggaa cgtcttcctt gatgtccaat tgagccaagg   5640
tgattggcaa accaacagcg tgagacaaag cagcaacggt ttcgatttct tcaactggag   5700
cgttttccaa aaccaattgg gtcaaggtac cgaaagcaac cttttcaccg tggtagtagt   5760
ggtgagcgtc tgggatagcg gtcaaaccgt tgtgaacagc gtgagcagca gccaaaccac   5820
cagattcgaa accaacacca gacaagtagg tgttagcttc gataactctt tccaaagctg   5880
gggtaacaac gtgttgttca gcagccaaca tagccttttc accttcttcc aacaaggtgt   5940
tgtaacacaa ttcagccaaa gccaaagcag cttgggtaca cttaccacca gccatggtgg   6000
tagcaccaga tctagaacaa gctctagctt cgaaccaggt agccaaagcg tcaccgatac   6060
cagctgccaa caatctagct ggagcaccag caacgatctt ggtgtcaacg ataaccatgt   6120
ttgggttgtt tggcaacaac aagtatctgt cgaattcacc ttcgtcggtg tagataacag   6180
acaaagcaga acatggagcg tcggtagaag cgatggttgg agcgatagca actggaacac   6240
ccatgaagtg agccaaagcc ttagcggtgt ccaaggtctt accaccaccg atacccaaga   6300
tagcaccaca ttgagcggtt tcagcgatac ctctcaatct gtcgatttcg ttttgagaac   6360
attcaccacc gaatggagcg atttcaacaa ccaaaccagc gtccttgaaa gacttttcaa   6420
cggtagattg agcgaaaccc aaaacgaact tgtcaccaac aaccaaccat ctttcagcca   6480
atggcttcaa gtattcaccc aatctgttga taacgtcagc accttggatg tacttacctg   6540
gagattggat gattctgtcc attttctgca gttaattcag taaattttcg atcttgggaa   6600
gaaaaaagca gtaagcgtga aaaatctaaa agctgatgta gtagaagatc ctattcttta   6660
acaaagattg accttttctt tttcttcttg gtttgagtag aaaggggaag gaagaataca   6720
agagagagga aaaaaaggaa gataaaaaga gagcgtgata taaatgaata tatattaaac   6780
aagagagatt gggaaggaaa ggatcaaaca aacccaaaaa tatttcaaaa aggagagaga   6840
gaggcgagtt tggtttcaaa acggtttatt tatttatgca agaggacgtg gaagaaaaag   6900
aagaaggaag aaaaaaattt gaaagaaaaa aacgcgtggc gggtaaagaa gaaaatggaa   6960
aatagaggcc gggtgacaga gaaatattga gggttaattg gaaaatatgt tagggtgagg   7020
catatgtttt taagggtttt gaggatccga taaggaagaa tgtaggttaa atgttgtgca   7080
ttaattgctg tggcagctta cccgcttccc cacacattta ctagtctcga gctcttcaac   7140
tcaagacgca cagatattat aacatctgca taataggcat ttgcaagaat tactcgtgag   7200
taaggaaaga gtgaggaact atcgcatacc tgcatttaaa gatgccgatt tgggcgcgaa   7260
tcctttattt tggcttcacc ctcatactat tatcagggcc agaaaaagga agtgtttccc   7320
tccttcttga attgatgtta ccctcataaa gcacgtggcc tcttatcgag aaagaaatta   7380
ccgtcgctcg tgatttgttt gcaaaaagaa caaaactgaa aaaacccaga cacgctcgac   7440
ttcctgtctt cctattgatt gcagcttcca atttcgtcac acaacaaggt cctagcgacg   7500
gctcacaggt tttgtaacaa gcaatcgaag gttctggaat ggcgggaaag ggtttagtac   7560
cacatgctat gatgcccact gtgatctcca gagcaaagtt cgttcgatcg tactgttact   7620
ctctctcttt caaacagaat tgtccgaatc gtgtgacaac aacagcctgt tctcacacac   7680
tcttttcttc taaccaaggg ggtggtttag tttagtagaa cctcgtgaaa cttacattta   7740
catatatata aacttgcata aattggtcaa tgcaagaaat acatatttgg tcttttctaa   7800
ttcgtagttt ttcaagttct tagatgcttt ctttttctct tttttacaga tcatcaagga   7860
agtaattatc tacttttttac aacaaatata tctagaaaat ggctgttacc aacgttgctg  7920
aattgaacgc tttggttgaa agggttaaga aggctcaaag agaatacgct tctttcaccc   7980
```

aagaacaagt tgacaagatc ttcagagctg ctgctttggc tgctgctgac gctagaatcc 8040
cattggctaa gatggctgtt gctgaatctg gtatgggtat cgttgaagac aaggttatca 8100
agaaccactt cgcttctgaa tacatctaca acgcttacaa ggacgaaaag acctgtggtg 8160
ttttgtcaga agacgacacc ttcggtacca tcaccatcgc tgaaccaatc ggtatcatct 8220
gtggtatcgt tccaaccacc aacccaacct ctaccgctat cttcaagtct ttgatctctt 8280
tgaagaccag aaacgctatc atcttctctc cacacccaag agctaaagac gctaccaaca 8340
aggctgctga catcgttttg caagctgcta tcgctgctgg tgctccaaag gacttgatcg 8400
gttggatcga ccaaccatct gttgaattgt ctaacgcttt gatgcaccac ccagacatca 8460
acttgatctt ggctaccggt ggtccaggta tggttaaggc tgcttactct tctggtaagc 8520
cagctatcgg tgttggtgct ggtaacaccc cagttgttat cgacgaaacc gctgacatca 8580
agagagctgt tgcttctgtt ttgatgtcta agaccttcga caacggtgtt atctgtgctt 8640
ctgaacaatc tgttgttgtt gttgactctg tttacgacgc tgttagagaa agattcgcta 8700
cccacggtgg ttacttgttg caaggtaagg aattgaaggc tgttcaagac gttatcttga 8760
agaacggtgc tttgaacgct gctatcgttg gtcaaccagc ttacaagatc gctgaattag 8820
ctggtttctc tgttccagaa aacaccaaga tcttgatcgg tgaagttacc gttgttgacg 8880
aatctgaacc attcgctcac gaaaagttgt ctccaacctt ggctatgtac agagctaagg 8940
acttcgaaga cgctgttgaa aaagctgaaa agttggttgc tatgggtggt attggtcaca 9000
cctcttgttt gtacaccgac caagacaacc aaccagctag agtttcttac ttcggtcaaa 9060
agatgaagac cgctagaatc ttgatcaaca ccccagcttc tcaaggtggt atcggtgact 9120
tgtacaactt caagttggct ccatctttga ccttgggttg tggttcttgg ggtggtaact 9180
ctatctctga aaacgttggt ccaaagcact tgatcaacaa gaagaccgtt gctaagagag 9240
ctgaaaacat gttgtggcac aagttgccaa aatctatcta cttcagaaga ggttctttgc 9300
caatcgcttt ggacgaagtt atcaccgacg gtcacaagag agctttgatc gttaccgaca 9360
gattcttgtt caacaacggt tacgctgacc aaatcacctc tgttttgaag gctgctggtg 9420
ttgaaaccga agttttcttc gaagttgaag ctgacccaac cttgtctatc gttagaaagg 9480
gtgctgaatt ggctaactct ttcaagccag acgttatcat cgctttgggt ggtggttctc 9540
caatggacgc tgctaagatc atgtgggtta tgtacgaaca cccagaaacc cacttcgaag 9600
aattggcttt gagattcatg gacatcagaa agagaatcta caagttccca aagatgggtg 9660
ttaaggctaa gatgatcgct gttaccacca cctctggtac cggttctgaa gttacccca t 9720
tcgctgttgt taccgacgac gctaccggtc aaaagtaccc attggctgac tacgctttga 9780
ccccagacat ggctatcgtt gacgctaact tggttatgga catgccaaag tctttgtgtg 9840
ctttcggtgg tttggacgct gttacccacg ctatggaagc ttacgtttct gttttggctt 9900
ctgaattctc tgacggtcaa gctttgcaag ctttgaagtt gttgaaggaa tacttgccag 9960
cttcttacca cgaaggttct aagaacccag ttgctagaga aagagttcac tctgctgcta 10020
ccatcgctgg tatcgctttc gctaacgctt tcttgggtgt ttgtcactct atggctcaca 10080
agttgggttc tcaattccac atcccacacg gtttggctaa cgctttgttg atctgtaacg 10140
ttatcagata caacgctaac gacaacccaa ccaagcaaac cgctttctct caatacgaca 10200
gaccacaagc tagaagaaga tacgctgaaa tcgctgacca cttgggtttg tctgctccag 10260
gtgacagaac cgctgcaaag atcgaaaagt tgttggcttg gttggaaacc ttgaaggctg 10320

-continued aattgggtat cccaaagtct atcagagaag ctggtgttca agaagctgac ttcttggcta 10380
acgttgacaa gttgtctgaa gacgctttcg acgaccaatg taccggtgct aacccaagat 10440
acccattgat ctctgaattg aagcaaatct tgttggacac ctactacggt agagactacg 10500
ttgaaggtga aaccgctgct aagaaggaag ctgctccagc taaggctgaa aagaaggcta 10560
agaagtctgc ttagcttaag cgcgcgaatt tcttatgatt tatgattttt attattaaat 10620
aagttataaa aaaaataagt gtatacaaat tttaaagtga ctcttaggtt ttaaaacgaa 10680
aattcttatt cttgagtaac tctttcctgt aggtcaggtt gctttctcag gtatagcatg 10740
aggtcgctct tattgaccac acctctaccg gcatgccgag caaatgcctg caaatcgctc 10800
cccatttcac ccaattgtag atatgctaac tccagcaatg agttgatgaa tctcggtgtg 10860
tattttatgt cctcagagga caacacctgt tgtaatcgtt cttccacacg tacgaagctt 10920
aaaagggcga attctgcaga tatccatcac actggcggcc gcatgctagc tccggattat 10980
cgatgataag ctgtcaaaga tgagaattaa ttccacggac tatagactat actagatact 11040
ccgtctactg tacgatacac ttccgctcag gtccttgtcc tttaacgagg ccttaccact 11100
cttttgttac tctattgatc cagctcagca aaggcagtgt gatctaagat tctatcttcg 11160
cgatgtagta aaactagcta gaccgagaaa gagactagaa atgcaaaagg cacttctaca 11220
atggctgcca tcattattat ccgatgtgac gctgcagctt ctcaatgata ttcgaatacg 11280
ctttgaggag atacagccta atatccgaca aactgtttta cagatttacg atcgtacttg 11340
ttacccatca ttgaattttg aacatccgaa cctgggagtt ttccctgaaa cagatagtat 11400
atttgaacct gtataataat atatagtcta gcgctttacg gaagacaatg tatgtatttc 11460
ggttcctgga gaaactattg catctattgc ataggtaatc ttgcacgtcg catccccggt 11520
tcattttctg cgtttccatc ttgcacttca atagcatatc tttgttaacg aagcatctgt 11580
gcttcatttt gtagaacaaa aatgcaacgc gagagcgcta atttttcaaa caaagaatct 11640
gagctgcatt tttacagaac agaaatgcaa cgcgaaagcg ctattttacc aacgaagaat 11700
ctgtgcttca tttttgtaaa acaaaaatgc aacgcgacga gagcgctaat tttcaaaca 11760
aagaatctga gctgcatttt tacagaacag aaatgcaacg cgagagcgct attttaccaa 11820
caaagaatct atacttcttt tttgttctac aaaaatgcat cccgagagcg ctatttttct 11880
aacaaagcat cttagattac tttttttctc ctttgtgcgc tctataatgc agtctcttga 11940
taactttttg cactgtaggt ccgttaaggt tagaagaagg ctactttggt gtctattttc 12000
tcttccataa aaaaagcctg actccacttc ccgcgtttac tgattactag cgaagctgcg 12060
ggtgcatttt ttcaagataa aggcatcccc gattatattc tataccgatg tggattgcgc 12120
atactttgtg aacagaaagt gatagcgttg atgattcttc attggtcaga aaattatgaa 12180
cggtttcttc tattttgtct ctatatacta cgtataggaa atgtttacat tttcgtattg 12240
ttttcgattc actctatgaa tagttcttac tacaattttt ttgtctaaag agtaatacta 12300
gagataaaca taaaaaatgt agaggtcgag tttagatgca agttcaagga gcgaaaggtg 12360
gatgggtagg ttatataggg atatagcaca gagatatata gcaaagagat acttttgagc 12420
aatgtttgtg gaagcggtat tcgcaatgcc ggctttcccc gtcaagctct aaatcggggg 12480
ctccctttag ggttccgatt tagtgcttta cggcacctcg accccaaaaa acttgattag 12540
ggtgatggtt cacgtagtgg gccatcgccc tgatagacgg tttttcgccc tttgacgttg 12600
gagtccacgt tctttaatag tggactcttg ttccaaactg gaacaacact caaccctatc 12660
tcggtctatt cttttgattt ataagggatt ttgccgattt cggcctattg gttaaaaaat 12720

```
gagctgattt aacaaaaatt taacgcgaat tttaacaaaa tattaacgtt tacaatttcc  12780

tgatgcggta ttttctcctt acgcatctgt gcggtatttc acaccgcata tgatccgtcg  12840

agttcaagag aaaaaaaaag aaaaagcaaa aagaaaaaag gaaagcgcgc ctcgttcaga  12900

atgacacgta tagaatgatg cattaccttg tcatcttcag tatcatactg ttcgtataca  12960

tacttactga cattcatagg tatacatata tacacatgta tatatatcgt atgctgcagc  13020

tttaaataat cggtgtcact acataagaac acctttggtg gagggaacat cgttggtacc  13080

attgggcgag gtggcttctc ttatggcaac cgcaagagcc ttgaacgcac tctcactacg  13140

gtgatgatca ttcttgcctc gcagacaatc aacgtggagg gtaattctgc tagcctctgc  13200

aaagctttca agaaaatgcg ggatcatctc gcaagagaga tctcctactt tctccctttg  13260

caaaccaagt tcgacaactg cgtacggcct gttcgaaaga tctaccaccg ctctggaaag  13320

tgcctcatcc aaaggcgcaa atcctgatcc aaaccttttt actccacgcg ccagtagggc  13380

ctctttaaaa gcttgaccga gagcaatccc gcagtcttca gtggtgtgat ggtcgtctat  13440

gtgtaagtca ccaatgcact caacgattag cgaccagccg gaatgcttgg ccagagcatg  13500

tatcatatgg tccagaaacc ctatacctgt gtggacgtta atcacttgcg attgtgtggc  13560

ctgttctgct actgcttctg cctctttttc tgggaagatc gagtgctcta tcgctagggg  13620

accacccttt aaagagatcg caatctgaat cttggtttca tttgtaatac gctttactag  13680

ggctttctgc tctgtcatct ttgccttcgt ttatcttgcc tgctcatttt ttagtatatt  13740

cttcgaagaa atcacattac tttatataat gtataattca ttatgtgata atgccaatcg  13800

ctaagaaaaa aaaagagtca tccgctaggt ggaaaaaaaa aaatgaaaat cattaccgag  13860

gcataaaaaa atatagagtg tactagagga ggccaagagt aatagaaaaa gaaaattgcg  13920

ggaaaggact gtgttatgac ttccctgact aatgccgtgt tcaaacgata cctggcagtg  13980

actcctagcg ctcaccaagc tcttaaaacg gaattatggt gcactctcag tacaatctgc  14040

tctgatgccg catagttaag ccagccccga cacccgccaa cacccgctga cgcgccctga  14100

cgggcttgtc tgctcccggc atccgcttac agacaagctg tgaccgtctc cgggagctgc  14160

atgtgtcaga ggttttcacc gtcatcaccg aaacgcgcga                        14200
```

<210> SEQ ID NO 38
<211> LENGTH: 3042
<212> TYPE: DNA
<213> ORGANISM: Artificial
<220> FEATURE:
<223> OTHER INFORMATION: pRNDAK

<400> SEQUENCE: 38

```
ggatccacta gtaacggccg ccagtgtgct ggaattcgcc cttctcgagc ttaagacgcg     60

tttcttcttc agattccctc atggagaaag tgcggcagat gtatatgaca gagtcgccag    120

tttccaagag actttattca ggcacttcca tgataggcaa gagagaagac ccagagatgt    180

tgttgtccta gttacacatg gtatttattc cagagtattc ctgatgaaat ggtttagatg    240

gacatacgaa gagtttgaat cgtttaccaa tgttcctaac gggagcgtaa tggtgatgga    300

actggacgaa tccatcaata gatacgtcct gaggaccgtg ctacccaaat ggactgattg    360

tgagggagac ctaactacat agtgtttaaa gattacggat atttaactta cttagaataa    420

tgccattttt ttgagttata ataatcctac gttagtgtga gcgggattta aactgtgagg    480

accttaatac attcagacac ttctgcggta tcaccctact tattcccttc gagattatat    540
```

```
ctaggaaccc atcaggttgg tggaagatta cccgttctaa gacttttcag cttcctctat    600
tgatgttaca cctggacacc ccttttctgg catccagttt ttaatcttca gtggcatgtg    660
agattctccg aaattaatta aagcaatcac acaattctct cggataccac ctcggttgaa    720
actgacaggt ggtttgttac gcatgctaat gcaaaggagc ctatatacct ttggctcggc    780
tgctgtaaca gggaatataa agggcagcat aatttaggag tttagtgaac ttgcaacatt    840
tactattttc ccttcttacg taaatatttt tctttttaat tctaaatcaa tctttttcaa    900
tttttgttt gtattctttt cttgcttaaa tctataacta caaaaaacac atacataaat    960
ctagaaaatg tccgctaaat cgtttgaagt cacagatcca gtcaattcaa gtctcaaagg   1020
gtttgccctt gctaacccct ccattacgct ggtccctgaa gaaaaaattc tcttcagaaa   1080
gaccgattcc gacaagatcg cattaatttc tggtggtggt agtggacatg aacctacaca   1140
cgccggtttc attggtaagg gtatgttgag tggcgccgtg gttggcgaaa tttttgcatc   1200
cccttcaaca aaacagattt taaatgcaat ccgtttagtc aatgaaaatg cgtctggcgt   1260
tttattgatt gtgaagaact acacaggtga tgttttgcat tttggtctgt ccgctgagag   1320
agcaagagcc ttgggtatta actgccgcgt tgctgtcata ggtgatgatg ttgcagttgg   1380
cagagaaaag ggtggtatgg ttggtagaag agcattggca ggtaccgttt tggttcataa   1440
gattgtaggt gccttcgcag aagaatattc tagtaagtat ggcttagacg gtacagctaa   1500
agtggctaaa attatcaacg acaatttggt gaccattgga tcttctttag accattgtaa   1560
agttcctggc aggaaattcg aaagtgaatt aaacgaaaaa caaatggaat tgggtatggg   1620
tattcataac gaacctggtg tgaaagtttt agaccctatt ccttctaccg aagacttgat   1680
ctccaagtat atgctaccaa aactattgga tccaaacgat aaggatagag cttttgtaaa   1740
gtttgatgaa gatgatgaag ttgtcttgtt agttaacaat ctcggcggtg tttctaattt   1800
tgttattagt tctatcactt ccaaaactac ggatttctta aaggaaaatt acaacataac   1860
cccggttcaa acaattgctg gcacattgat gacctccttc aatggtaatg ggttcagtat   1920
cacattacta aacgccacta aggctacaaa ggctttgcaa tctgattttg aggagatcaa   1980
atcagtacta gacttgttga acgcatttac gaacgcaccg ggctggccaa ttgcagattt   2040
tgaaaagact tctgccccat ctgttaacga tgacttgtta cataatgaag taacagcaaa   2100
ggccgtcggt acctatgact ttgacaagtt tgctgagtgg atgaagagtg gtgctgaaca   2160
agttatcaag agcgaaccgc acattacgga actagacaat caagttggtg atggtgattg   2220
tggttacact ttagtggcag gagttaaagg catcaccgaa aaccttgaca agctgtcgaa   2280
ggactcatta tctcaggcgg ttgcccaaat ttcagatttc attgaaggct caatgggagg   2340
tacttctggt ggtttatatt ctattctttt gtcgggtttt tcacacggat taattcaggt   2400
ttgtaaatca aaggatgaac ccgtcactaa ggaaattgtg gctaagtcac tcggaattgc   2460
attggatact ttatacaaat atacaaaggc aaggaaggga tcatccacca tgattgatgc   2520
tttagaacca ttcgttaaag aatttactgc atctaaggat ttcaataagg cggtaaaagc   2580
tgcagaggaa ggtgctaaat ccactgctac attcgaggcc aaatttggca gagcttcgta   2640
tgtcggcgat tcatctcaag tagaagatcc tggtgcagta ggcctatgtg agtttttgaa   2700
gggggttcaa agcgccttgt aagtcgagac aaatcgctct taaatatata cctaaagaac   2760
attaaagcta tattataagc aaagatacgt aaattttgct tatattatta tacacatatc   2820
atatttctat atttttaaga tttggttata taatgtacgt aatgcaaagg aaataaattt   2880
tatacattat tgaacagcgt ccaagtaact acattatgtg cactaatagt ttagcgtcgt   2940
```

gaagacttta ttgtgtcgcg aaaagtaaaa attttaaaaa ttagagcacc ttgaacttgc 3000
gaaaaaggtt ctcatcaact gtttaaaacg tacgaagctt aa 3042

<210> SEQ ID NO 39
<211> LENGTH: 14291
<212> TYPE: DNA
<213> ORGANISM: Artificial
<220> FEATURE:
<223> OTHER INFORMATION: pRN977

<400> SEQUENCE: 39
gacgaaaggg cctcgtgata cgcctatttt tataggttaa tgtcatgata ataagacgtc 60
aggtggcact tttcggggaa atgtgcgcgg aacccctatt tgtttatttt tctaaataca 120
ttcaaatatg tatccgctca tgagacaata accctgataa atgcttcaat aatattgaaa 180
aaggaagagt atgagtattc aacatttccg tgtcgccctt attccctttt ttgcggcatt 240
ttgccttcct gtttttgctc acccagaaac gctggtgaaa gtaaaagatg ctgaagatca 300
gttgggtgca cgagtgggtt acatcgaact ggatctcaac agcggtaaga tccttgagag 360
ttttcgcccc gaagaacgtt ttccaatgat gagcactttt aaagttctgc tatgtggcgc 420
ggtattatcc cgtattgacg ccgggcaaga gcaactcggt cgccgcatac actattctca 480
gaatgacttg gttgagtact caccagtcac agaaaagcat cttacggatg gcatgacagt 540
aagagaatta tgcagtgctg ccataaccat gagtgataac actgcggcca acttacttct 600
gacaacgatc ggaggaccga aggagctaac cgcttttttt cacaacatgg gggatcatgt 660
aactcgcctt gatcgttggg aaccggagct gaatgaagcc ataccaaacg acgagcgtga 720
caccacgatg cctgtagcaa tggcaacaac gttgcgcaaa ctattaactg gcgaactact 780
tactctagct tcccggcaac aattaataga ctggatggag gcggataaag ttgcaggacc 840
acttctgcgc tcggcccttc cggctggctg gtttattgct gataaatctg gagccggtga 900
gcgtgggtct cgcggtatca ttgcagcact ggggccagat ggtaagccct cccgtatcgt 960
agttatctac acgacgggca gtcaggcaac tatggatgaa cgaaatagac agatcgctga 1020
gataggtgcc tcactgatta agcattggta actgtcagac caagtttact catatatact 1080
ttagattgat ttaaaacttc atttttaatt taaaaggatc taggtgaaga tcctttttga 1140
taatctcatg accaaaatcc cttaacgtga gttttcgttc cactgagcgt cagaccccgt 1200
agaaaagatc aaaggatctt cttgagatcc tttttttctg cgcgtaatct gctgcttgca 1260
aacaaaaaaa ccaccgctac cagcggtggt ttgtttgccg gatcaagagc taccaactct 1320
ttttccgaag gtaactggct tcagcagagc gcagatacca aatactgtcc ttctagtgta 1380
gccgtagtta ggccaccact tcaagaactc tgtagcaccg cctacatacc tcgctctgct 1440
aatcctgtta ccagtggctg ctgccagtgg cgataagtcg tgtcttaccg ggttggactc 1500
aagacgatag ttaccggata aggcgcagcg gtcgggctga acggggggtt cgtgcacaca 1560
gcccagcttg gagcgaacga cctacaccga actgagatac ctacagcgtg agcattgaga 1620
aagcgccacg cttcccgaag ggagaaaggc ggacaggtat ccggtaagcg gcagggtcgg 1680
aacaggagag cgcacgaggg agcttccagg ggggaacgcc tggtatcttt atagtcctgt 1740
cgggtttcgc cacctctgac ttgagcgtcg atttttgtga tgctcgtcag gggggccgag 1800
cctatggaaa aacgccagca acgcggcctt tttacggttc ctggcctttt gctggccttt 1860
tgctcacatg ttctttcctg cgttatcccc tgattctgtg gataaccgta ttaccgcctt 1920

-continued

```
tgagtgagct gataccgctc gccgcagccg aacgaccgag cgcagcgagt cagtgagcga   1980
ggaagcggaa gagcgcccaa tacgcaaacc gcctctcccc gcgcgttggc cgattcatta   2040
atgcagctgg cacgacaggt ttcccgactg gaaagcgggc agtgagcgca acgcaattaa   2100
tgtgagttac ctcactcatt aggcacccca ggctttacac tttatgcttc cggctcctat   2160
gttgtgtgga attgtgagcg gataacaatt tcacacagga aacagctatg accatgatta   2220
cgccaagctc ggaattaacc ctcactaaag ggaacaaaag ctgggtaccg ggcccccct    2280
cgaggtcgag cttaagacgc gtttcttctt cagattccct catggagaaa gtgcggcaga   2340
tgtatatgac agagtcgcca gtttccaaga gactttattc aggcacttcc atgataggca   2400
agagagaaga cccagagatg ttgttgtcct agttacacat ggtatttatt ccagagtatt   2460
cctgatgaaa tggtttagat ggacatacga agagtttgaa tcgtttacca atgttcctaa   2520
cgggagcgta atggtgatgg aactggacga atccatcaat agatacgtcc tgaggaccgt   2580
gctacccaaa tggactgatt gtgagggaga cctaactaca tagtgtttaa agattacgga   2640
tatttaactt acttagaata atgccatttt tttgagttat aataatccta cgttagtgtg   2700
agcgggattt aaactgtgag gaccttaata cattcagaca cttctgcggt atcaccctac   2760
ttattccctt cgagattata tctaggaacc catcaggttg gtggaagatt acccgttcta   2820
agacttttca gcttcctcta ttgatgttac acctggacac cccttttctg gcatccagtt   2880
tttaatcttc agtggcatgt gagattctcc gaaattaatt aaagcaatca cacaattctc   2940
tcggatacca cctcggttga aactgacagg tggtttgtta cgcatgctaa tgcaaaggag   3000
cctatatacc tttggctcgg ctgctgtaac agggaatata aagggcagca taatttagga   3060
gtttagtgaa cttgcaacat ttactatttt cccttcttac gtaaatattt ttctttttaa   3120
ttctaaatca atctttttca atttttgtt tgtattcttt tcttgcttaa atctataact    3180
acaaaaaaca catacataaa tctagaaaat gtccgctaaa tcgtttgaag tcacagatcc   3240
agtcaattca agtctcaaag ggtttgccct tgctaacccc tccattacgc tggtccctga   3300
agaaaaaatt ctcttcagaa agaccgattc cgacaagatc gcattaattt ctggtggtgg   3360
tagtggacat gaacctacac acgccggttt cattggtaag ggtatgttga gtggcgccgt   3420
ggttggcgaa atttttgcat ccccttcaac aaaacagatt ttaaatgcaa tccgtttagt   3480
caatgaaaat gcgtctggcg ttttattgat tgtgaagaac tacacaggtg atgttttgca   3540
ttttggtctg tccgctgaga gagcaagagc cttgggtatt aactgccgcg ttgctgtcat   3600
aggtgatgat gttgcagttg gcagagaaaa gggtggtatg gttggtagaa gagcattggc   3660
aggtaccgtt ttggttcata agattgtagg tgccttcgca gaagaatatt ctagtaagta   3720
tggcttagac ggtacagcta aagtggctaa aattatcaac gacaatttgg tgaccattgg   3780
atcttcttta gaccattgta aagttcctgg caggaaattc gaaagtgaat taaacgaaaa   3840
acaaatggaa ttgggtatgg gtattcataa cgaacctggt gtgaaagttt tagaccctat   3900
tccttctacc gaagacttga tctccaagta tatgctacca aaactattgg atccaaacga   3960
taaggataga gcttttgtaa agtttgatga agatgatgaa gttgtcttgt tagttaacaa   4020
tctcggcggt gtttctaatt ttgttattag ttctatcact tccaaaacta cggatttctt   4080
aaaggaaaat tacaacataa ccccggttca aacaattgct ggcacattga tgacctcctt   4140
caatggtaat gggttcagta tcacattact aaacgccact aaggctacaa aggctttgca   4200
atctgatttt gaggagatca aatcagtact agacttgttg aacgcattta cgaacgcacc   4260
gggctggcca attgcagatt ttgaaaagac ttctgcccca tctgttaacg atgacttgtt   4320
```

-continued

```
acataatgaa gtaacagcaa aggccgtcgg tacctatgac tttgacaagt ttgctgagtg   4380
gatgaagagt ggtgctgaac aagttatcaa gagcgaaccg cacattacgg aactagacaa   4440
tcaagttggt gatggtgatt gtggttacac tttagtggca ggagttaaag gcatcaccga   4500
aaaccttgac aagctgtcga aggactcatt atctcaggcg gttgcccaaa tttcagattt   4560
cattgaaggc tcaatgggag gtacttctgg tggtttatat tctattcttt tgtcgggttt   4620
ttcacacgga ttaattcagg tttgtaaatc aaaggatgaa cccgtcacta aggaaattgt   4680
ggctaagtca ctcggaattg cattggatac tttatacaaa tatacaaagg caaggaaggg   4740
atcatccacc atgattgatg ctttagaacc attcgttaaa gaatttactg catctaagga   4800
tttcaataag gcggtaaaag ctgcagagga aggtgctaaa tccactgcta cattcgaggc   4860
caaatttggc agagcttcgt atgtcggcga ttcatctcaa gtagaagatc ctggtgcagt   4920
aggcctatgt gagtttttga agggggttca aagcgccttg taagtcgaga caaatcgctc   4980
ttaaatatat acctaaagaa cattaaagct atattataag caaagatacg taaattttgc   5040
ttatattatt atacacatat catatttcta tatttttaag atttggttat ataatgtacg   5100
taatgcaaag gaaataaatt ttatacatta ttgaacagcg tccaagtaac tacattatgt   5160
gcactaatag tttagcgtcg tgaagacttt attgtgtcgc gaaaagtaaa aattttaaaa   5220
attagagcac cttgaacttg cgaaaaaggt tctcatcaac tgtttaaaac gtacgcctag   5280
gaagccttcg agcgtcccaa aaccttctca agcaaggttt tcagtataat gttacatgcg   5340
tacacgcgtt tgtacagaaa aaaaagaaaa atttgaaata taaataacgt tcttaatact   5400
aacataacta ttaaaaaaaa taaataggga cctagacttc aggttgtcta actccttcct   5460
tttcggttag agcggatgtg ggaggagggc gtgaatgtaa gcgtgacata actaattaca   5520
tgatatcgac aaaggaaaag gggcgcgcct tattcccatt cttgtaggaa tctttgaccg   5580
tattggtcag caaccaacaa agcagcgtaa acttggtctg ggtagcacc acctggcatg    5640
ttgtggatgg tttcaccttc agcacaagca gcttcagcaa cgattctcat cttagctgga   5700
acgtcttcct tgatgtccaa ttgagccaag gtgattggca aaccaacagc gtgagacaaa   5760
gcagcaacgg tttcgatttc ttcaactgga gcgttttcca aaaccaattg ggtcaaggta   5820
ccgaaagcaa ccttttcacc gtggtagtag tggtgagcgt ctgggatagc ggtcaaaccg   5880
ttgtgaacag cgtgagcagc agccaaacca ccagattcga aaccaacacc agacaagtag   5940
gtgttagctt cgataactct ttccaaagct ggggtaacaa cgtgttgttc agcagccaac   6000
atagcctttt caccttcttc caacaaggtg ttgtaacaca attcagccaa agccaaagca   6060
gcttgggtac acttaccacc agccatggtg gtagcaccag atctagaaca agctctagct   6120
tcgaaccagg tagccaaagc gtcaccgata ccagctgcca acaatctagc tggagcacca   6180
gcaacgatct tggtgtcaac gataaccatg tttgggttgt ttggcaacaa caagtatctg   6240
tcgaattcac cttcgtcggt gtagataaca gacaaagcag aacatggagc gtcggtagaa   6300
gcgatggttg gagcgatagc aactggaaca cccatgaagt gagccaaagc cttagcggtg   6360
tccaaggtct taccaccacc gatacccaag atagcaccac attgagcggt ttcagcgata   6420
cctctcaatc tgtcgatttc gttttgagaa cattcaccac cgaatggagc gatttcaaca   6480
accaaaccag cgtccttgaa agacttttca acggtagatt gagcgaaacc caaaacgaac   6540
ttgtcaccaa caaccaacca tctttcagcc aatggcttca agtattcacc caatctgttg   6600
ataacgtcag caccttggat gtacttacct ggagattgga tgattctgtc cattttctgc   6660
```

-continued agttaattca gtaaattttc gatcttggga agaaaaaagc agtaagcgtg aaaaatctaa 6720
aagctgatgt agtagaagat cctattcttt aacaaagatt gaccttttct ttttcttctt 6780
ggtttgagta gaaaggggaa ggaagaatac aagagagagg aaaaaaagga agataaaaag 6840
agagcgtgat ataaatgaat atatattaaa caagagagat tgggaaggaa aggatcaaac 6900
aaacccaaaa atatttcaaa aaggagagag agaggcgagt ttggtttcaa aacggtttat 6960
ttatttatgc aagaggacgt ggaagaaaaa gaagaaggaa gaaaaaaatt tgaaagaaaa 7020
aaacgcgtgg cgggtaaaga agaaaatgga aaatagaggc cgggtgacag agaaatattg 7080
agggttaatt ggaaaatatg ttagggtgag gcatatgttt ttaagggttt tgaggatccg 7140
ataaggaaga atgtaggtta aatgttgtgc attaattgct gtggcagctt acccgcttcc 7200
ccacacattt actagtctcg agctcttcaa ctcaagacgc acagatatta taacatctgc 7260
ataataggca tttgcaagaa ttactcgtga gtaaggaaag agtgaggaac tatcgcatac 7320
ctgcatttaa agatgccgat ttgggcgcga atcctttatt ttggcttcac cctcatacta 7380
ttatcagggc cagaaaaagg aagtgtttcc ctccttcttg aattgatgtt accctcataa 7440
agcacgtggc ctcttatcga gaaagaaatt accgtcgctc gtgatttgtt tgcaaaaaga 7500
acaaaactga aaaaacccag acacgctcga cttcctgtct tcctattgat tgcagcttcc 7560
aatttcgtca cacaacaagg tcctagcgac ggctcacagg ttttgtaaca agcaatcgaa 7620
ggttctggaa tggcgggaaa gggtttagta ccacatgcta tgatgcccac tgtgatctcc 7680
agagcaaagt tcgttcgatc gtactgttac tctctctctt tcaaacagaa ttgtccgaat 7740
cgtgtgacaa caacagcctg ttctcacaca ctcttttctt ctaaccaagg gggtggttta 7800
gtttagtaga acctcgtgaa acttacattt acatatatat aaacttgcat aaattggtca 7860
atgcaagaaa tacatatttg gtcttttcta attcgtagtt tttcaagttc ttagatgctt 7920
tctttttctc ttttttacag atcatcaagg aagtaattat ctactttttta caacaaatat 7980 atctagaaaa tggctgttac caacgttgct gaattgaacg ctttggttga aagggttaag 8040
aaggctcaaa gagaatacgc ttctttcacc caagaacaag ttgacaagat cttcagagct 8100
gctgctttgg ctgctgctga cgctagaatc ccattggcta agatggctgt tgctgaatct 8160
ggtatgggta tcgttgaaga caaggttatc aagaaccact tcgcttctga atacatctac 8220
aacgcttaca aggacgaaaa gacctgtggt gttttgtcag aagacgacac cttcggtacc 8280
atcaccatcg ctgaaccaat cggtatcatc tgtggtatcg ttccaaccac caacccaacc 8340
tctaccgcta tcttcaagtc tttgatctct ttgaagacca gaaacgctat catcttctct 8400
ccacacccaa gagctaaaga cgctaccaac aaggctgctg acatcgtttt gcaagctgct 8460
atcgctgctg gtgctccaaa ggacttgatc ggttggatcg accaaccatc tgttgaattg 8520
tctaacgctt tgatgcacca cccagacatc aacttgatct tggctaccgg tggtccaggt 8580
atggttaagg ctgcttactc ttctggtaag ccagctatcg gtgttggtgc tggtaacacc 8640
ccagttgtta tcgacgaaac cgctgacatc aagagagctg ttgcttctgt tttgatgtct 8700
aagaccttcg acaacggtgt tatctgtgct tctgaacaat ctgttgttgt tgttgactct 8760
gtttacgacg ctgttagaga aagattcgct acccacggtg gttacttgtt gcaaggtaag 8820
gaattgaagg ctgttcaaga cgttatcttg aagaacggtg ctttgaacgc tgctatcgtt 8880
ggtcaaccag cttacaagat cgctgaatta gctggtttct ctgttccaga aaacaccaag 8940
atcttgatcg gtgaagttac cgttgttgac gaatctgaac cattcgctca cgaaaagttg 9000
tctccaacct tggctatgta cagagctaag gacttcgaag acgctgttga aaaagctgaa 9060

-continued

```
aagttggttg ctatgggtgg tattggtcac acctcttgtt tgtacaccga ccaagacaac   9120
caaccagcta gagtttctta cttcggtcaa aagatgaaga ccgctagaat cttgatcaac   9180
accccagctt ctcaaggtgg tatcggtgac ttgtacaact tcaagttggc tccatctttg   9240
accttgggtt gtggttcttg ggtggtaac tctatctctg aaaacgttgg tccaaagcac   9300
ttgatcaaca agaagaccgt tgctaagaga gctgaaaaca tgttgtggca caagttgcca   9360
aaatctatct acttcagaag aggttctttg ccaatcgctt tggacgaagt tatcaccgac   9420
ggtcacaaga gagctttgat cgttaccgac agattcttgt tcaacaacgg ttacgctgac   9480
caaatcacct ctgttttgaa ggctgctggt gttgaaaccg aagttttctt cgaagttgaa   9540
gctgacccaa ccttgtctat cgttagaaag ggtgctgaat tggctaactc tttcaagcca   9600
gacgttatca tcgctttggg tggtggttct ccaatggacg ctgctaagat catgtgggtt   9660
atgtacgaac acccagaaac ccacttcgaa gaattggctt tgagattcat ggacatcaga   9720
aagagaatct acaagttccc aaagatgggt gttaaggcta agatgatcgc tgttaccacc   9780
acctctggta ccggttctga agttacccca ttcgctgttg ttaccgacga cgctaccggt   9840
caaaagtacc cattggctga ctacgctttg accccagaca tggctatcgt tgacgctaac   9900
ttggttatgg acatgccaaa gtctttgtgt gctttcggtg gtttggacgc tgttacccac   9960
gctatggaag cttacgtttc tgttttggct tctgaattct ctgacggtca agctttgcaa  10020
gctttgaagt tgttgaagga atacttgcca gcttcttacc acgaaggttc taagaaccca  10080
gttgctagag aaagagttca ctctgctgct accatcgctg gtatcgcttt cgctaacgct  10140
ttcttgggtg tttgtcactc tatggctcac aagttgggtt ctcaattcca catcccacac  10200
ggtttggcta acgctttgtt gatctgtaac gttatcagat acaacgctaa cgacaaccca  10260
accaagcaaa ccgctttctc tcaatacgac agaccacaag ctagaagaag atacgctgaa  10320
atcgctgacc acttgggttt gtctgctcca ggtgacagaa ccgctgcaaa gatcgaaaag  10380
ttgttggctt ggttggaaac cttgaaggct gaattgggta tcccaaagtc tatcagagaa  10440
gctggtgttc aagaagctga cttcttggct aacgttgaca agttgtctga agacgctttc  10500
gacgaccaat gtaccggtgc taacccaaga tacccattga tctctgaatt gaagcaaatc  10560
ttgttggaca cctactacgg tagagactac gttgaaggtg aaaccgctgc taagaaggaa  10620
gctgctccag ctaaggctga aaagaaggct aagaagtctg cttagcttaa gcgcgcgaat  10680
ttcttatgat ttatgatttt tattattaaa taagttataa aaaaaataag tgtatacaaa  10740
ttttaaagtg actcttaggt tttaaaacga aaattcttat tcttgagtaa ctctttcctg  10800
taggtcaggt tgctttctca ggtatagcat gaggtcgctc ttattgacca cacctctacc  10860
ggcatgccga gcaaatgcct gcaaatcgct ccccatttca cccaattgta gatatgctaa  10920
ctccagcaat gagttgatga atctcggtgt gtattttatg tcctcagagg acaacacctg  10980
ttgtaatcgt tcttccacac gtacgaagct taaaagggcg aattctgcag atatccatca  11040
cactggcggc cgcatgctag ctccggatta tcgatgataa gctgtcaaag atgagaatta  11100
attccacgga ctatagacta tactagatac tccgtctact gtacgataca cttccgctca  11160
ggtccttgtc ctttaacgag gccttaccac tcttttgtta ctctattgat ccagctcagc  11220
aaaggcagtg tgatctaaga ttctatcttc gcgatgtagt aaaactagct agaccgagaa  11280
agagactaga aatgcaaaag gcacttctac aatggctgcc atcattatta tccgatgtga  11340
cgctgcagct tctcaatgat attcgaatac gctttgagga gatacagcct aatatccgac  11400
```

-continued aaactgtttt acagatttac gatcgtactt gttacccatc attgaatttt gaacatccga 11460
acctgggagt tttccctgaa acagatagta tatttgaacc tgtataataa tatatagtct 11520
agcgctttac ggaagacaat gtatgtattt cggttcctgg agaaactatt gcatctattg 11580
cataggtaat cttgcacgtc gcatccccgg ttcattttct gcgtttccat cttgcacttc 11640
aatagcatat ctttgttaac gaagcatctg tgcttcattt tgtagaacaa aaatgcaacg 11700
cgagagcgct aatttttcaa acaaagaatc tgagctgcat tttacagaa cagaaatgca 11760
acgcgaaagc gctattttac caacgaagaa tctgtgcttc atttttgtaa aacaaaaatg 11820
caacgcgacg agagcgctaa tttttcaaac aaagaatctg agctgcattt ttacagaaca 11880
gaaatgcaac gcgagagcgc tattttacca acaaagaatc tatacttctt ttttgttcta 11940
caaaaatgca tcccgagagc gctatttttc taacaaagca tcttagatta cttttttct 12000
cctttgtgcg ctctataatg cagtctcttg ataacttttt gcactgtagg tccgttaagg 12060
ttagaagaag gctactttgg tgtctatttt ctcttccata aaaaaagcct gactccactt 12120
cccgcgttta ctgattacta gcgaagctgc gggtgcattt tttcaagata aaggcatccc 12180
cgattatatt ctataccgat gtggattgcg catactttgt gaacagaaag tgatagcgtt 12240
gatgattctt cattggtcag aaaattatga acggtttctt ctattttgtc tctatatact 12300
acgtatagga aatgtttaca ttttcgtatt gttttcgatt cactctatga atagttctta 12360
ctacaatttt tttgtctaaa gagtaatact agagataaac ataaaaaatg tagaggtcga 12420
gtttagatgc aagttcaagg agcgaaaggt ggatgggtag gttatatagg gatatagcac 12480
agagatatat agcaaagaga tacttttgag caatgtttgt ggaagcggta ttcgcaatgc 12540
cggctttccc cgtcaagctc taaatcgggg gctcccttta gggttccgat ttagtgcttt 12600
acggcacctc gaccccaaaa aacttgatta gggtgatggt tcacgtagtg ggccatcgcc 12660
ctgatagacg gtttttcgcc ctttgacgtt ggagtccacg ttctttaata gtggactctt 12720
gttccaaact ggaacaacac tcaaccctat ctcggtctat tcttttgatt tataagggat 12780
tttgccgatt tcggcctatt ggttaaaaaa tgagctgatt taacaaaaat ttaacgcgaa 12840
ttttaacaaa atattaacgt ttacaatttc ctgatgcggt attttctcct tacgcatctg 12900
tgcggtattt cacaccgcat atgatccgtc gagttcaaga gaaaaaaaaa gaaaaagcaa 12960
aaagaaaaaa ggaaagcgcg cctcgttcag aatgacacgt atagaatgat gcattacctt 13020
gtcatcttca gtatcatact gttcgtatac atacttactg acattcatag gtatacatat 13080
atacacatgt atatatatcg tatgctgcag ctttaaataa tcggtgtcac tacataagaa 13140
cacctttggt ggagggaaca tcgttggtac cattgggcga ggtggcttct cttatggcaa 13200
ccgcaagagc cttgaacgca ctctcactac ggtgatgatc attcttgcct cgcagacaat 13260
caacgtggag ggtaattctg ctagcctctg caaagctttc aagaaaatgc gggatcatct 13320
cgcaagagag atctcctact ttctcccttt gcaaaccaag ttcgacaact gcgtacggcc 13380
tgttcgaaag atctaccacc gctctggaaa gtgcctcatc caaaggcgca aatcctgatc 13440
caaacctttt tactccacgc gccagtaggg cctctttaaa agcttgaccg agagcaatcc 13500
cgcagtcttc agtggtgtga tggtcgtcta tgtgtaagtc accaatgcac tcaacgatta 13560
gcgaccagcc ggaatgcttg gccagagcat gtatcatatg gtccagaaac cctatacctg 13620
tgtggacgtt aatcacttgc gattgtgtgg cctgttctgc tactgcttct gcctcttttt 13680
ctgggaagat cgagtgctct atcgctaggg gaccaccctt taaagagatc gcaatctgaa 13740
tcttggtttc atttgtaata cgctttacta gggctttctg ctctgtcatc tttgccttcg 13800

```
tttatcttgc ctgctcattt tttagtatat tcttcgaaga aatcacatta ctttatataa  13860

tgtataattc attatgtgat aatgccaatc gctaagaaaa aaaaagagtc atccgctagg  13920

tggaaaaaaa aaaatgaaaa tcattaccga ggcataaaaa aatatagagt gtactagagg  13980

aggccaagag taatagaaaa agaaaattgc gggaaaggac tgtgttatga cttccctgac  14040

taatgccgtg ttcaaacgat acctggcagt gactcctagc gctcaccaag ctcttaaaac  14100

ggaattatgg tgcactctca gtacaatctg ctctgatgcc gcatagttaa gccagccccg  14160

acacccgcca acacccgctg acgcgccctg acgggcttgt ctgctcccgg catccgctta  14220

cagacaagct gtgaccgtct ccgggagctg catgtgtcag aggttttcac cgtcatcacc  14280

gaaacgcgcg a                                                       14291
```

```
<210> SEQ ID NO 40
<211> LENGTH: 4891
<212> TYPE: DNA
<213> ORGANISM: Artificial
<220> FEATURE:
<223> OTHER INFORMATION: pRN593

<400> SEQUENCE: 40
```

```
gttttaaatc aatctaaagt atatatgagt aaacttggtc tgacagttac caatgcttaa     60

tcagtgaggc acctatctca gcgatctgtc tatttcgttc atccatagtt gcctgactcc    120

ccgtcgtgta gataactacg atacgggagg gcttaccatc tggccccagt gctgcaatga    180

taccgcgaga cccacgctca ccggctccag atttatcagc aataaaccag ccagccggaa    240

gggccgagcg cagaagtggt cctgcaactt tatccgcctc catccagtct attaattgtt    300

gccgggaagc tagagtaagt agttcgccag ttaatagttt gcgcaacgtt gttgccattg    360

ctacaggcat cgtggtgtca cgctcgtcgt ttggtatggc ttcattcagc tccggttccc    420

aacgatcaag gcgagttaca tgatccccca tgttgtgcaa aaaagcggtt agctccttcg    480

gtcctccgat cgttgtcaga agtaagttgg ccgcagtgtt atcactcatg gttatggcag    540

cactgcataa ttctcttact gtcatgccat ccgtaagatg cttttctgtg actggtgagt    600

actcaaccaa gtcattctga gaatagtgta tgcggcgacc gagttgctct tgcccggcgt    660

caatacggga taataccgcg ccacatagca gaactttaaa agtgctcatc attggaaaac    720

gttcttcggg gcgaaaactc tcaaggatct taccgctgtt gagatccagt tcgatgtaac    780

ccactcgtgc acccaactga tcttcagcat cttttacttt caccagcgtt tctgggtgag    840

caaaaacagg aaggcaaaat gccgcaaaaa agggaataag ggcgacacgg aaatgttgaa    900

tactcatact cttccttttt caattcagaa gaactcgtca agaaggcgat agaaggcgat    960

gcgctgcgaa tcgggagcgg cgataccgta aagcacgagg aagcggtcag cccattcgcc   1020

gccaagctct tcagcaatat cacgggtagc caacgctatg tcctgatagc ggtccgccac   1080

acccagccgg ccacagtcga tgaatccaga aaagcggcca ttttccacca tgatattcgg   1140

caagcaggca tcgccatggt accgagtggt gttgtaacca ccctcaaaaa atgcggaaga   1200

ggtgtacagc taatattata atggaaaatc cttttgctct ataggatttt tttttaaaa   1260

tttaaatata catatttatt tatatttatt tggttactaa attttgtatt aatttaataa   1320

taataagtaa tttctaacgt gataaagtag ttatgagaaa tgacataatg ctaatttatg   1380

aatatgatat agaagagcct cgaaaaaagt gggggaaagt atgatatgtt atctttctcc   1440

aataaatcta atcttcatgt agatctaatt cttcaatcat gtccggcagg ttcttcattg   1500
```

-continued

```
ggtagttgtt gtaaacgatt tggtatacgg cttcaaataa tgggaagtct tcgacagagc   1560
cacatgtttc caaccattcg tgaacttctt tgcaggtaat taaaccttga gcggattggc   1620
cattcaacaa ctcgtacacc taggatccgt cgacactgga tggcggcgtt agtatcgaat   1680
cgacagcagt atagcgacca gcattcacat acgattgacg catgatatta ctttctgcgc   1740
acttaacttc gcatctgggc agatgatgtc gaggcgaaaa aaaatataaa tcacgctaac   1800
atttgattaa aatagaacaa ctacaatata aaaaaactat acaaatgaca agttcttgaa   1860
aacaagaatc tttttattgt cagtactgat tattcctttg ccctcggacg agtgctgggg   1920
cgtcggtttc cactatcggc gagtacttct acacagccat cggtccagac ggccgcgctt   1980
ctgcgggcga tttgtgtacg cccgacagtc ccggctccgg atcggacgat tgcgtcgcat   2040
cgaccctgcg cccaagctgc atcatcgaaa ttgccgtcaa ccaagctctg atagagttgg   2100
tcaagaccaa tgcggagcat atacgcccgg agccgcggcg atcctgcaag ctccggatgc   2160
ctccgctcga agtagcgcgt ctgctgctcc atacaagcca accacggcct ccagaagaag   2220
atgttggcga cctcgtattg ggaatccccg aacatcgcct cgctccagtc aatgaccgct   2280
gttatgcggc cattgtccgt caggacattg ttggagccga aatccgcgtg cacgaggtgc   2340
cggacttcgg ggcagtcctc ggcccaaagc atcagctcat cgagagcctg cgcgacggac   2400
gcactgacgg tgtcgtccat cacagtttgc cagtgataca catggggatc agcaatcgcg   2460
catatgaaat cacgccatgt agtgtattga ccgattcctt gcggtccgaa tgggccgaac   2520
ccgctcgtct ggctaagatc ggccgcagcg atcgcatcca tggcctccgc gaccggctgc   2580
agaacagcgg gcagttcggt ttcaggcagg tcttgcaacg tgacaccctg tgcacggcgg   2640
gagatgcaat aggtcaggct ctcgctgaat tccccaatgt caagcacttc cggaatcggg   2700
agcgcggccg atgcaaagtg ccgataaaca taacgatctt tgtagaaacc atcggcgcag   2760
ctatttaccc gcaggacata tccacgccct cctacatcga agctgaaagc acgagattct   2820
tcgccctccg agagctgcat caggtcggag acgctgtcga acttttcgat cagaaacttc   2880
tcgacagacg tcgcggtgag ttcaggcttt ttacccatgg ttgtttatgt tcggatgtga   2940
tgtgagaact gtatcctagc aagattttaa aaggaagtat atgaaagaag aacctcagtg   3000
gcaaatccta accttttata tttctctaca ggggcgcggc gtggggacaa ttcacgcgtc   3060
tgtgagggga gcgtttccct gctcgcaggt ctgcagcgag gagccgtaat ttttgcttcg   3120
cgccgtgcgg ccatcaaaat gtatggatgc aaatgattat acatggggat gtatgggcta   3180
aatgtacggg cgacagtcac atcatgcccc tgagctgcgc acgtcaagac tgtcaaggag   3240
ggtattctgg gcctccatgt cgctggccgg gtgacccggc ggggacgagg ccttaagttc   3300
gaacgtacga gctccggatt aagggcgaat tccagcacac tggcggccgt tactagacca   3360
gcattcaagt ggccggaagt taagtttaat ctatcagcag cagcagacat ctttatatta   3420
tcaatatttg tgtttgtgga gggggggggt gtacaatata caattgtttc ttgatgtctt   3480
atgtaggaga gtaagataaa agaaaattaa agggagaaag aatttaaggt aacgtaacag   3540
tttcactcat ggtagtatat atataactac gaaactgcca ataccaagcc agtctacgtg   3600
cgaattaggt tggatagatt tgatgaaccc attctgatac ttgttgtgcg gaaaaaggga   3660
caaaataggg aaaactggaa aaagaaaagg aaggggagag aagcaaggcg ggtaccaagc   3720
ttgatgcata gcttgagtat tctatagtgt cacctaaata gcttggcgta atcatggtca   3780
tagctgtttc ctgtgtgaaa ttgttatccg ctcacaattc cacacaacat acgagccgga   3840
agcataaagt gtaaagcctg gggtgcctaa tgagtgagct aactcacatt aattgcgttg   3900
```

cgctcactgc ccgctttcca gtcgggaaac ctgtcgtgcc agctgcatta atgaatcggc 3960
caacgcgcgg ggagaggcgg tttgcgtatt gggcgctctt ccgcttcctc gctcactgac 4020
tcgctgcgct cggtcgttcg gctgcggcga gcggtatcag ctcactcaaa ggcggtaata 4080
cggttatcca cagaatcagg ggataacgca ggaaagaaca tgtgagcaaa aggccagcaa 4140
aaggccagga accgtaaaaa ggccgcgttg ctggcgtttt tccataggct ccgcccccct 4200
gacgagcatc acaaaaatcg acgctcaagt cagaggtggc gaaacccgac aggactataa 4260
agataccagg cgtttccccc tggaagctcc ctcgtgcgct ctcctgttcc gaccctgccg 4320
cttaccggat acctgtccgc ctttctccct tcgggaagcg tggcgctttc tcatagctca 4380
cgctgtaggt atctcagttc ggtgtaggtc gttcgctcca agctgggctg tgtgcacgaa 4440
ccccccgttc agcccgaccg ctgcgcctta tccggtaact atcgtcttga gtccaacccg 4500
gtaagacacg acttatcgcc actggcagca gccactggta acaggattag cagagcgagg 4560
tatgtaggcg gtgctacaga gttcttgaag tggtggccta actacggcta cactagaaga 4620
acagtatttg gtatctgcgc tctgctgaag ccagttacct tcggaaaaag agttggtagc 4680
tcttgatccg gcaaacaaac caccgctggt agcggtggtt tttttgtttg caagcagcag 4740
attacgcgca gaaaaaaagg atctcaagaa gatcctttga tcttttctac ggggtctgac 4800
gctcagtgga acgaaaactc acgttaaggg attttggtca tgagattatc aaaaaggatc 4860
ttcacctaga tccttttaaa ttaaaaatga a 4891

<210> SEQ ID NO 41
<211> LENGTH: 30
<212> TYPE: DNA
<213> ORGANISM: Artificial
<220> FEATURE:
<223> OTHER INFORMATION: Primer gpd1uf

<400> SEQUENCE: 41
aagcttggta cccgccttgc ttctctcccc 30

<210> SEQ ID NO 42
<211> LENGTH: 26
<212> TYPE: DNA
<213> ORGANISM: Artificial
<220> FEATURE:
<223> OTHER INFORMATION: Primer gpd1ur

<400> SEQUENCE: 42
tctagaccag cattcaagtg gccgga 26

<210> SEQ ID NO 43
<211> LENGTH: 29
<212> TYPE: DNA
<213> ORGANISM: Artificial
<220> FEATURE:
<223> OTHER INFORMATION: Primer gpd1df

<400> SEQUENCE: 43
cgtacgagtt gttgaatggc caatccgct 29

<210> SEQ ID NO 44
<211> LENGTH: 31
<212> TYPE: DNA
<213> ORGANISM: Artificial
<220> FEATURE:
<223> OTHER INFORMATION: Primer gpd1dr

<400> SEQUENCE: 44
ccatggtacc gagtggtgtt gtaaccaccc t 31

<210> SEQ ID NO 45
<211> LENGTH: 20
<212> TYPE: DNA
<213> ORGANISM: Artificial
<220> FEATURE:
<223> OTHER INFORMATION: Primer gpd1cf

<400> SEQUENCE: 45
accaatacgt aaacggggcg 20

<210> SEQ ID NO 46
<211> LENGTH: 23
<212> TYPE: DNA
<213> ORGANISM: Artificial
<220> FEATURE:
<223> OTHER INFORMATION: Primer gpd1cr

<400> SEQUENCE: 46
aatacaccca tacatacgga cgc 23

<210> SEQ ID NO 47
<211> LENGTH: 28
<212> TYPE: DNA
<213> ORGANISM: Artificial
<220> FEATURE:
<223> OTHER INFORMATION: Primer acs1f

<400> SEQUENCE: 47
ttaagcttaa aatgtcgccc tctgccgt 28

<210> SEQ ID NO 48
<211> LENGTH: 50
<212> TYPE: DNA
<213> ORGANISM: Artificial
<220> FEATURE:
<223> OTHER INFORMATION: Primer acs1r

<400> SEQUENCE: 48
aagcgcgcta caacttgacc gaatcaatta gatgtctaac aatgccaggg 50

<210> SEQ ID NO 49
<211> LENGTH: 49
<212> TYPE: DNA
<213> ORGANISM: Artificial
<220> FEATURE:
<223> OTHER INFORMATION: Primer acs2f

<400> SEQUENCE: 49
aactgcagaa aatgacaatc aaggaacata aagtagttta tgaagctca 49

<210> SEQ ID NO 50
<211> LENGTH: 49
<212> TYPE: DNA
<213> ORGANISM: Artificial
<220> FEATURE:
<223> OTHER INFORMATION: Primer acs2r

<400> SEQUENCE: 50
acgtcgacta tttctttttt tgagagaaaa attggttctc tacagcaga 49

<210> SEQ ID NO 51
<211> LENGTH: 13018

-continued

<212> TYPE: DNA
<213> ORGANISM: Artificial
<220> FEATURE:
<223> OTHER INFORMATION: pRN753

<400> SEQUENCE: 51
gacgaaaggg cctcgtgata cgcctatttt tataggttaa tgtcatgata ataatggttt 60
cttagacgtc aggtggcact tttcggggaa atgtgcgcgg aacccctatt tgtttatttt 120
tctaaataca ttcaaatatg tatccgctca tgagacaata accctgataa atgcttcaat 180
aatattgaaa aaggaagagt atgagtattc aacatttccg tgtcgccctt attccctttt 240
ttgcggcatt ttgccttcct gtttttgctc acccagaaac gctggtgaaa gtaaaagatg 300
ctgaagatca gttgggtgca cgagtgggtt acatcgaact ggatctcaac agcggtaaga 360
tccttgagag ttttcgcccc gaagaacgtt ttccaatgat gagcactttt aaagttctgc 420
tatgtggcgc ggtattatcc cgtattgacg ccgggcaaga gcaactcggt cgccgcatac 480
actattctca gaatgacttg gttgagtact caccagtcac agaaaagcat cttacggatg 540
gcatgacagt aagagaatta tgcagtgctg ccataaccat gagtgataac actgcggcca 600
acttacttct gacaacgatc ggaggaccga aggagctaac cgcttttttt cacaacatgg 660
gggatcatgt aactcgcctt gatcgttggg aaccggagct gaatgaagcc ataccaaacg 720
acgagcgtga caccacgatg cctgtagcaa tggcaacaac gttgcgcaaa ctattaactg 780
gcgaactact tactctagct tcccggcaac aattaataga ctggatggag gcggataaag 840
ttgcaggacc acttctgcgc tcggcccttc cggctggctg gtttattgct gataaatctg 900
gagccggtga gcgtgggtct cgcggtatca ttgcagcact ggggccagat ggtaagccct 960
cccgtatcgt agttatctac acgacgggca gtcaggcaac tatggatgaa cgaaatagac 1020
agatcgctga gataggtgcc tcactgatta agcattggta actgtcagac caagtttact 1080
catatatact ttagattgat ttaaaacttc atttttaatt taaaaggatc taggtgaaga 1140
tcctttttga taatctcatg accaaaatcc cttaacgtga gttttcgttc cactgagcgt 1200
cagaccccgt agaaaagatc aaaggatctt cttgagatcc tttttttctg cgcgtaatct 1260
gctgcttgca aacaaaaaaa ccaccgctac cagcggtggt ttgtttgccg gatcaagagc 1320
taccaactct ttttccgaag gtaactggct tcagcagagc gcagatacca aatactgtcc 1380
ttctagtgta gccgtagtta ggccaccact tcaagaactc tgtagcaccg cctacatacc 1440
tcgctctgct aatcctgtta ccagtggctg ctgccagtgg cgataagtcg tgtcttaccg 1500
ggttggactc aagacgatag ttaccggata aggcgcagcg gtcgggctga acggggggtt 1560
cgtgcacaca gcccagcttg gagcgaacga cctacaccga actgagatac ctacagcgtg 1620
agcattgaga aagcgccacg cttcccgaag ggagaaaggc ggacaggtat ccggtaagcg 1680
gcagggtcgg aacaggagag cgcacgaggg agcttccagg ggggaacgcc tggtatcttt 1740
atagtcctgt cgggtttcgc cacctctgac ttgagcgtcg atttttgtga tgctcgtcag 1800
gggggccgag cctatggaaa aacgccagca acgcggcctt tttacggttc ctggcctttt 1860
gctggccttt tgctcacatg ttctttcctg cgttatcccc tgattctgtg gataaccgta 1920
ttaccgcctt tgagtgagct gataccgctc gccgcagccg aacgaccgag cgcagcgagt 1980
cagtgagcga ggaagcggaa gagcgcccaa tacgcaaacc gcctctcccc gcgcgttggc 2040
cgattcatta atgcagctgg cacgacaggt ttcccgactg gaaagcgggc agtgagcgca 2100
acgcaattaa tgtgagttac ctcactcatt aggcacccca ggctttacac tttatgcttc 2160

-continued

```
cggctcctat gttgtgtgga attgtgagcg gataacaatt tcacacagga aacagctatg   2220
accatgatta cgccaagctc ggaattaacc ctcactaaag ggaacaaaag ctgggtaccg   2280
ggcccccccct cgaccggtcc cacacaccat agcttcaaaa tgtttctact ccttttttac   2340
tcttccagat tttctcggac tccgcgcatc gccgtaccac ttcaaaacac ccaagcacag   2400
catactaaat ttcccctctt tcttcctcta gggtgtcgtt aattacccgt actaaaggtt   2460
tggaaaagaa aaaagagacc gcctcgtttc tttttcttcg tcgaaaaagg caataaaaat   2520
ttttatcacg tttctttttc ttgaaaattt tttttttga tttttttctc tttcgatgac   2580
ctcccattga tatttaagtt aataaacggt cttcaatttc tcaagtttca gtttcatttt   2640
tcttgttcta ttacaacttt ttttacttct tgctcattag aaagaaagca tagcaatcta   2700
atctaagctg cagaagctta aaatgtcgcc ctctgccgta caatcatcaa aactagaaga   2760
acagtcaagt gaaattgaca agttgaaagc aaaaatgtcc cagtctgccg ccactgcgca   2820
gcagaagaag gaacatgagt atgaacattt gacttcggtc aagatcgtgc cacaacggcc   2880
catctcagat agactgcagc ccgcaattgc tacccactat tctccacact tggacgggtt   2940
gcaggactat cagcgcttgc acaaggagtc tattgaagac cctgctaagt tcttcggttc   3000
taaagctacc caatttttaa actggtctaa gccattcgat aaggtgttca tcccagaccc   3060
taaaacgggc aggccctcct tccagaacaa tgcatggttc ctcaacggcc aattaaacgc   3120
ctgttacaac tgtgttgaca gacatgcctt gaagactcct aacaagaaag ccattatttt   3180
cgaaggtgac gagcctggcc aaggctattc cattacctac aaggaactac ttgaagaagt   3240
ttgtcaagtg gcacaagtgc tgacttactc tatgggcgtt cgcaagggcg atactgttgc   3300
cgtgtacatg cctatggtcc cagaagcaat cataaccttg ttggccattt cccgtatcgg   3360
tgccattcac tccgtagtct ttgccgggtt ttcttccaac tccttgagag atcgtatcaa   3420
cgatggggac tctaaagttg tcatcactac agatgaatcc aacagaggtg gtaaagtcat   3480
tgagactaaa agaattgttg atgacgcgct aagagagacc ccaggcgtga gacacgtctt   3540
ggtttataga aagaccaaca atccatctgt tgctttccat gcccccagag atttggattg   3600
ggcaacagaa aagaagaaat acaagaccta ctatccatgc acacccgttg attctgagga   3660
tccattattc ttgttgtata cgtctggttc tactggtgcc cccaagggtg ttcaacattc   3720
taccgcaggt tacttgctgg gagctttgtt gaccatgcgc tacacttttg acactcacca   3780
agaagacgtt ttcttcacag ctggagacat tggctggatt acaggccaca cttatgtggt   3840
ttatggtccc ttactatatg gttgtgccac tttggtcttt gaagggactc ctgcgtaccc   3900
aaattactcc cgttattggg atattattga tgaacacaaa gtcacccaat tttatgttgc   3960
gccaactgct ttgcgtttgt tgaaaagagc tggtgattcc tacatcgaaa atcattcctt   4020
aaaatctttg cgttgcttgg gttcggtcgg tgagccaatt gctgctgaag tttgggagtg   4080
gtactctgaa aaaataggta aaaatgaaat ccccattgta gacacctact ggcaaacaga   4140
atctggttcg catctggtca ccccgctggc tggtggtgtt acaccaatga aaccgggttc   4200
tgcctcattc cccttcttcg gtattgatgc agttgttctt gaccctaaca ctggtgaaga   4260
acttaacacc agccacgcag agggtgtcct tgccgtcaaa gctgcatggc catcatttgc   4320
aagaactatt tggaaaaatc atgataggta tctagacact tatttgaacc cttaccctgg   4380
ctactatttc actggtgatg gtgctgcaaa ggataaggat ggttatatct ggattttggg   4440
tcgtgtagac gatgtggtga acgtctctgg tcaccgtctg tctaccgctg aaattgaggc   4500
tgctattatc gaagatccaa ttgtggccga gtgtgctgtt gtcggattca acgatgactt   4560
```

-continued

```
gactggtcaa gcagttgctg catttgtggt gttgaaaaac aaatctagtt ggtccaccgc   4620
aacagatgat gaattacaag atatcaagaa gcatttggtc tttactgtta gaaaagacat   4680
cgggccattt gccgcaccaa aattgatcat tttagtggat gacttgccca agacaagatc   4740
cggcaaaatt atgagacgta ttttaagaaa aatcctagca ggagaaagtg accaactagg   4800
cgacgtttct acattgtcaa accctggcat tgttagacat ctaattgatt cggtcaagtt   4860
gtaacttaag cgcgcgaatt tcttatgatt tatgattttt attattaaat aagttataaa   4920
aaaaataagt gtatacaaat tttaaagtga ctcttaggtt ttaaaacgaa aattcttatt   4980
cttgagtaac tctttcctgt aggtcaggtt gctttctcag gtatagcatg aggtcgctct   5040
tattgaccac acctctaccg gcatgccgag caaatgcctg caaatcgctc cccatttcac   5100
ccaattgtag atatgctaac tccagcaatg agttgatgaa tctcggtgtg tattttatgt   5160
cctcagagga caacacctgt tgtaatcgtt cttccacacg tacgttttaa acagttgatg   5220
agaacctttt tcgcaagttc aaggtgctct aatttttaaa atttttactt ttcgcgacac   5280
aataaagtct tcacgacgct aaactattag tgcacataat gtagttactt ggacgctgtt   5340
caataatgta taaaatttat ttcctttgca ttacgtacat tatataacca aatcttaaaa   5400
atatagaaat atgatatgtg tataataata taagcaaaat ttacgtatct ttgcttataa   5460
tatagcttta atgttcttta ggtatatatt taagagcgat ttgtctcgac tatttctttt   5520
tttgagagaa aaattggttc tctacagcag aaatgatggc aggtacaact tctgggttgg   5580
ccaaagtagt taggtcacct agctgttcgg cttcgttaga agcaaccttt cttagaactc   5640
ttctcataat ctttcctgac cttgttcttg gtagatctct aactagaata atggtttttg   5700
gtgaggcgaa aggaccaatc tcacccctaa cttgtaagat caattctcta cgtaaattat   5760
ctggtgtgat gtgttctgca tcaccttcag tagcgttgtt ttgtagataa ccatctttta   5820
gggaaacata tgcaacgacg gtttgaccgg tcaattcatc tggaataccg acaacagcag   5880
cttccgagac gttttcgtga tttgagatag atgcttcaat ttctgatgtg gataatctat   5940
gaccggaaac atttacaacg tcgtcaactc taccctgat ccagtagtaa ccatcatgat   6000
ctctaccagc accatcacct gtgaaatagt gaccaggata aggtttcaag taagtatcca   6060
tgtaacggtc gtggtggttc caaacagatc tagccattga tggccatggt gatttaacgg   6120
caaggacacc ttcgacatca ttaccttcta attccacacc tgtaacaggg tcaatgatac   6180
aagcgttaat accaaagaat ggcacggtag cagaaccagg ttttgttggg acagcacctg   6240
ccaaaggagc aattaaatga gaaccagact ctgtttgcca catagtgtca caaatgacac   6300
agtttttgtt acccactttt tcatgatacc attcccataa gtctggagag attggttcac   6360
cgacggaacc caagacacgt aatgaggaag tgtcatattt ggcaatttcg gcttcaccta   6420
cacgtttgat taatcttaaa gcagttggag ccacatagaa atgggtagcc ttgtgacgtt   6480
ggataattct ccaatatcta ccataatctg ggtaggcagg agtggattcg aaaattattg   6540
aggcggtacc caaggttaat ggaccatata gagcataggt gtgacccgtg atccagccga   6600
cgtcaccggc agtgaagaga acatcttctg ggtgaatatc aaaaacgtat ctagttgtta   6660
aagcggcacc taataaataa ccacctgtag tgtgaacgac accctttgga gaaccagtgg   6720
aaccggaagt gtataataaa aatagaggat cttcagcgtc acatgaaaca ggaggtaggt   6780
aagttctctg cttagcggcc tcctcatgcc accagtaatc tctaccggcc ttcattggaa   6840
taccttcagt accagttctt tggaaaacca agatacggga aaccaaatcg actccgttca   6900
```

-continued

```
aaccttcgtc aacaattttt ttagtgttga tggtcttacc acctctttta ccttcatcac   6960
aagtgatgac cactttagaa ttagcgtcaa cgacacgatc tttcaacgaa ccagcggaga   7020
acccagcaaa gacaacagag tgaatagcac caatacgagc cacagccaac atagcaatga   7080
ccgcttctgg aatcattggc aaatagatag ccactgtgtc acctttctta acgccccagc   7140
tttttaagac accagcgatt tgggaaactt ttctgagtaa ttcaccaaat gtgatgattt   7200
tgttgtcgga ttcgtcatca gcttcataga tcaaagctgg cttgtcggga ttagcaaagg   7260
catgtctgtc aacacaattg tatgatgcat tcaatttacc gttcaaaaac catgcaacat   7320
caccattgtt caatgaacca gattgaactt tggtgtatgg agcatcccaa tgcaagtatt   7380
ccttagccat cttatcaaag aatttttctg gctcattgat agattgttga tacatttctt   7440
gataatgttg catatcagta acgtaaccct tgccgggttg gctgttgtaa aaatgttgag   7500
gagccttaag agcctttacg ttgtgagctt cataaactac tttatgttcc ttgattgtca   7560
ttttctgcag tctagatata tttgttgtaa aaagtagata attacttcct tgatgatctg   7620
taaaaaagag aaaaagaaag catctaagaa cttgaaaaac tacgaattag aaaagaccaa   7680
atatgtattt cttgcattga ccaatttatg caagtttata tatatgtaaa tgtaagtttc   7740
acgaggttct actaaactaa accacccccct tggttagaag aaaagagtgt gtgagaacag  7800
gctgttgttg tcacacgatt cggacaattc tgtttgaaag agagagagta acagtacgat   7860
cgaacgaact ttgctctgga gatcacagtg ggcatcatag catgtggtac taaacccttt   7920
cccgccattc cagaaccttc gattgcttgt tacaaaacct gtgagccgtc gctaggacct   7980
tgttgtgtga cgaaattgga agctgcaatc aataggaaga caggaagtcg agcgtgtctg   8040
ggtttttcca gttttgttct ttttgcaaac aaatcacgag cgacggtaat ttctttctcg   8100
ataagaggcc acgtgcttta tgagggtaac atcaattcaa gaaggaggga aacacttcct   8160
ttttctggcc ctgataatag tatgagggtg aagccaaaat aaaggattcg cgcccaaatc   8220
ggcatcttta aatgcaggta tgcgatagtt cctcactctt tccttactca cgagtaattc   8280
ttgcaaatgc ctattatgca gatgttataa tatctgtgcg tcttgagttg aagagctcga   8340
gactagatgc atgctcgagc ggccgccagt gtgatggata tctgcagaat tcgccctttt   8400
gggccctgta cacctaggat ccgtcgacac tggatggcgg cgttagtatc gaatcgacag   8460
cagtatagcg accagcattc acatacgatt gacgcatgat attactttct gcgcacttaa   8520
cttcgcatct gggcagatga tgtcgaggcg aaaaaaaata taaatcacgc taacatttga   8580
ttaaaataga acaactacaa tataaaaaaa ctatacaaat gacaagttct tgaaaacaag   8640
aatcttttta ttgtcagtac tgattagaaa aactcatcga gcatcaaatg aaactgcaat   8700
ttattcatat caggattatc aataccatat ttttgaaaaa gccgtttctg taatgaagga   8760
gaaaactcac cgaggcagtt ccataggatg gcaagatcct ggtatcggtc tgcgattccg   8820
actcgtccaa catcaataca acctattaat ttcccctcgt caaaaataag gttatcaagt   8880
gagaaatcac catgagtgac gactgaatcc ggtgagaatg gcaaaagctt atgcatttct   8940
ttccagactt gttcaacagg ccagccatta cgctcgtcat caaaatcact cgcatcaacc   9000
aaaccgttat tcattcgtga ttgcgcctga gcgagacgaa atacgcgatc gctgttaaaa   9060
ggacaattac aaacaggaat cgaatgcaac cggcgcagga acactgccag cgcatcaaca   9120
atattttcac ctgaatcagg atattcttct aatacctgga atgctgtttt gccggggatc   9180
gcagtggtga gtaaccatgc atcatcagga gtacggataa aatgcttgat ggtcggaaga   9240
ggcataaatt ccgtcagcca gtttagtctg accatctcat ctgtaacatc attggcaacg   9300
```

-continued

```
ctacctttgc catgtttcag aaacaactct ggcgcatcgg gcttcccata caatcgatag   9360
attgtcgcac ctgattgccc gacattatcg cgagcccatt tatacccata taaatcagca   9420
tccatgttgg aatttaatcg cggcctcgaa acgtgagtct tttccttacc catggttgtt   9480
tatgttcgga tgtgatgtga gaactgtatc ctagcaagat tttaaaagga agtatatgaa   9540
agaagaacct cagtggcaaa tcctaacctt ttatatttct ctacaggggc gcggcgtggg   9600
gacaattcaa cgcgtctgtg aggggagcgt ttccctgctc gcaggtctgc agcgaggagc   9660
cgtaattttt gcttcgcgcc gtgcggccat caaaatgtat ggatgcaaat gattatacat   9720
ggggatgtat gggctaaatg tacgggcgac agtcacatca tgcccctgag ctgcgcacgt   9780
caagactgtc aaggagggta ttctgggcct ccatgtcgct ggccgggtga cccggcgggg   9840
acgaggcctt aagttcgaac gtacgagctc cggattatcg atgataagct gtcaaagatg   9900
agaattaatt ccacggacta tagactatac tagatactcc gtctactgta cgatacactt   9960
ccgctcaggt ccttgtcctt taacgaggcc ttaccactct tttgttactc tattgatcca  10020
gctcagcaaa ggcagtgtga tctaagattc tatcttcgcg atgtagtaaa actagctaga  10080
ccgagaaaga gactagaaat gcaaaaggca cttctacaat ggctgccatc attattatcc  10140
gatgtgacgc tgcagcttct caatgatatt cgaatacgct ttgaggagat acagcctaat  10200
atccgacaaa ctgttttaca gatttacgat cgtacttgtt acccatcatt gaattttgaa  10260
catccgaacc tgggagtttt ccctgaaaca gatagtatat ttgaacctgt ataataatat  10320
atagtctagc gctttacgga agacaatgta tgtatttcgg ttcctggaga aactattgca  10380
tctattgcat aggtaatctt gcacgtcgca tccccggttc attttctgcg tttccatctt  10440
gcacttcaat agcatatctt tgttaacgaa gcatctgtgc ttcattttgt agaacaaaaa  10500
tgcaacgcga gagcgctaat ttttcaaaca aagaatctga gctgcatttt tacagaacag  10560
aaatgcaacg cgaaagcgct attttaccaa cgaagaatct gtgcttcatt tttgtaaaac  10620
aaaaatgcaa cgcgacgaga gcgctaattt ttcaaacaaa gaatctgagc tgcattttta  10680
cagaacagaa atgcaacgcg agagcgctat tttaccaaca aagaatctat acttcttttt  10740
tgttctacaa aaatgcatcc cgagagcgct atttttctaa caaagcatct tagattactt  10800
tttttctcct ttgtgcgctc tataatgcag tctcttgata actttttgca ctgtaggtcc  10860
gttaaggtta gaagaaggct actttggtgt ctattttctc ttccataaaa aaagcctgac  10920
tccacttccc gcgtttactg attactagcg aagctgcggg tgcatttttt caagataaag  10980
gcatccccga ttatattcta taccgatgtg gattgcgcat actttgtgaa cagaaagtga  11040
tagcgttgat gattcttcat tggtcagaaa attatgaacg gtttcttcta ttttgtctct  11100
atatactacg tataggaaat gtttacattt tcgtattgtt ttcgattcac tctatgaata  11160
gttcttacta caattttttt gtctaaagag taatactaga gataaacata aaaaatgtag  11220
aggtcgagtt tagatgcaag ttcaaggagc gaaaggtgga tgggtaggtt atatagggat  11280
atagcacaga gatatatagc aaagagatac ttttgagcaa tgtttgtgga agcggtattc  11340
gcaatgccgg ctttccccgt caagctctaa atcgggggct ccctttaggg ttccgattta  11400
gtgctttacg gcacctcgac cccaaaaaac ttgattaggg tgatggttca cgtagtgggc  11460
catcgccctg atagacggtt tttcgccctt tgacgttgga gtccacgttc tttaatagtg  11520
gactcttgtt ccaaactgga acaacactca accctatctc ggtctattct tttgatttat  11580
aagggatttt gccgatttcg gcctattggt taaaaaatga gctgatttaa caaaaattta  11640
```

-continued

```
acgcgaattt taacaaaata ttaacgttta caatttcctg atgcggtatt ttctccttac  11700
gcatctgtgc ggtatttcac accgcagggt aataactgat ataattaaat tgaagctcta  11760
atttgtgagt ttagtataca tgcatttact tataatacag tttttagtt ttgctggccg  11820
catcttctca aatatgcttc ccagcctgct tttctgtaac gttcaccctc taccttagca  11880
tcccttccct ttgcaaatag tcctcttcca acaataataa tgtcagatcc tgtagagacc  11940
acatcatcca cggttctata ctgttgaccc aatgcgtctc ccttgtcatc taaacccaca  12000
ccgggtgtca taatcaacca atcgtaacct tcatctcttc cacccatgtc tctttgagca  12060
ataaagccga taacaaaatc tttgtcgctc ttcgcaatgt caacagtacc cttagtatat  12120
tctccagtag atagggagcc cttgcatgac aattctgcta acatcaaaag gcctctaggt  12180
tcctttgtta cttcttctgc cgcctgcttc aaaccgctaa caatacctgg gcccaccaca  12240
ccgtgtgcat tcgtaatgtc tgcccattct gctattctgt atacacccgc agagtactgc  12300
aatttgactg tattaccaat gtcagcaaat tttctgtctt cgaagagtaa aaaattgtac  12360
ttggcggata atgcctttag cggcttaact gtgccctcca tggaaaaatc agtcaagata  12420
tccacatgtg tttttagtaa acaaattttg ggacctaatg cttcaactaa ctccagtaat  12480
tccttggtgg tacgaacatc caatgaagca cacaagtttg tttgcttttc gtgcatgata  12540
ttaaatagct tggcagcaac aggactagga tgagtagcag cacgttcctt atatgtagct  12600
ttcgacatga tttatcttcg tttcctgcag gtttttgttc tgtgcagttg ggttaagaat  12660
actgggcaat ttcatgtttc ttcaacacta catatgcgta tatataccaa tctaagtctg  12720
tgctccttcc ttcgttcttc cttctgttcg gagattaccg aatcaaaaaa atttcaaaga  12780
aaccgaaatc aaaaaaaaga ataaaaaaaa aatgatgaat tgaattgaaa agcgtggtgc  12840
actctcagta caatctgctc tgatgccgca tagttaagcc agccccgaca cccgccaaca  12900
cccgctgacg cgccctgacg ggcttgtctg ctcccggcat ccgcttacag acaagctgtg  12960
accgtctccg ggagctgcat gtgtcagagg ttttcaccgt catcaccgaa acgcgcga    13018
```

YEAST STRAINS ENGINEERED TO PRODUCE ETHANOL FROM ACETIC ACID AND GLYCEROL

FIELD OF THE INVENTION

The present invention relates to metabolic engineering in microorganisms such as yeast. In particular the invention relates to yeast strains that have been engineered to produce ethanol from acetic acid and glycerol. In addition to acetic acid and glycerol, the yeast strain may also consume hexoses and pentoses for the production of ethanol. The invention further relates to the processes wherein the engineered strains of the invention produce ethanol from acetic acid and glycerol.

BACKGROUND OF THE INVENTION

Second generation bioethanol is produced from e.g. lignocellulosic fractions of plant biomass that is hydrolysed to free monomeric sugars, such as hexoses and pentoses, for fermentation to ethanol. Lignocellulosic hydrolysates contain high amounts of acetic acid, which is a potent inhibitor of the fermentative capacities of microorganisms used for ethanol production such as yeasts.

Sonderegger et al. (2004, Appl. Environ. Microbiol. 70: 2892-2897) disclose heterologous expression of phosphotransacetylase and acetaldehyde dehydrogenase in xylose-fermenting *Saccharomyces cerevisiae* strain. In combination with the native phosphoketolase, Sonderegger et al. thereby created a functional phosphoketolase pathway that is capable of net reoxidation of NADH generated by the heterologous expression of a xylose reductase and xylitol dehydrogenase that are used for xylose utilization in the strain.

Guadalupe et al. (2009, Appl. Environ. Microbiol. doi: 10.1128/AEM.01772-09) disclose a *Saccharomyces cerevisiae* strain wherein production of the by-product glycerol is eliminated by disruption of the endogenous NAD-dependent glycerol 3-phosphate dehydrogenase genes (GPD1 and GPD2). Expression of the *E. coli* mhpF gene, encoding the acetylating NAD-dependent acetaldehyde dehydrogenase restored the ability of the GPD-disrupted strain to grow anaerobically by supplementation with of the medium with acetic acid.

Yu et al. (2010, Bioresour. Technol. 101(11):4157-61. Epub 2010 Feb. 9) disclose *Saccharomyces cerevisiae* strains metabolically engineered for improved ethanol production from glycerol by simultaneous overexpression of glycerol dehydrogenase (GCY), dihydroxyacetone kinase (DAK) and the glycerol uptake protein (GUP1).

Lee and Dasilva (2006, Metab Eng. 8(1):58-65) disclose the yeast *Saccharomyces cerevisiae* engineered to produce 1,2-propanediol from glycerol by inter alia introducing expression of the *Escherichia coli* mgs and gldA genes.

It is an object of the present invention to provide for yeasts that are capable of producing ethanol from acetic acid and glycerol (and hexoses and pentoses), as well as processes wherein these strains are used for the production of ethanol and/or other fermentation products.

DESCRIPTION OF THE INVENTION

Definitions

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The terms "sequence identity" or "sequence similarity" means that two (poly)peptide or two nucleotide sequences, when optimally aligned, preferably over the entire length (of at least the shortest sequence in the comparison) and maximizing the number of matches and minimizes the number of gaps such as by the programs ClustalW (1.83), GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). A preferred multiple alignment program for aligning protein sequences of the invention is ClustalW (1.83) using a blosum matrix and default settings (Gap opening penalty:10; Gap extension penalty: 0.05). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1):387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or expression construct" refer to nucleotide sequences that are capable of affecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

"Fungi" (singular fungus) are herein understood as heterotrophic eukaryotic microorganism that digest their food externally, absorbing nutrient molecules into their cells.

Fungi are a separate kingdom of eukaryotic organisms and include yeasts, molds, and mushrooms. The terms fungi, fungus and fungal as used herein thus expressly includes yeasts as well as filamentous fungi.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'nontranslated sequence (3'end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. In this context, the use of only "homologous" sequence elements allows the construction of "self-cloned" genetically modified organisms (GMO's) (self-cloning is defined herein as in European Directive 98/81/EC Annex II). When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous and exogenous nucleic acids or proteins are not endogenous to the cell into which it is introduced, but have been obtained from another cell or synthetically or recombinantly produced. Generally, though not necessarily, such nucleic acids encode proteins, i.e. exogenous proteins, that are not normally produced by the cell in which the DNA is transcribed or expressed. Similarly exogenous RNA encodes for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The "specific activity" of an enzyme is herein understood to mean the amount of activity of a particular enzyme per amount of total host cell protein, usually expressed in units of enzyme activity per mg total host cell protein. In the context of the present invention, the specific activity of a particular enzyme may be increased or decreased as compared to the specific activity of that enzyme in an (otherwise identical) wild type host cell.

"Anaerobic conditions" or an anaerobic fermentation process is herein defined as conditions or a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors.

DETAILED DESCRIPTION OF THE INVENTION

Expression of an exogenous acetaldehyde dehydrogenase in yeast allows the yeast to convert acetic acid, which may be present in high amounts in lignocellulosic hydrolysates, to ethanol. The NADH dependent reduction of acetic acid to ethanol has been proposed as a replacement for glycerol formation as a redox sink in anaerobic glucose-grown cultures of *S. cerevisiae*, thus providing a stoichiometric basis for elimination of glycerol production (as byproduct) during industrial ethanol production and consequently a higher ethanol yield (Guadalupe et al. supra). However, the stoichiometry of these reactions is such that the reduction of one molecule of acetic acid to ethanol would require two glycerol molecules not being produced. The present inventors have found however, that in practice the amount of acetic acid that typically is present in industrial lignocellulosic hydrolysates is such that the amount of NADH required for it to be reduced to ethanol exceeds the amount of NADH that would become available from preventing glycerol production in yeasts grown under anaerobic conditions. The present inventors have now surprisingly found that much higher amounts of acetic acid can be reduced to ethanol by simultaneous consumption of glycerol by the yeast, rather than by preventing its production.

Large amounts of glycerol are generated as a by-product in biodiesel production from transesterification reactions using vegetable oils or animal fats and an alcohol. The availability of crude glycerol is therefore predicted to increase over the next years as a result of the growth in biodiesel production worldwide. Consequently large amounts of glycerol will be available at low cost. The present invention provides means and methods for valorising glycerol, obtained e.g. as by-product from biodiesel production, by converting it to ethanol that may be used as biofuel. At the same time the present invention addresses the problem of high amounts of acetic acid that are present in lignocellulosic hydrolysates and which inhibit the fermentative capacities of yeasts producing ethanol from these hydrolysates. A further advantage of the present invention is that by leaving the high-osmolarity glycerol response pathway intact in the yeast cells of the invention (as opposed to strains wherein (all) glycerolphosphate dehydrogenase genes are inactivated as described by Guadalupe et al. supra), more robust yeast strains are obtained that are better capable of handling osmotic stress that may occur under industrial fermentations conditions.

In a first aspect the invention relates to a fungal host cell comprising an exogenous gene coding for a enzyme with the ability to reduce acetylCoA into acetaldehyde, which gene confers to the cell the ability to convert acetic acid into ethanol. An enzyme with the ability to reduce acetylCoA into acetaldehyde is herein understood as an enzyme which catalyze the reaction (ACDH; EC 1.2.1.10):

acetaldehyde+NAD+Coenzyme A↔acetyl-Coenzyme A+NADH+H.

Thus, the enzyme catalyzes the conversion of acetylCoA into acetaldehyde (and vice versa) and is also referred to as an (acetylating NAD-dependent) acetaldehyde dehydrogenase or an acetyl-CoA reductase. The enzyme may be a bifunctional enzyme which further catalyzes the conversion of acetaldehyde into ethanol (and vice versa; see below). For convenience we shall refer herein to an enzyme having at least the ability to reduce acetylCoA into either acetaldehyde or ethanol as an "acetaldehyde dehydrogenase". It is further understood herein the fungal host cell has endogenous acetyl-CoA synthetase and alcohol dehydrogenase activities which allow the cell, being provided with acetaldehyde dehydrogenase activity, to complete the conversion of acetic acid into ethanol.

The exogenous gene may encode for a monofunctional enzyme having only acetaldehyde dehydrogenase activity (i.e. an enzyme only having the ability to reduce acetylCoA into acetaldehyde) such as e.g. the acetaldehyde dehydrogenase encoded by the *E. coli* mhpF gene. A suitable exogenous gene coding for an enzyme with acetaldehyde dehydrogenase activity comprises a nucleotide sequence coding for an amino acid sequence with at least 45, 50, 60, 65, 70, 75, 80, 85, 90, 95, 98, 99% amino acid sequence identity with SEQ ID NO: 1. Suitable examples of prokaryotes comprising monofunctional enzymes with acetaldehyde dehydrogenase activity are provided in Table 1. The amino acid sequences of these monofunctional enzymes are available in public databases and can be used by the skilled person to design codon-optimised nucleotide sequences coding for the corresponding monofunctional enzyme (see e.g. SEQ ID NO: 2).

TABLE 1

Enzymes with acetaldehyde dehydrogenase activity related to *E. coli* mhpF

| Organism | Amino acid identity (%) |
|---|---|
| *Escherichia coli* str. K12 substr. MG1655 | 100% |
| *Shigella sonnei* | 100% |
| *Escherichia coli* IAI39 | 99% |
| *Citrobacter youngae* ATCC 29220 | 93% |
| *Citrobacter* sp. 30_2 | 92% |
| *Klebsiella pneumoniae* 342) | 87% |
| *Klebsiella variicola* | 87% |
| *Pseudomonas putida* | 81% |
| *Ralstonia eutropha* JMP134 | 82% |
| *Burkholderia* sp. H160 | 81% |
| *Azotobacter vinelandii* DJ | 79% |
| *Ralstonia metallidurans* CH34 | 70% |
| *Xanthobacter autotrophicus* Py2 | 67% |
| *Burkholderia cenocepacia* J2315 | 68% |
| *Frankia sp.* EAN1pec | 67% |
| *Polaromonas* sp. JS666 | 68% |
| *Burkholderia phytofirmans* PsJN | 70% |
| *Rhodococcus opacus* B4 | 64% |

Preferably, the host cell comprises an exogenous gene coding for a bifunctional enzyme with acetaldehyde dehydrogenase and alcohol dehydrogenase activity, which gene confers to the cell the ability to covert acetic acid into ethanol. The advantage of using a bifunctional enzyme with acetaldehyde dehydrogenase and alcohol dehydrogenase activities as opposed to separate enzymes for each of the acetaldehyde dehydrogenase and alcohol dehydrogenase activities, is that it allows for direct channeling of the intermediate between enzymes that catalyze consecutive reactions in a pathway offers the possibility of an efficient, exclusive, and protected means of metabolite delivery. Substrate channeling thus decreases transit time of intermediates, prevents loss of intermediates by diffusion, protects labile intermediates from solvent, and forestalls entrance of intermediates into competing metabolic pathways. The bifunctional enzyme therefore allows for a more efficient conversion of acetic acid into ethanol as compared to the separate acetaldehyde dehydrogenase and alcohol dehydrogenase enzymes. A further advantage of using the bifunctional enzyme is that it may also be used in host cells having little or no alcohol dehydrogenase activity under the condition used, such as e.g. anaerobic conditions and/or conditions of catabolite repression.

Bifunctional enzymes with acetaldehyde dehydrogenase and alcohol dehydrogenase activity are known in the art prokaryotes and protozoans, including e.g. the bifunctional enzymes encoded by the *Escherichia coli* adhE and *Entamoeba histolytica* ADH2 genes (see e.g. Bruchaus and Tannich, 1994, J. Biochem. 303: 743-748; Burdette and Zeikus, 1994, J. Biochem. 302: 163-170; Koo et al., 2005, Biotechnol. Lett. 27: 505-510; Yong et al., 1996, Proc Natl Acad Sci USA, 93: 6464-6469). Bifunctional enzymes with acetaldehyde dehydrogenase and alcohol dehydrogenase activity are larger proteins consisting of around 900 amino acids and they are bifunctional in that they exhibit both acetaldehyde dehydrogenase (ACDH; EC 1.2.1.10) and alcohol dehydrogenase activity (ADH; EC 1.1.1.1). The *E. coli* adhE and *Entamoeba histolytica* ADH2 show 45% amino acid identity. Therefore, in one embodiment of the invention, a suitable exogenous gene coding for a bifunctional enzyme with acetaldehyde dehydrogenase and alcohol dehydrogenase activity comprises a nucleotide sequence coding for an amino acid sequence with at least 45, 50, 60, 65, 70, 75, 80, 85, 90, 95, 98, 99% amino acid sequence identity with at least one of SEQ ID NO: 3 and 5. Suitable examples of prokaryotes comprising bifunctional enzymes with acetaldehyde dehydrogenase and alcohol dehydrogenase activity are provided in Tables 2 and 3. The amino acid sequences of these bifunctional enzymes are available in public databases and can be used by the skilled person to design codon-optimised nucleotide sequences coding for the corresponding bifunctional enzyme (see e.g. SEQ ID NO: 4 or 6).

TABLE 2

Bifunctional enzymes with acetaldehyde dehydrogenase and alcohol dehydrogenase activity related to *E. coli* adhE

| Organism | Amino acid identity (%) |
|---|---|
| *Escherichia coli* O157:H7 str. Sakai | 100% |
| *Shigella sonnei* | 100% |
| *Shigella dysenteriae* 1012 | 99% |
| *Klebsiella pneumoniae* 342 | 97% |
| *Enterobacter* sp. 638 | 94% |
| *Yersinia pestis biovar* Microtus str. 91001 | 90% |
| *Serratia proteamaculans* 568 | 90% |
| *Pectobacterium carotovorum* WPP14 | 90% |
| *Sodalis glossinidius* str. 'morsitans' | 87% |
| *Erwinia tasmaniensis* Et1/99 | 86% |
| *Aeromonas hydrophila* ATCC 7966 | 81% |

TABLE 2-continued

Bifunctional enzymes with acetaldehyde dehydrogenase and alcohol dehydrogenase activity related to *E. coli* adhE

| Organism | Amino acid identity (%) |
|---|---|
| *Vibrio vulnificus* YJO16] | 76% |

TABLE 3

Bifunctional enzymes with acetaldehyde dehydrogenase and alcohol dehydrogenase activity related to *Entamoeba histolytica* ADH2

| Organism | Amino acid identity (%) |
|---|---|
| *Entamoeba histolytica* HM-1:IMSS | 99% |
| *Entamoeba dispar* SAW760 | 98% |
| *Mollicutes bacterium* D7 | 65% |
| *Fusobacterium mortiferum* ATCC 9817 | 64% |
| *Actinobacillus succinogenes* 130Z | 63% |
| *Pasteurella multocida* Pm70 | 62% |
| *Mannheimia succiniciproducens* MBEL55E | 61% |
| *Streptococcus* sp. 2_1_36FAA] | 61% |

The exogenous gene coding for the bifunctional enzyme having acetaldehyde dehydrogenase and alcohol dehydrogenase activities, for an enzyme having acetaldehyde dehydrogenase activity, preferably is an expression construct comprising a nucleotide sequence coding for the enzyme operably linked to suitable expression regulatory regions/sequences to ensure expression of the enzyme upon transformation of the expression construct into the host cell of the invention. Thus, the gene or expression construct will at least comprise a promoter that is functional in the host cell operably linked to the coding sequence. The gene or construct may further comprise a 5' leader sequence upstream of the coding region and a 3'-nontranslated sequence (3'end) comprising a polyadenylation site and a transcription termination site downstream of the coding sequence.

In one aspect the invention relates to methods for preparing or constructing the yeast cells of the invention. For this purpose standard genetic and molecular biology techniques are used that are generally known in the art and have e.g. been described by Sambrook and Russell (2001, "Molecular cloning: a laboratory manual" (3rd edition), Cold Spring Harbor Laboratory, Cold Spring Harbor Laboratory Press) and Ausubel et al. (1987, eds., "Current protocols in molecular biology", Green Publishing and Wiley Interscience, New York). Furthermore, the construction of mutated host yeast strains is carried out by genetic crosses, sporulation of the resulting diploids, tetrad dissection of the haploid spores containing the desired auxotrophic markers, and colony purification of such haploid host yeasts in the appropriate selection medium. All of these methods are standard yeast genetic methods known to those in the art. See, for example, Sherman et al., Methods Yeast Genetics, Cold Spring Harbor Laboratory, NY (1978) and Guthrie et al. (Eds.) Guide To Yeast Genetics and Molecular Biology Vol. 194, Academic Press, San Diego (1991).

Suitable promoters for expression of the nucleotide sequence coding for the enzyme having acetaldehyde dehydrogenase and optionally alcohol dehydrogenase activity (as well as other enzymes of the invention; see below) include promoters that are preferably insensitive to catabolite (glucose) repression, that are active under anaerobic conditions and/or that preferably do not require xylose or arabinose for induction. Promoters having these characteristics are widely available and known to the skilled person. Suitable examples of such promoters include e.g. promoters from glycolytic genes such as the phosphofructokinase (PPK), triose phosphate isomerase (TPI), glyceraldehyde-3-phosphate dehydrogenase (GDP, TDH3 or GAPDH), pyruvate kinase (PYK), phosphoglycerate kinase (PGK), glucose-6-phosphate isomerase promoter (PGI1) promoters from yeasts. More details about such promoters from yeast may be found in (WO 93/03159). Other useful promoters are ribosomal protein encoding gene promoters (TEF1), the lactase gene promoter (LAC4), alcohol dehydrogenase promoters (ADH1, ADH4, and the like), the enolase promoter (ENO) and the hexose (glucose) transporter promoter (HXT7). Alternatively, the nucleotide sequence encoding the enzyme having acetaldehyde dehydrogenase and optionally alcohol dehydrogenase activity is overexpressed under anaerobic conditions by using an anoxic promoter such as e.g. the *S. cerevisiae* ANB1 promoter (SEQ ID NO: 19). Other promoters, both constitutive and inducible, and enhancers or upstream activating sequences will be known to those of skill in the art. Preferably the promoter that is operably linked to nucleotide sequence as defined above is homologous to the host cell. Suitable terminator sequences are e.g. obtainable from the cytochrome c1 (CYC1) gene or an alcohol dehydrogenase gene (e.g. ADH1).

To increase the likelihood that the enzyme having acetaldehyde dehydrogenase and optionally alcohol dehydrogenase activities is expressed at sufficient levels and in active form in the transformed host cells of the invention, the nucleotide sequence encoding these enzymes, as well as other enzymes of the invention (see below), are preferably adapted to optimise their codon usage to that of the host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences which have been codon optimised for expression in the fungal host cell in question such as e.g. *S. cerevisiae* cells.

The nucleotide sequence encodes an enzyme having acetaldehyde dehydrogenase and optionally alcohol dehydrogenase activities that is preferably expressed in active form in the transformed host cell. Thus, expression of the nucleotide sequence in the host cell produces an acetaldehyde dehydrogenase with a specific activity of at least 0.005, 0.010, 0.020, 0.050 or 0.10 μmol $min^{-1}$ (mg $protein)^{-1}$, determined as acetyl-CoA dependent rate of NADH reduction in cell extracts of the transformed host cell at 30° C. as described in the Examples herein.

The host cell to be transformed with a nucleic acid construct comprising a nucleotide sequence encoding an enzyme with acetaldehyde dehydrogenase and optionally alcohol dehydrogenase preferably is a yeast host cell. Preferably the host cell is a cultured cell. The host cell of the invention, preferably is a host capable of active or passive pentose (xylose and preferably also arabinose) transport into the cell. The host cell preferably contains active glycolysis. The host cell may further preferably contains an endogenous pentose phosphate pathway and may contain endogenous xylulose kinase activity so that xylulose isomerised from xylose may be metabolised to pyruvate. The host further preferably contains enzymes for conversion of a pentose (preferably through pyruvate) to a desired fermentation product such as ethanol, lactic acid, 3-hydroxy-propionic acid, acrylic acid, 1,3-propane-diol, butanols (1-butanol, 2-butanol, isobutanol) and isoprenoid-derived products. A particularly preferred host cell is a yeast cell that is naturally capable of alcoholic fermentation, preferably, anaerobic alcoholic fermentation. The yeast host cell further preferably has a high tolerance to ethanol, a high tolerance to low pH (i.e. capable of growth at a pH lower than 5, 4, or 3) and towards organic acids like lactic acid, acetic acid or formic acid and sugar degradation products such as furfural and hydroxy-methylfurfural, and a high tolerance to elevated temperatures. Any of these characteristics or activities of the host cell may be naturally present in the host cell or may be introduced or modified by genetic modification, preferably by self cloning or by the methods of the invention described below. A suitable cell is a cultured cell, a cell that may be cultured in fermentation process e.g. in submerged or solid state fermentation. Particularly suitable cells are eukaryotic microorganism like e.g. fungi, however, most suitable for use in the present inventions are yeasts.

Yeasts are herein defined as eukaryotic microorganisms and include all species of the subdivision Eumycotina (Yeasts: characteristics and identification, J. A. Barnett, R. W. Payne, D. Yarrow, 2000, 3rd ed., Cambridge University Press, Cambridge UK; and, The yeasts, a taxonomic study, C. P. Kurtzman and J. W. Fell (eds) 1998, $4^{th}$ ed., Elsevier Science Publ. B.V., Amsterdam, The Netherlands) that predominantly grow in unicellular form. Yeasts may either grow by budding of a unicellular thallus or may grow by fission of the organism. Preferred yeasts cells for use in the present invention belong to the genera *Saccharomyces, Kluyveromyces, Candida, Pichia, chizosaccharomyces, Hansenula, Kloeckera, Schwanniomyces*, and *Yarrowia*. Preferably the yeast is capable of anaerobic fermentation, more preferably anaerobic alcoholic fermentation. Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae, S. exiguus, S. bayanus, K. lactis, K. marxianus* and *Schizosaccharomyces pombe.*

In a further embodiment, the host cell of the invention further comprises a genetic modification that introduces $NAD^+$-linked glycerol dehydrogenase activity in the cell. The glycerol dehydrogenase encoded by the endogenous yeast GCY1 gene appears to be specific for the cofactor $NADP^+$ (EC 1.1.1.72) as opposed to $NAD^+$ (EC 1.1.1.6). Yeasts such as *S. cerevisiae* appear to lack $NAD^+$-dependent glycerol dehydrogenase activity (EC 1.1.1.6) (see e.g. KEGG pathway 00561). An $NAD^+$-linked glycerol dehydrogenase is herein understood as an enzyme that catalyzes the chemical reaction (EC 1.1.1.6):

$$\text{glycerol}+\text{NAD}\leftrightarrow\text{glycerone}+\text{NADH}+\text{H}^+$$

Other names in common use include glycerin dehydrogenase and glycerol:NAD+2-oxidoreductase.

Preferably the genetic modification that introduces $NAD^+$-linked glycerol dehydrogenase activity in the host cell is the expression of an $NAD^+$-linked glycerol dehydrogenase that is heterologous to the host cell. More preferably, the nucleotide sequence for expression of a heterologous glycerol dehydrogenase in the cells of the invention is a sequence encoding a bacterial glycerol dehydrogenase which use NAD as cofactor (EC 1.1.1.6). A suitable example of a bacterial $NAD^+$-linked glycerol dehydrogenase for expression in a host cell of the invention is e.g. the gldA gene from *E. coli* described by Truniger and Boos (1994, J Bacteriol. 176(6):1796-1800), the expression of which in yeast has already been reported (Lee and Dasilva, 2006, Metab Eng. 8(1):58-65). Preferably, the nucleotide sequence encoding a heterologous glycerol dehydrogenase comprises a nucleotide sequence coding for an amino acid sequence with at least 45, 50, 60, 65, 70, 75, 80, 85, 90, 95, 98, 99% amino acid sequence identity with SEQ ID NO: 7 or a nucleotide sequence coding for an amino acid sequence having one or several substitutions, insertions and/or deletions as compared to SEQ ID NO: 7. In a preferred embodiment a codon-optimised (see above) nucleotide sequence encoding the heterologous glycerol dehydrogenase is over-expressed, such as e.g. a codon-optimised nucleotide sequence encoding the amino acid sequence of the glycerol dehydrogenase of SEQ ID NO: 7. Such a codon-optimised nucleotide sequence is e.g. provided in SEQ ID NO: 21 (positions 10-1113; CAI=0.976).

For overexpression of the nucleotide sequence encoding the glycerol dehydrogenase, the nucleotide sequence (to be overexpressed) is placed in an expression construct wherein it is operably linked to suitable expression regulatory regions/sequences to ensure overexpression of the glycerol dehydrogenase enzyme upon transformation of the expression construct into the host cell of the invention (see above). Suitable promoters for (over)expression of the nucleotide sequence coding for the enzyme having glycerol dehydrogenase activity include promoters that are preferably insensitive to catabolite (glucose) repression, that are active under anaerobic conditions and/or that preferably do not require xylose or arabinose for induction. Examples of such promoters are given above. Expression of the nucleotide sequence in the host cell produces a specific $NAD^+$-linked glycerol dehydrogenase activity of at least 0.2, 0.5, 1.0, 2.0, or 5.0 U $min^{-1}$ (mg protein)$^{-1}$, determined in cell extracts of the transformed host cells at 30° C. as described in the Examples herein.

In a further embodiment, the host cell of the invention further comprises a genetic modification that increases the specific activity of dihydroxyacetone kinase in the cell. Transcriptome data has shown that the endogenous DAK1 dihydroxyacetone kinase is already expressed at high levels in *S. cerevisiae*. A further increase of dihydroxyacetone kinase activity in the cells of the invention may therefore not be strictly necessary. However, in a preferred, embodiment, for optimal conversion rates, the host cell of the invention thus comprises a genetic modification that increases the specific activity of dihydroxyacetone kinase in the cell. A dihydroxyacetone kinase is herein understood as an enzyme that catalyzes the chemical reaction ((EC 2.7.1.29):

$$\text{ATP}+\text{glycerone}\leftrightarrow\text{ADP}+\text{glycerone phosphate}$$

Other names in common use include glycerone kinase, ATP:glycerone phosphotransferase and (phosphorylating) acetol kinase. It is understood that glycerone and dihydroxyacetone are the same molecule. Preferably the genetic modification causes overexpression of a dihydroxyacetone kinase, e.g. by overexpression of a nucleotide sequence encoding a dihydroxyacetone kinase. The nucleotide sequence encoding the dihydroxyacetone kinase may be endogenous to the cell or may be a dihydroxyacetone kinase that is heterologous to the cell. Nucleotide sequences that may be used for overexpression of dihydroxyacetone kinase in the cells of the invention are e.g. the dihydroxyacetone kinase genes from *S. cerevisiae* (DAK1) and (DAK2) as e.g. described by Molin et al. (2003, J. Biol. Chem. 278:1415-1423). Preferably, the nucleotide sequence encoding the dihydroxyacetone kinase comprises an amino acid sequence with at least 45, 50, 60, 65, 70, 75, 80, 85, 90, 95, 98, 99% amino acid sequence identity with at least one of SEQ ID NO's: 8 and 9. In a preferred embodiment a codon-optimised (see above) nucleotide sequence encoding the dihydroxyacetone kinase is overexpressed, such as e.g. a codon optimised nucleotide sequence encoding the dihydroxyacetone kinase of SEQ ID NO: 8 or a codon optimised nucleotide sequence encoding the dihydroxyacetone kinase of SEQ ID NO: 9. A preferred nucleotide sequence for overexpression of a dihydroxyacetone kinase is a nucleotide sequence encoding a dihydroxyacetone kinase comprises an amino acid sequence with at least 45, 50, 60, 65, 70, 75, 80, 85, 90, 95, 98, 99% amino acid sequence identity with at least one of SEQ ID NO's: 8 (*S. cerevisiae* (DAK1) or having one or several substitutions, insertions and/or deletions as compared to SEQ ID NO: 8.

Nucleotide sequences that may be used for overexpression of a heterologous dihydroxyacetone kinase in the cells of the invention are e.g. sequences encoding bacterial dihydroxyacetone kinases such as the dhaK gene from *Citrobacter freundii* e.g. described by Daniel et al. (1995, J. Bacteriol. 177:4392-4401). Preferably, the nucleotide sequence encoding a heterologous dihydroxyacetone kinase comprises a nucleotide sequence coding for an amino acid sequence with at least 45, 50, 60, 65, 70, 75, 80, 85, 90, 95, 98, 99% amino acid sequence identity with SEQ ID NO: 25 or a nucleotide sequence coding for an amino acid sequence having one or several substitutions, insertions and/or deletions as compared to SEQ ID NO: 25. In a preferred embodiment a codon-optimised (see above) nucleotide sequence encoding the heterologous dihydroxyacetone kinase is overexpressed, such as e.g. a codon optimised nucleotide sequence encoding the amino acid sequence of the dihydroxyacetone kinase of SEQ ID NO: 25. Such a codon-optimised nucleotide sequence is e.g. provided in SEQ ID NO: 26 (positions 10-1668).

For overexpression of the nucleotide sequence encoding the dihydroxyacetone kinase, the nucleotide sequence (to be overexpressed) is placed in an expression construct wherein it is operably linked to suitable expression regulatory regions/sequences to ensure overexpression of the dihydroxyacetone kinase enzyme upon transformation of the expression construct into the host cell of the invention (see above). Suitable promoters for (over)expression of the nucleotide sequence coding for the enzyme having dihydroxyacetone kinase activity include promoters that are preferably insensitive to catabolite (glucose) repression, that are active under anaerobic conditions and/or that preferably do not require xylose or arabinose for induction. Examples of such promoters are given above. In the cells of the invention, a dihydroxyacetone kinase to be overexpressed is preferably overexpressed by at least a factor 1.1, 1.2, 1.5, 2, 5, 10 or 20 as compared to a strain which is genetically identical except for the genetic modification causing the overexpression. Preferably, the dihydroxyacetone kinase is overexpressed under anaerobic conditions by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity (specific activity in the cell), the steady state level of the enzyme's protein as well as to the steady state level of the transcript coding for the enzyme in the cell. Overexpression of the nucleotide sequence in the host cell produces a specific dihydroxyacetone kinase activity of at least 0.002, 0.005, 0.01, 0.02 or 0.05 U $min^{-1}$ (mg protein)$^{-1}$, determined in cell extracts of the transformed host cells at 30° C. as described in the Examples herein.

In a further embodiment, the host cell of the invention further comprises a genetic modification that increases transport of glycerol into the cell. Preferably, the genetic modification that increases transport of glycerol into the cell preferably is a genetic modification that causes overexpression of a nucleotide sequence encoding at least one of a glycerol uptake protein and a glycerol channel.

A glycerol uptake protein is herein understood as a multimembrane-spanning protein that belongs to the included in the membrane bound O-acyltransferases (MBOAT) superfamily including e.g. the *S. cerevisiae* glycerol uptake proteins encoded by the GUP1 and GUP2 genes. Preferably the genetic modification causes overexpression of a glycerol uptake protein, e.g. by overexpression of a nucleotide sequence encoding a glycerol uptake protein. The nucleotide sequence encoding the glycerol uptake protein may be endogenous to the cell or may be a glycerol uptake protein that is heterologous to the cell. Nucleotide sequences that may be used for overexpression of glycerol uptake protein in the cells of the invention are e.g. the glycerol uptake protein genes from *S. cerevisiae* (GUP1) and (GUP2) and orthologues thereof as e.g. described by Neves et al. (2004, FEMS Yeast Res. 5:51-62). Preferably, the nucleotide sequence encoding the glycerol uptake protein comprises a nucleotide sequence coding for an amino acid sequence with at least 45, 50, 60, 65, 70, 75, 80, 85, 90, 95, 98, 99% amino acid sequence identity with at least one of SEQ ID NO's: 10 (Gup1p) and 11 (Gup2p). In a preferred embodiment a codon-optimised (see above) nucleotide sequence encoding the glycerol uptake protein is overexpressed, such as e.g. a codon optimised nucleotide sequence encoding the glycerol uptake protein SEQ ID NO: 10 or a codon optimised nucleotide sequence encoding the glycerol uptake protein of SEQ ID NO: 11. Although the exact nature of the influence of GUP1 on glycerol transport is not yet clear, Yu et al. (2010, supra) have shown that overexpression of GUP1 in *S. cerevisiae* improves ethanol production on glycerol grown cells. A preferred nucleotide sequence for overexpression of a glycerol uptake protein is therefore a nucleotide sequence encoding a glycerol uptake protein that is capable of rescuing salt stress-associated phenotype of a *S. cerevisiae* gup1Δ mutant by complementation as described by Neves et al. (2004, supra). Such complementing orthologues of *S. cerevisiae* GUP1 include nucleotide sequences encoding amino acid sequences having at least 60, 68, 72, 75, 80, 85, 90, 95, 98, 99% identity with the amino acid sequence of SEQ ID NO: 10 and may be obtained from yeast species belonging to the genera of *Saccharomyces, Zygosaccharomyces, Kluyveromyces, Candida, Pichia, Hansenula, Kloeckera, Schwanniomyces*, and *Yarrowia*.

A glycerol channel is herein understood as a member of the MIP family of channel proteins reviewed by Reizer et al. (1993, CRC Crit. Rev. Biochem. Mol. Biol., 28: 235-257), which channel proteins comprise a 250-280 amino acid transmembrane domain consisting of six membrane-spanning domains and have at least 30, 35, 40, 45, 50, 60, 70, 80, 90, 95, 98 or 99% amino acid identity, or at least 55, 60, 65, 70, 80, 90, 95, 98 or 99% amino acid similarity with the amino acid sequence between amino acids 250 and 530 of SEQ ID NO: 12, the *S. cerevisiae* FPS1 aquaglyceroporin. Nucleotide sequences that may be used for overexpression of a glycerol channel in the cells of the invention include nucleotide sequences encoding the yeast aquaglyceroporin FPS1 gene from e.g. *S. cerevisiae* (Van Aelst et al., 1991, EMBO J. 10:2095-2104) and orthologues thereof from other yeasts including *Kluyveromyces lactis, Kluyveromyces marxianus* and *Zygosaccharomyces rouxii* as e.g. described by Neves et al. (2004, supra). However, the use of bacterial or plant glycerol channels is not excluded as e.g. Luyten et al. (1995, EMBO J. 14:1360-1371) have shown that the *E. coli* glycerol facilitator, having only 30% sequence identity with the amino acid sequence between amino acids 250 and 530 of the *S. cerevisiae* FPS1 aquaglyceroporin, can complement glycerol uptake in a *S. cerevisiae* fps1Δ mutant. The nucleotide sequence encoding the glycerol channel may be endogenous to the cell or may be a glycerol channel that is heterologous to the cell. In a preferred embodiment a codon-optimised (see above) nucleotide sequence encoding the glycerol channel is overexpressed, such as e.g. a codon optimised nucleotide sequence encoding the aquaglyceroporin of SEQ ID NO: 12.

For overexpression of the nucleotide sequence encoding the glycerol uptake protein and/or the glycerol channel protein, the nucleotide sequence (to be overexpressed) is placed in an expression construct wherein it is operably linked to suitable expression regulatory regions/sequences to ensure overexpression of the glycerol uptake protein and/or the glycerol channel protein upon transformation of the expression construct into the host cell of the invention (see above). Suitable promoters for (over)expression of the nucleotide sequence coding for the glycerol uptake protein and/or the glycerol channel protein include promoters that are preferably insensitive to catabolite (glucose) repression, that are active under anaerobic conditions and/or that preferably do not require xylose or arabinose for induction. Examples of such promoters are given above. In the cells of the invention, a glycerol uptake protein and/or a glycerol channel protein to be overexpressed are preferably overexpressed by at least a factor 1.1, 1.2, 1.5, 2, 5, 10 or 20 as compared to a strain which is genetically identical except for the genetic modification causing the overexpression. Preferably, the glycerol uptake protein and/or the glycerol channel protein are overexpressed under anaerobic conditions by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity (specific activity in the cell), the steady state level of the enzyme's protein as well as to the steady state level of the transcript coding for the enzyme in the cell.

In a preferred embodiment of the host cell of the invention, the expression of the glycerol channel protein as defined above is reduced or inactivated. A genetic modification reducing or inactivating the expression of the glycerol channel protein may be useful to reduce or prevent transport of glycerol out of the cell. Preferably, the reduction or inactivation of the expression of the glycerol channel protein is combined with overexpression of the nucleotide sequence encoding the glycerol uptake protein as defined above.

In a further embodiment, the host cell of the invention further comprises a genetic modification that increases the specific acetyl-CoA synthetase activity in the cell, preferably under anaerobic conditions as this activity is rate-limiting under these conditions. Acetyl-CoA synthetase or acetate-CoA ligase (EC 6.2.1.1) is herein understood as an enzyme that catalyzes the formation of a new chemical bond between acetate and coenzyme A (CoA). Preferably the genetic modification causes overexpression of a acetyl-CoA synthetase, e.g. by overexpression of a nucleotide sequence encoding a acetyl-CoA synthetase. The nucleotide sequence encoding the acetyl-CoA synthetase may be endogenous to the cell or may be a acetyl-CoA synthetase that is heterologous to the cell. Nucleotide sequences that may be used for overexpression of acetyl-CoA synthetase in the cells of the invention are e.g. the acetyl-CoA synthetase genes from *S. cerevisiae* (ACS1 and ACS2) as e.g. described by de Jong-Gubbels et al. (1998, FEMS Microbiol Lett. 165: 15-20). Preferably, the nucleotide sequence encoding the acetyl-CoA synthetase comprises an amino acid sequence with at least 45, 50, 60, 65, 70, 75, 80, 85, 90, 95, 98, 99% amino acid sequence identity with at least one of SEQ ID NO's: 13 and 14.

In one embodiment, the nucleotide sequence that is overexpressed encodes an acetyl-CoA synthetase with a high affinity for acetate. Use of an acetyl-CoA synthetase with a high affinity for acetate is preferred for conditions under which there is a relatively low concentration of acetic acid in the culture medium, e.g. no more than 2 g acetic acid/L culture medium. An acetyl-CoA synthetase with a high affinity for acetate is herein defined as an acetyl-CoA synthetase with a higher affinity for acetate than the acetyl-CoA synthetase encoded by the *S. cerevisiae* ACS2. Preferably, an acetyl-CoA synthetase with a high affinity for acetate has a Km for acetate of no more than 10, 5, 2, 1, 0.5, 0.2 or 0.1 mM, such e.g. the acetyl-CoA synthetase encoded by the *S. cerevisiae ACS*1 gene. More preferably a codon-optimised (see above) nucleotide sequence encoding the amino acid sequence of SEQ ID NO: 13 is overexpressed.

In another embodiment, the nucleotide sequence that is overexpressed encodes an acetyl-CoA synthetase with a high maximum rate ($v_{max}$). Use of an acetyl-CoA synthetase with a high maximum rate is preferred for condition under which there is a relatively high concentration of acetic acid in the culture medium, e.g. at least 2, 3, 4 or 5 g acetic acid/L culture medium. An acetyl-CoA synthetase with a high maximum rate is herein defined as an acetyl-CoA synthetase with a higher maximum rate than the acetyl-CoA synthetase encoded by the *S. cerevisiae* ACS1. Preferably, the acetyl-CoA synthetase with a high maximum rate is the acetyl-CoA synthetase encoded by the *S. cerevisiae* ACS2 gene. More preferably a codon-optimised (see above) nucleotide sequence encoding the amino acid sequence of SEQ ID NO: 14 is overexpressed.

For overexpression of the nucleotide sequence encoding the acetyl-CoA synthetase (to be overexpressed) is placed in an expression construct wherein it is operably linked to suitable expression regulatory regions/sequences to ensure overexpression of the acetyl-CoA synthetase enzyme upon transformation of the expression construct into the host cell of the invention (see above). Suitable promoters for (over) expression of the nucleotide sequence coding for the enzyme having acetyl-CoA synthetase activity include promoters that are preferably insensitive to catabolite (glucose) repression, that are active under anaerobic conditions and/or that preferably do not require xylose or arabinose for induction. Examples of such promoters are given above. In the cells of the invention, an acetyl-CoA synthetase to be overexpressed is overexpressed by at least a factor 1.1, 1.2, 1.5, 2, 5, 10 or 20 as compared to a strain which is genetically identical except for the genetic modification causing the overexpression. Preferably, the acetyl-CoA synthetase is overexpressed under anaerobic conditions by at least a factor 2, 5, 10, 20, 50, or 100 as compared to a strain which is genetically identical except for the genetic modification causing the overexpression. It is to be understood that these levels of overexpression may apply to the steady state level of the enzyme's activity (specific activity), the steady state level of the enzyme's protein as well as to the steady state level of the transcript coding for the enzyme.

In a further embodiment, the host cell of the invention further comprises a genetic modification that reduces specific $NAD^+$-dependent glycerol 3-phosphate dehydrogenase activity in the cell. Glycerol 3-phosphate dehydrogenase or glycerolphosphate dehydrogenase (EC 1.1.1.8) katalyses the reduction of dihydroxyacetone phosphate to sn-glycerol 3-phosphate while oxidising NADH to $NAD^+$. In the cells of the invention, the specific glycerolphosphate dehydrogenase activity is preferably reduced by at least a factor 0.8, 0.5, 0.3, 0.1, 0.05 or 0.01 as compared to a strain which is genetically identical except for the genetic modification causing the overexpression, preferably under anaerobic conditions.

Preferably, glycerolphosphate dehydrogenase activity is reduced in the host cell by one or more genetic modifications that reduce the expression of or inactivates a gene encoding an glycerolphosphate dehydrogenase. Preferably, the genetic modifications reduce or inactivate the expression of each endogenous copy of the gene encoding a specific glycerolphosphate dehydrogenase in the cell's genome. A given cell may comprise multiple copies of the gene encoding a specific glycerolphosphate dehydrogenase with one and the same amino acid sequence as a result of di-, poly- or aneu-ploidy. In such instances preferably the expression of each copy of the specific gene that encodes the glycerolphosphate dehydrogenase is reduced or inactivated. Alternatively, a cell may contain several different (iso)enzymes with glycerolphosphate dehydrogenase activity that differ in amino acid sequence and that are each encoded by a different gene. In such instances, in some embodiments of the invention it is preferred that only certain types of the isoenzymes are reduced or inactivated while other types remain unaffected (see below). Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of glycerolphosphate dehydrogenase activity in the host cell.

A preferred gene encoding a glycerolphosphate dehydrogenase whose activity is to be reduced or inactivated in the cell of the invention is the *S. cerevisiae* GPD2 gene as described by Eriksson et al. (1995, Mol. Microbiol. 17: 95-107), encoding the amino acid sequence of SEQ ID NO: 15 and orthologues thereof in other species. Therefore a gene encoding a glycerolphosphate dehydrogenase whose activity is to be reduced or inactivated in the cell of the invention preferably is a gene encoding a glycerolphosphate dehydrogenase having an amino acid sequence with at least 70, 75, 80, 85, 90, 95, 98 or 99% sequence identity to SEQ ID NO: 15.

In a preferred embodiment of the invention, the host cell of the invention comprises a functional high-osmolarity glycerol response pathway. Preferably therefore, only the activity of the gene(s) encoding a glycerolphosphate dehydrogenase having an amino acid sequence with at least 70% sequence identity to SEQ ID NO: 15 are reduced or inactivated, while at least one endogenous gene encoding a glycerolphosphate dehydrogenase having an amino acid sequence with at least 70, 75, 80, 85, 90, 95, 98 or 99% sequence identity to SEQ ID NO: 16 is functional. SEQ ID NO: 16 depicts the amino acid sequence encoded by the *S. cerevisiae* GPD1 gene as described by Albertyn et al. (1994, Mol. Cell. Biol. 14: 4135-4144), which has 69% amino acid identity with the *S. cerevisiae* GPD2 glycerolphosphate dehydrogenase. The *S. cerevisiae* GPD1 gene is the stress-induced glycerolphosphate dehydrogenase of *S. cerevisiae*, which is important for growth under osmotic stress as may occur under industrial fermentations conditions. Its expression is inter alia regulated by the high-osmolarity glycerol response pathway. It is therefore advantageous that a host cell of the invention has at least one functional copy of a endogenous gene encoding a glycerolphosphate dehydrogenase having an amino acid sequence with at least 70, 75, 80, 85, 90, 95, 98 or 99% sequence identity to SEQ ID NO: 16.

Notwithstanding the above, the inventors have now surprisingly found that inactivation of the *S. cerevisiae* GPD1 glycerolphosphate dehydrogenase has a more advantageous effect on the reduction of glycerol production and the increase of glycerol and acetate consumption as compared to inactivation of the *S. cerevisiae* GPD2 glycerolphosphate dehydrogenase. Therefore, in a more preferred embodiment, the host cell of the invention comprises a genetic modification that reduces or inactivates the expression of at least the gene(s) encoding a glycerolphosphate dehydrogenase having an amino acid sequence with at least 70, 75, 80, 85, 90, 95, 98 or 99% sequence identity to SEQ ID NO: 16 (GPD1).

In a further embodiment, the activity of all the genes in the host cell encoding a glycerolphosphate dehydrogenase is reduced or inactivated. In such cells preferably all copies of endogenous genes encoding a glycerolphosphate dehydrogenase having an amino acid sequence with at least 70, 75, 80, 85, 90, 95, 98 or 99% sequence identity to SEQ ID NO: 15 or 16 are inactivated or at least reduced in expression.

In another embodiment of the invention, the host cell is not a yeast cell comprising an exogenous gene coding for a enzyme with the ability to convert pyruvate and coenzyme-A into formate and acetyl-CoA. Preferably the host cell is not a yeast cell comprising a nucleotide sequence encoding a pyruvate formate lyase.

In yet another embodiment of the invention, the host cell is a host cell wherein the specific formate dehydrogenase activity is at least 81, 85, 90, 95, or 100% of the specific formate dehydrogenase activity in a strain of the host cell which is genetically identical except for a genetic modification selected from the group consisting of: a) (the introduction of) an exogenous gene coding for an enzyme with acetaldehyde dehydrogenase activity, which gene confers to the cell the ability to convert acetic acid into ethanol; b) (the introduction of) a bacterial gene coding for an enzyme with $NAD^+$-linked glycerol dehydrogenase activity; and c) any of the other genetic modifications described herein above. Thus, a preferred host cell of the invention is not a yeast cell comprising a genetic modification that reduces specific $NAD^+$-dependent formate dehydrogenase activity in the cell.

In a further preferred embodiment, the host cell of the invention has at least one of: a) the ability of isomerising xylose to xylulose; and, b) the ability to convert L-arabinose into D-xylulose 5-phosphate. For a) the cell preferably has a functional exogenous xylose isomerase gene, which gene confers to the cell the ability to isomerise xylose into xylulose. For b) the cell preferably has functional exogenous genes coding for a L-arabinose isomerase, a L-ribulokinase and a L-ribulose-5-phosphate 4-epimerase, which genes together confers to the cell the ability to isomerise convert L-arabinose into D-xylulose 5-phosphate.

Fungal host cells having the ability of isomerising xylose to xylulose as e.g. described in WO 03/0624430 and in WO 06/009434. The ability of isomerising xylose to xylulose is preferably conferred to the cell by transformation with a nucleic acid construct comprising a nucleotide sequence encoding a xylose isomerase. Preferably the cell thus acquires the ability to directly isomerise xylose into xylulose. More preferably the cell thus acquires the ability to grow aerobically and/or anaerobically on xylose as sole energy and/or carbon source though direct isomerisation of xylose into xylulose (and further metabolism of xylulose). It is herein understood that the direct isomerisation of xylose into xylulose occurs in a single reaction catalysed by a xylose isomerase, as opposed to the two step conversion of xylose into xylulose via a xylitol intermediate as catalysed by xylose reductase and xylitol dehydrogenase, respectively.

Several xylose isomerases (and their amino acid and coding nucleotide sequences) that may be successfully used to confer to the cell of the invention the ability to directly isomerise xylose into xylulose have been described in the art. These include the xylose isomerases of *Piromyces* sp. and of other anaerobic fungi that belongs to the families Neocallimastix, Caecomyces, *Piromyces* or Ruminomyces (WO 03/0624430), *Cyllamyces aberensis* (US 20060234364), *Orpinomyces* (Madhavan et al., 2008, DOI 10.1007/s00253-008-1794-6), the xylose isomerase of the bacterial genus *Bacteroides*, including e.g. *B. thetaiotaomicron* (WO 06/009434), *B. fragilis*, and *B. uniformis* (WO 09/109633), the xylose isomerase of the anaerobic bacterium *Clostridium phytofermentans* (Brat et al., 2009, Appl. Environ. Microbiol. 75: 2304-2311), and the xylose isomerases of *Clostridium difficile, Ciona intestinales* and *Fusobacterium mortiferum.*

Fungal host cells having the ability to convert L-arabinose into D-xylulose 5-phosphate as e.g. described in Wisselink et al. (2007, AEM Accepts, published online ahead of print on 1 Jun. 2007; Appl. Environ. Microbiol. doi:10.1128/AEM.00177-07) and in EP 1 499 708. The ability of to converting L-arabinose into D-xylulose 5-phosphate is preferably conferred to the cell by transformation with a nucleic acid construct(s) comprising nucleotide sequences encoding a) an arabinose isomerase; b) a ribulokinase, preferably a L-ribulokinase a xylose isomerase; and c) a ribulose-5-P-4-epimerase, preferably a L-ribulose-5-P-4-epimerase. Preferably, in the cells of the invention, the ability to convert L-arabinose into D-xylulose 5-phosphate is the ability to convert L-arabinose into D-xylulose 5-phosphate through the subsequent reactions of 1) isomerisation of arabinose into ribulose; 2) phosphorylation of ribulose to ribulose 5-phosphate; and, 3) epimerisation of ribulose 5-phosphate into D-xylulose 5-phosphate. Suitable nucleotide sequences encoding arabinose isomerases, a ribulokinases and ribulose-5-P-4-epimerases may be obtained from *Bacillus subtilis, Escherichia coli* (see e.g. EP 1 499 708), Lactobacilli, e.g. *Lactobacillus plantarum* (see e.g. Wisselink et al. supra), or species of *Clavibacter, Arthrobacter* and *Gramella*, of which preferably *Clavibacter michiganensis, Arthrobacter aurescens* and *Gramella forsetii* (see WO2009/011591).

The transformed host cell of the invention further preferably comprises xylulose kinase activity so that xylulose isomerised from xylose may be metabolised to pyruvate. Preferably, the cell contains endogenous xylulose kinase activity. More preferably, a cell of the invention comprises a genetic modification that increases the specific xylulose kinase activity. Preferably the genetic modification causes overexpression of a xylulose kinase, e.g. by overexpression of a nucleotide sequence encoding a xylulose kinase. The gene encoding the xylulose kinase may be endogenous to the cell or may be a xylulose kinase that is heterologous to the cell. A nucleotide sequence that may be used for overexpression of xylulose kinase in the cells of the invention is e.g. the xylulose kinase gene from *S. cerevisiae* (XKS1) as described by Deng and Ho (1990, Appl. Biochem. Biotechnol. 24-25: 193-199). Another preferred xylulose kinase is a xylose kinase that is related to the xylulose kinase from *Piromyces* (xylB; see WO 03/0624430). This *Piromyces* xylulose kinase is actually more related to prokaryotic kinase than to all of the known eukaryotic kinases such as the yeast kinase. The eukaryotic xylulose kinases have been indicated as non-specific sugar kinases, which have a broad substrate range that includes xylulose. In contrast, the prokaryotic xylulose kinases, to which the *Piromyces* kinase is most closely related, have been indicated to be more specific kinases for xylulose, i.e. having a narrower substrate range. In the cells of the invention, a xylulose kinase to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

A cell of the invention further preferably comprises a genetic modification that increases the flux of the pentose phosphate pathway as described in WO 06/009434. In particular, the genetic modification causes an increased flux of the non-oxidative part pentose phosphate pathway. A genetic modification that causes an increased flux of the non-oxidative part of the pentose phosphate pathway is herein understood to mean a modification that increases the flux by at least a factor 1.1, 1.2, 1.5, 2, 5, 10 or 20 as compared to the flux in a strain which is genetically identical except for the genetic modification causing the increased flux. The flux of the non-oxidative part of the pentose phosphate pathway may be measured as described in WO 06/009434.

Genetic modifications that increase the flux of the pentose phosphate pathway may be introduced in the cells of the invention in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred cell of the invention, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate 3-epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate 3-epimerase; or at least the enzymes ribulose-5-phosphate isomerase and transketolase; or at least the enzymes ribulose-5-phosphate isomerase and transaldolase; or at least the enzymes ribulose-5-phosphate 3-epimerase and transketolase; or at least the enzymes ribulose-5-phosphate 3-epimerase and transaldolase; or at least the enzymes transketolase and transaldolase; or at least the enzymes ribulose-5-phosphate 3-epimerase, transketolase and transaldolase; or at least the enzymes ribulose-5-phosphate isomerase, transketolase and transaldolase; or at least the enzymes ribulose-5-phosphate isomerase, ribulose-5-phosphate 3-epimerase, and transaldolase; or at least the enzymes ribulose-5-phosphate isomerase, ribulose-5-phosphate 3-epimerase, and transketolase. In one embodiment of the invention each of the enzymes ribulose-5-phosphate isomerase, ribulose-5-phosphate 3-epimerase, transketolase and transaldolase are overexpressed in the cell of the invention. Preferred is a cell in which the genetic modification comprises at least overexpression of the enzyme transaldolase. More preferred is a cell in which the genetic modification comprises at least overexpression of both the enzymes transketolase and transaldolase as such a host cell is already capable of anaerobic growth on xylose. In fact, under some conditions we have found that cells overexpressing only the transketolase and the transaldolase already have the same anaerobic growth rate on xylose as do cells that overexpress all four of the enzymes, i.e. the ribulose-5-phosphate isomerase, ribulose-5-phosphate 3-epimerase, transketolase and transaldolase. Moreover, cells of the invention overexpressing both of the enzymes ribulose-5-phosphate isomerase and ribulose-5-phosphate 3-epimerase are preferred over cells overexpressing only the isomerase or only the 3-epimerase as overexpression of only one of these enzymes may produce metabolic imbalances.

There are various means available in the art for overexpression of enzymes in the cells of the invention. In particular, an enzyme may be overexpressed by increasing the copy number of the gene coding for the enzyme in the cell, e.g. by integrating additional copies of the gene in the cell's genome, by expressing the gene from an episomal multicopy expression vector or by introducing a episomal expression vector that comprises multiple copies of the gene. The coding sequence used for overexpression of the enzymes preferably is homologous to the host cell of the invention. However, coding sequences that are heterologous to the host cell of the invention may likewise be applied.

Alternatively overexpression of enzymes in the cells of the invention may be achieved by using a promoter that is not native to the sequence coding for the enzyme to be overexpressed, i.e. a promoter that is heterologous to the coding sequence to which it is operably linked Although the promoter preferably is heterologous to the coding sequence to which it is operably linked, it is also preferred that the promoter is homologous, i.e. endogenous to the cell of the invention. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence, preferably under conditions where xylose or xylose and glucose are available as carbon sources, more preferably as major carbon sources (i.e. more than 50% of the available carbon source consists of xylose or xylose and glucose), most preferably as sole carbon sources.

A further preferred cell of the invention comprises a genetic modification that reduces unspecific aldose reductase activity in the cell. Preferably, unspecific aldose reductase activity is reduced in the host cell by one or more genetic modifications that reduce the expression of or inactivates a gene encoding an unspecific aldose reductase. Preferably, the genetic modifications reduce or inactivate the expression of each endogenous copy of a gene encoding an unspecific aldose reductase that is capable of reducing an aldopentose, including, xylose, xylulose and arabinose, in the cell's genome. A given cell may comprise multiple copies of genes encoding unspecific aldose reductases as a result of di-, poly- or aneu-ploidy, and/or a cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell. A nucleotide sequence encoding an aldose reductase whose activity is to be reduced in the cell of the invention and amino acid sequences of such aldose reductases are described in WO 06/009434 and include e.g. the (unspecific) aldose reductase genes of *S. cerevisiae* GRE3 gene (Träff et al., 2001, Appl. Environm. Microbiol. 67: 5668-5674) and orthologues thereof in other species.

A further preferred transformed host cell according to the invention may comprises further genetic modifications that result in one or more of the characteristics selected from the group consisting of (a) increased transport of xylose and/or arabinose into the cell; (b) decreased sensitivity to catabolite repression; (c) increased tolerance to ethanol, osmolarity or organic acids; and, (d) reduced production of by-products. By-products are understood to mean carbon-containing molecules other than the desired fermentation product and include e.g. xylitol, arabinitol, glycerol and/or acetic acid. Any genetic modification described herein may be introduced by classical mutagenesis and screening and/or selection for the desired mutant, or simply by screening and/or selection for the spontaneous mutants with the desired characteristics. Alternatively, the genetic modifications may consist of overexpression of endogenous genes and/or the inactivation of endogenous genes. Genes the overexpression of which is desired for increased transport of arabinose and/or xylose into the cell are preferably chosen form genes encoding a hexose or pentose transporter. In *S. cerevisiae* and other yeasts these genes include HXT1, HXT2, HXT4, HXT5, HXT7 and GAL2, of which HXT7, HXT5 and GAL2 are most preferred (see Sedlack and Ho, Yeast 2004; 21: 671-684). Another preferred transporter for expression in yeast is the glucose transporter encoded by the *P. stipitis* SUT1 gene (Katahira et al., 2008, Enzyme Microb. Technol. 43: 115-119). Similarly orthologues of these transporter genes in other species may be overexpressed. Other genes that may be overexpressed in the cells of the invention include genes coding for glycolytic enzymes and/or ethanologenic enzymes such as alcohol dehydrogenases. Preferred endogenous genes for inactivation include hexose kinase genes e.g. the *S. cerevisiae* HXK2 gene (see Diderich et al., 2001, Appl. Environ. Microbiol. 67: 1587-1593); the *S. cerevisiae* MIG1 or MIG2 genes; genes coding for enzymes involved in glycerol metabolism such as the *S. cerevisiae* glycerol-phosphate dehydrogenase 1 and/or 2 genes; or (hybridising) orthologues of these genes in other species. Other preferred further modifications of host cells for xylose fermentation are described in van Maris et al. (2006, Antonie van Leeuwenhoek 90:391-418), WO2006/009434, WO2005/023998, WO2005/111214, and WO2005/091733. Any of the genetic modifications of the cells of the invention as described herein are, in as far as possible, preferably introduced or modified by self cloning genetic modification.

A preferred host cell according to the invention has the ability to grow on at least one of xylose and arabinose as carbon/energy source, preferably as sole carbon/energy source, and preferably under anaerobic conditions, i.e. conditions as defined herein below for anaerobic fermentation process. Preferably, when grown on xylose as carbon/energy source the host cell produces essentially no xylitol, e.g. the xylitol produced is below the detection limit or e.g. less than 5, 2, 1, 0.5, or 0.3% of the carbon consumed on a molar basis. Preferably, when grown on arabinose as carbon/energy source, the cell produces essentially no arabinitol, e.g. the arabinitol produced is below the detection limit or e.g. less than 5, 2, 1, 0.5, or 0.3% of the carbon consumed on a molar basis.

A preferred host cell of the invention has the ability to grow on a combination of: a) at least one of a hexose and a pentose; b) acetic acid; and c) glycerol at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. Therefore, preferably the host cell has the ability to grow on at least one of xylose and arabinose as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. More preferably, the host cell has the ability to grow on a mixture of a hexose (e.g. glucose) and at least one of xylose and arabinose (in a 1:1 weight ratio) as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions.

In a one aspect, the invention relates to the use of a yeast cell according to the invention for the preparation of a fermentation product selected from the group consisting of ethanol, lactic acid, 3-hydroxy-propionic acid, acrylic acid, 1,3-propane-diol, butanols and isoprenoid-derived products.

In another aspect the invention relates to a process for producing a fermentation product selected from the group consisting of ethanol, lactic acid, 3-hydroxy-propionic acid, acrylic acid, 1,3-propane-diol, butanols (1-butanol, 2-butanol, isobutanol) and isoprenoid-derived products. The process preferably comprises the step of: a) fermenting a medium with a yeast cell, whereby the medium contains or is fed with: a) a source of at least one of a hexose and a pentose; b) a source of acetic acid; and, c) a source of glycerol and whereby the yeast cell ferments acetic acid, glycerol and at least one of the hexose and pentose to ethanol. The yeast cell preferably is a (host) cell as herein defined above. The process preferably comprise a further step wherein the fermentation product is recovered. The process may be a batch process, a fed-batch process or a continuous process as are well known in the art. In the process of the invention, the source of glycerol may be a any carbon source that has a more reduced state than glucose. A carbon source having a more reduced state than glucose is understood as a carbon source of which the average reduction state per C-mol (of the compounds therein) is higher than the reduction state per C-mol of glucose. Examples of carbon sources having a more reduced state than glucose include e.g. alkanols such as propanol and butanol; polyols such as 1,3-propane-diol, butandiol, glycerol, mannitol and xylitol.

In a preferred process the source of hexose comprises or consists of glucose. Preferably the source pentose comprises or consists of at least one of xylose and arabinose. Preferably, the medium fermented by the cells of the invention comprises or is fed with (fractions of) hydrolysed biomass comprising at least one at least one of a hexose and a pentose such as glucose, xylose and/or arabinose. The (fractions of) hydrolysed biomass comprising the hexoses and pentose will usually also comprise acetic acid (or a salt thereof). An example of hydrolysed biomass to be fermented in the processes of the invention is e.g. hydrolysed lignocellulosic biomass. Lignocellulosic biomass is herein understood as plant biomass that is composed of cellulose, hemicellulose, and lignin. The carbohydrate polymers (cellulose and hemicelluloses) are tightly bound to the lignin. Examples of lignocellulosic biomass to be hydrolysed for use in the present invention include agricultural residues (including corn stover and sugarcane bagasse), wood residues (including sawmill and paper mill discards and (municipal) paper waste. Methods for hydrolysis of biomass such as lignocelluloses are known in the art per se and include e.g. acids, such as sulphuric acid and enzymes such as cellulases and hemicellulases.

In the process of the invention, the sources of xylose, glucose and arabinose may be xylose, glucose and arabinose as such (i.e. as monomeric sugars) or they may be in the form of any carbohydrate oligo- or polymer comprising xylose, glucose and/or arabinose units, such as e.g. lignocellulose, arabinans, xylans, cellulose, starch and the like. For release of xylose, glucose and/or arabinose units from such carbohydrates, appropriate carbohydrases (such as arabinases, xylanases, glucanases, amylases, cellulases, glucanases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases preferably during the fermentation. This, in turn, will prevent repression of systems required for metabolism and transport of non-glucose sugars such as xylose and arabinose. In a preferred process the modified host cell ferments both the glucose and at least one of xylose and arabinose, preferably simultaneously in which case preferably a modified host cell is used which is insensitive to glucose repression to prevent diauxic growth. In addition to a source of at least one of xylose and arabinose (and glucose) as carbon source, the fermentation medium will further comprise the appropriate ingredient required for growth of the modified host cell. Compositions of fermentation media for growth of eukaryotic microorganisms such as yeasts are well known in the art.

In the process of the invention, the medium further preferably comprises and/or is fed a source of glycerol. Glycerol for use in the process of the present invention may advantageously be glycerol that is generated as a by-product in biodiesel production from transesterification reactions using vegetable oils or animal fats and an alcohol.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, as well as non-ethanol fermentation products such as lactic acid, 3-hydroxy-propionic acid, acrylic acid, 1,3-propane-diol, butanols (1-butanol, 2-butanol, isobutanol) isoprenoid-derived products. Anaerobic processes of the invention are preferred over aerobic processes because anaerobic processes do not require investments and energy for aeration and in addition, anaerobic processes produce higher product yields than aerobic processes.

Alternatively, the fermentation process of the invention may be run under aerobic oxygen-limited conditions. Preferably, in an aerobic process under oxygen-limited conditions, the rate of oxygen consumption is at least 5.5, more preferably at least 6 and even more preferably at least 7 mmol/L/h. In a preferred aerobic oxygen-limited fermentation process of the invention, the yeast cell of the invention consumes less than 30, 20, 18, 15, 12, 10, 8 or 5% of the amount of oxygen on a C-molar basis related to the carbon source consumed during the conversion of the carbon source into the fermentation product. The conversion coefficient of oxygen consumed over substrate utilised on a C-molar basis ($C_{OS}$) is herein understood to mean mol $O_2$ used per C-mol carbon source consumed. Thus, a process of the invention can be carried out under strict anaerobic conditions (i.e. $C_{OS}$=0.0), or the process of the invention can be carried out under aerobic, preferably oxygen-limited conditions wherein the $C_{OS}$ is preferably less than 0.3, 0.2, 0.18, 0.15, 0.12, 0.1, 0.08, or 0.05.

The fermentation process is preferably run at a temperature that is optimal for the modified cells of the invention. Thus, for most yeasts cells, the fermentation process is performed at a temperature which is less than 42° C., preferably less than 38° C. For yeast cells, the fermentation process is preferably performed at a temperature which is lower than 35, 33, 30 or 28° C. and at a temperature which is higher than 20, 22, or 25° C.

A preferred fermentation process according to the invention is a process for the production of ethanol, whereby the process comprises the step of fermenting a medium with a yeast cell, whereby the medium contains or is fed with: a) a source of at least one of a hexose and a pentose; b) a source of acetic acid; and, c) a source of glycerol, whereby the yeast cell ferments acetic acid, glycerol and at least one of the hexose and pentose to ethanol, and optionally, b) recovery of the ethanol. The fermentation medium may further be performed as described above. In the process the volumetric ethanol productivity is preferably at least 0.5, 1.0, 1.5, 2.0, 2.5, 3.0, 5.0 or 10.0 g ethanol per liter per hour. The ethanol yield on xylose and/or glucose and/or arabinose and/or acetate and/or glycerol in the process preferably is at least 50, 60, 70, 80, 90, 95 or 98%. The ethanol yield is herein defined as a percentage of the theoretical maximum yield, which, for xylose, glucose and arabinose is 0.51 g. ethanol per g. xylose, glucose or arabinose. For glycerol the theoretical maximum yield is 0.50 g. ethanol per g. glycerol and for acetic acid the theoretical maximum yield is 0.77 g. ethanol per g. acetic acid.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

1. Enzyme Activity Assays

Figure 1:
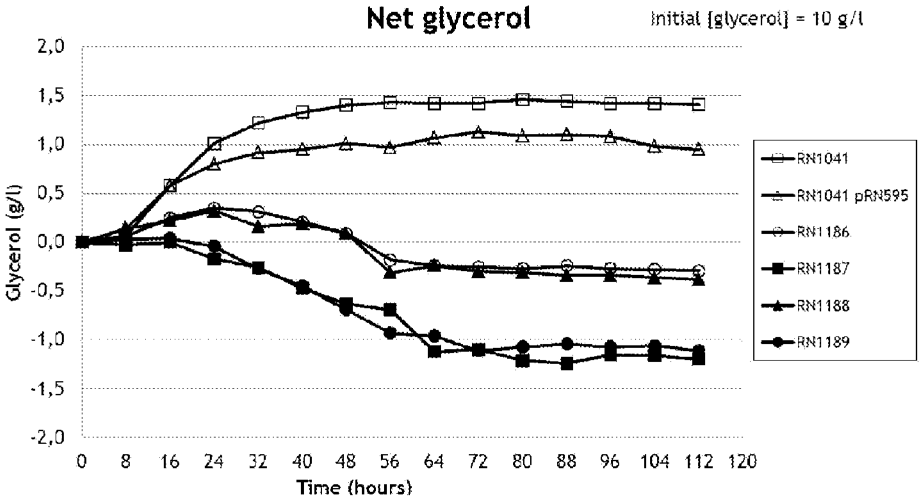
FIG. 1. The evolution of the net glycerol levels (g/l) (i.e. production minus consumption) over time (hours) is shown for *S. cerevisiae* strains RN1041, RN1041+pRN595, RN1186, RN1187, RN1188 and RN1189.

Cell extracts for activity assays were prepared from exponentially growing aerobic or anaerobic batch cultures and analysed for protein content as described by Abbot et al., (2009, Appl. Environ. Microbiol. 75: 2320-2325).

$NAD^+$-dependent acetaldehyde dehydrogenase (EC 1.2.1.10) activity was measured at 30° C. by monitoring the oxidation of NADH at 340 mm. The reaction mixture (total volume 1 ml) contained 50 mM potassium phosphate buffer (pH 7.5), 0.15 mM NADH and cell extract. The reaction was started by addition of 0.5 mM acetyl-Coenzyme A.

For glycerol 3-phosphate dehydrogenase (EC 1.1.1.8) activity determination, cell extracts were prepared as described above except that the phosphate buffer was replaced by triethanolamine buffer (10 mM, pH 5). Glycerol-3-phosphate dehydrogenase activities were assayed in cell extracts at 30° C. as described previously (Blomberg and Adler, 1989, J. Bacteriol. 171: 1087-1092.9). Reaction rates were proportional to the amounts of cell extract added.

Acetyl-CoA synthase (EC 6.2.1.1) activity was measured as described by Frenkel and Kitchens (1977, J. Biol. Chem. 252: 504-507) which is a modification of the method of Webster (Webster, 1969, Methods Enzymol. 13: 375-381). NADH formation measured is spectrophotometrically when the acetyl-CoA produced is coupled with citrate synthase and malate dehydrogenase reactions. The assay system contained 100 mM Tris-Cl (pH 7.6), 10 mM $MgCl_2$, 6 mM ATP, 5 mM malate, 1 mM $NAD^+$, 0.1 mM NADH, 2.5 mM dithiothreitol or 2-mercaptoethanol, 0.2 mM coenzyme A, 25 ng citrate synthase (80 units/mg), 20 ng malate dehydrogenase (1000 units/mg), and 10 mM acetate and the reaction was measured rate was measured at 340 nm and calculated from the extinction coefficient of NADH ($6.22 \times 10^6$ $cm^2$/mol).

The activity of glycerol dehydrogenase and dihydroxyacetone kinase are measured at 30° C. in cell extracts, essentially as previously described (Gonzalez et al., 2008, Metab. Eng. 10, 234-245). Enzyme activities of glycerol dehydrogenase and dihydroxyacetone kinase are reported as μmoles of substrate/min/mg of cell protein.

2. Strain Construction

All modifications start with the xylose and arabinose fermenting strain RN1008 his⁻. RN1008 his⁻, also referred to herein as RN1041, is a CEN.PK-based arabinose and xylose fermenting strain) with the genotype:

Mat a, ura3-52, leu2-112, his3::loxP, gre3::loxP, loxP-Ptpi::TAL1, loxP-Ptpi::RKI1, loxP-Ptpi-TKL1, loxP-Ptpi-RPE1, delta::-LEU2, delta::Padh1XKS1Tcyc1-URA3-Ptpi-xylA-Tcyc1, delta::LEU2-AAAaraABD.

Mat a=mating type a ura3-52, leu2-112, his3::loxP mutations in the genes ura3, leu2 and his3, the ura3 is complemented by the xylA-XKS overexpression construct, leu2 is complemented by the AraABD overexpression construct. his3 could be used for selection of additional plasmids, RN1041 needs histidine in the medium for growth.

gre3::loxP=deletion of the gre3 gene encoding xylose reductase, loxP site is left after marker removal.

loxP-Ptpi . . . =overexpression of het pentose phosphate pathway, loxP site upstream of constitutive promoter is left after marker removal delta::=integration of the construct after recombination on the long terminal repeats of the Ty1 reterotransposon.

AAAaraABD=codon optimized *arthrobacter aurescens* araA, araB and araD genes (see WO2009/011591)

Deletion Constructs for GPD1 and GPD2

The deletion of GPD1 in RN1041 produces strain RN1197. The deletion of GPD2 in RN1041 produces strain RN1198. In this strain subsequently gpd1 is deleted to produce strain RN1199. In these strains plasmids were introduced for overexpression of the ACS genes (RN1200 to RN1207, Table 4) and further genes as indicated in Table 4.

gpd1::hphMX

Primers gpd1uf, gpd1ur, gpd1df and gpd1dr are used for amplification of genomic sequences fragments upstream and downstream of the GPD1 gene for its inactivation. Both the up- and downstream GPD1 fragments are cloned into a topo blunt vector (InVitrogen) to yield pGPD1up and pGPD1down, respectively.

```
                                    (SEQ ID NO: 41)
gpd1uf: AAGCTTGGTACCCGCCTTGCTTCTCTCCCC

                                    (SEQ ID NO: 42)
gpd1ur: TCTAGACCAGCATTCAAGTGGCCGGA

                                    (SEQ ID NO: 43)
gpd1df: CGTACGAGTTGTTGAATGGCCAATCCGCT

                                    (SEQ ID NO: 44)
gpd1dr: CCATGGTACCGAGTGGTGTTGTAACCACCCT

                                    (SEQ ID NO: 45)
gpd1cf: ACCAATACGTAAACGGGGCG

                                    (SEQ ID NO: 46)
gpd1cr: AATACACCCATACATACGGACGC
```

Plasmid pRN593 (SEQ ID NO: 40) is constructed by ligation of the fragment cut with HindIII and XbaI from pGPD1up to the hphMX fragment cut with SpeI and BsrGI (plasmid collection C5YeastCompany) and the fragment cut with BsiWI and NcoI from pGPD1down into the HindIII and NcoI cut topo T/A vector (Invitrogen). Plasmid pRN593 is cut with KpnI to obtain deletion fragment for disrupting the genomic copy (SEQ ID NO: 17). The mixture of linear fragments is used for transformation of yeast. Transformants are selected for hygromycin resistance. Correct integration results in deletion of the GPD1 open reading frame. The integration is PCR verified with the primers gpd1cf and gpd1cr.

gpd2::natMX

Primers GPD2uf, GPD2ur, GPD2df and GPD2dr are used for amplification of genomic sequences fragments upstream and downstream of the GPD2 gene for its inactivation. A 407 bp upstream PCR fragment with an AflII site at the 3'-end (derived from the GPD2 sequence) and a BglII site at the 5'-end (for isolation of the deletion construct) is amplified using GPD2uf, GPD2ur and cloned in pCR2.1 (topo T/A, Invitrogen).

```
                                    (SEQ ID NO: 32)
GPD2uf: GGTACCAGATCTTTTGCGGCGAGGTGCCG

                                    (SEQ ID NO: 33)
GPD2ur: TCTAGACTTAAGGAATGTGTATCTTGTTAATCTTCTGACAGC
```

A 417 bp downstream PCR fragment with a XhoI site at the 5'-end and a BglII site at the 3'-end is amplified using GPD2df and GPD2dr.

```
                                    (SEQ ID NO: 34)
GPD2df: CTCGAGATAGTCTACAACAACGTCCGCA

                                    (SEQ ID NO: 35)
GPD2dr: CCATGGAGATCTGCAGTGAAAAAGCTCGAAGAAACAGCT
```

For the final construction the plasmid containing the upstream fragment is cut with AflII and Kpn, the downstream fragment is cut with XhoI en NcoI and the natMX marker (plasmid collection Royal Nedalco) is cut with AflII en XhoI and the fragments are ligated to produce plasmid pRN594 (SEQ ID NO: 36). pRN594 is cut with BglII prior to yeast transformation. Transformants are selected for nourseotricin resistance. Correct integration is verified by PCR.

Cloning Method for Overexpression of the *Saccharomyces cerevisiae* ACS1 and ACS2 Genes The ACS1 open reading frame is PCR amplified with the primers acs1f and acs1r.

```
acs1f:
                                    (SEQ ID NO: 47)
 TTAAGCTTAAAATGTCGCCCTCTGCCGT

acs1r:
                                    (SEQ ID NO: 48)
AAGCGCGCTACAACTTGACCGAATCAATTAGATGTCTAACAATGCCAGGG
```

This PCR fragment is cut with the restriction enzymes HindIII and BssHII and ligated to the SalI and HindIII cut TEF1 promoter fragment (collection C5YeastCompany) and the BssHII and BsiWI cut ADH1 terminator fragment (collection C5YeastCompany). This combined fragment is PCRed with promoter and terminator specific primers and cloned into the topo Blunt vector (InVitrogen) to give pACS1.

The ACS2 open reading frame is PCR amplified with the primers acs2f and acs2r.

acs2f:

(SEQ ID NO: 49)
AACTGCAGAAAATGACAATCAAGGAACATAAAGTAGTTTATGAAGCTCA acs2r:

(SEQ ID NO: 50)
ACGTCGACTATTTCTTTTTTTGAGAGAAAAATTGGTTCTCTACAGCAGA

This PCR fragment is cut with the restriction enzymes PstI and SalI and ligated to the SpeI and PstI cut PGK1 promoter fragment (collection C5YeastCompany) and the XhoI and BsiWI cut PGI1 terminator fragment (collection C5YeastCompany). This combined fragment is PCRed with promoter and terminator specific primers and cloned into the topo Blunt vector (InVitrogen) to give plasmid pACS2.

The ACS1 overexpression construct is cut from pACS1 with the restriction enzymes SalI and BsiWI, the ACS2 overexpression construct is cut from pACS2 with the restriction enzymes SpeI and BsiWI, the KanMX marker is cut with BspEI and XbaI (plasmid collection C5YeastCompany). These fragments are ligated to the plasmid pRS306+2mu ORI (plasmid collection C5Yeast company) cut with BspEI and XhoI to give the final plasmid pRN753 (SEQ ID NO: 51). This plasmid is used to transform yeast strains as indicated in Table 4 and transformants are selected on G418 resistance. Overexpression is verified by qPCR. An alternative plasmid that may be used for overexpression of ACS1 and ACS2 is pRN500 (SEQ ID NO: 20).

Expression of *E. coli* adhE, *E. histolytica* ADH2 or *E. coli* mphF

The PGK1 promoter (SpeI-PstI) and the ADH1 terminator sequence (AflII-NotI) are added to the codon optimized synthetic fragments and cloned into pRS303 with 2μ ori cut with SpeI and NotI and the expression construct is cloned in this vector. Expression is qPRC verified. Codon optimized sequences for *E. coli* mphF (SEQ ID NO: 2), *E. coli* adhE (SEQ ID NO: 4) and *E. histolytica* ADH2 (SEQ ID NO: 6) are as indicated in the sequence listing.

For expression of the *E. coli* mhpF gene, a yeast PGK1 promoter fragment (SpeI-PstI) and an ADH1 terminator fragment (AflII-NotI) (both from the Nedalco plasmid collection) were ligated onto the codon-optimized synthetic fragment encoding the *E. coli* mhpF (SEQ ID NO: 2). pRS 303 with 2μ ori (=pRN347, Royal Nedalco plasmid collection) was cut with SpeI and NotI and the mhpF expression construct was cloned into this vector to produce pRN558 (SEQ ID NO: 29).

For expression of the *E. coli* adhE gene, a codon optimized synthetic fragment encoding the *E. coli* adhE (SEQ ID NO: 4) is cut with XbaI and AflII and ligated into pRN558 cut with XbaI and AflII (replacing the *E. coli* mhpF gene in pRN558) to produce pRN595 (SEQ ID NO: 30).

For expression of the *Entamoebe histolytica* adh2, a codon optimized synthetic fragment encoding the *E. histolytica* adh2 (SEQ ID NO: 6) is cut with XbaI and AflII and ligated into pRN558 cut with XbaI and AflII (replacing the *E. coli* mhpF gene in pRN558) to produce pRN596 (SEQ ID NO: 31). pRN595 is used for further construction of pRN957 and pRN977 (see below). It is clear that pRN558 and pRN596 can be used in the same way, thereby replacing expression of *E. coli* adhE with *E. coli* mhpF or *E. histolytica* adh2, respectively.

Expression of *E. coli* gldA

The construct for expression in yeast of the *E. coli* gldA was made by ligating a yeast ACT1 promoter fragment (cut with the restriction enzymes SpeI and PstI), a synthetic ORF (SEQ ID NO: 21), encoding the *E. coli* gldA, (cut with PstI en BssHII) and a yeast CYC1 terminator fragment (cut with BssHII and BsiWI) together into pCRII blunt (Invitrogen) to yield pRNgldA (SEQ ID NO: 28).

DAK1 Overexpression

PCR is performed on genomic DNA of *S. cerevisiae* with primers introducing a XbaI site 5' of the ATG and a SalI site 3' of the TAA to produce the fragment of SEQ ID NO: 22. A DNA fragment comprising the *S. cerevisiae* TPI1 promoter is ligated upstream of the DAK1 ORF and DNA fragment comprising the *S. cerevisiae* PGI1 terminator fragment is ligated downstream of the DAK1 ORF to produce pRNDAK (SEQ ID NO: 38).

Expression of *C. freundii* dhaK

The construct for expression in yeast of the *Citrobacter freundii* dhaK was made by ligating the yeast TPI1 promoter fragment (cut with the restriction enzymes XhoI and XbaI), a synthetic ORF (SEQ ID NO: 26), encoding the *C. freundii* dhaK, (cut with XbaI and SalI) and a yeast PGI1 terminator fragment (cut with XhoI and BsiWI) together into pCRII blunt (Invitrogen) to yield pRNdhaK (SEQ ID NO: 27).

GUP1 Overexpression

PCR is performed on genomic DNA of *S. cerevisiae* with primers introducing a HindIII site 5' of the ATG and a BamHI site 3' of the TAA to produce the fragment of SEQ ID NO: 23. A DNA fragment comprising the *S. cerevisiae* TDH3 promoter is ligated upstream of the GUP1 ORF and DNA fragment comprising the *S. cerevisiae* CYC1 terminator fragment is ligated downstream of the GUP1 ORF.

FPS1 Overexpression

PCR is performed on genomic DNA of *S. cerevisiae* with primers introducing a NsiI site 5' of the ATG and a BamHI site 3' of the TAA to produce the fragment of SEQ ID NO: 24. A DNA fragment comprising the *S. cerevisiae* ADH1 (medium) promoter is ligated upstream of the FSP1 ORF and DNA fragment comprising the *S. cerevisiae* CYC1 terminator fragment is ligated downstream of the FSP1 ORF.

Construction of pRN347 and Yeast Strain RN1151 pRN347 is constructed by cloning the 2μ origin of replication (that was PCR-amplified from pYES2) in pRS303 (with HIS3 gene for complementation). RN1041 is transformed with the plasmid pRN347 to produce strain RN1151.

Strains Expressing *E. coli* gldA and *C. freundii* dhaK or Overexpressing DAK1

For construction of pRN957, the *E. coli* gldA expression construct is cut from plasmid pRNgldA with the restriction enzymes SpeI and BsiWI. The *C. freundii* dhaK expression construct is cut from plasmid pRNdhaK with the restriction enzymes BsiWI and XhoI. These fragments are ligated into plasmid pRN595 cut with the restriction enzymes SpeI and SalI to yield pRN957 (SEQ ID NO: 37).

For construction of pRN977, the *E. coli* gldA expression construct is cut from plasmid pRNgldA with the restriction enzymes SpeI and BsiWI. The DAK1 expression construct is cut from the plasmid pRNDAK with the restriction enzymes BsiWI and XhoI. These fragments are ligated to plasmid pRN595 cut with the restriction enzymes SpeI and SalI to yield pRN977 (SEQ ID NO: 39).

Plasmids pRN957 and pRN977 are used to transform RN1041, RN1197, RN1198 and RN1199 to yield yeast strains as indicated in Table 4.

TABLES 4A and B

Overview of constructed strains

Table 4A

| Strain marker | ACS1 kanMX | ACS2 kanMX | GPD1 hphMX | GPD2 natMX | adhE HIS3 | DAK1 HIS3 | Cf dhaK HIS3 | Ec gldA HIS3 | HIS3 |
|---|---|---|---|---|---|---|---|---|---|
| RN1041 | wt | wt | wt | wt | absent | wt | absent | absent | del |
| RN1151 | wt | wt | wt | wt | absent | wt | absent | absent | wt |
| RN1197 | wt | wt | del | wt | absent | wt | absent | absent | wt |
| RN1198 | wt | wt | wt | del | absent | wt | absent | absent | wt |
| RN1199 | wt | wt | del | del | absent | wt | absent | absent | wt |
| RN1200 | up | up | wt | wt | expression | up | absent | expression | |
| RN1201 | up | up | wt | wt | expression | wt | expression | expression | |
| RN1202 | up | up | del | wt | expression | up | absent | expression | |
| RN1203 | up | up | del | wt | expression | wt | expression | expression | |
| RN1204 | up | up | wt | del | expression | up | absent | expression | |
| RN1205 | up | up | wt | del | expression | wt | expression | expression | |
| RN1206 | up | up | del | del | expression | up | absent | expression | |
| RN1207 | up | up | del | del | expression | wt | expression | expression | |

Table 4B

| | ACS1/2 | gpd1Δ | gpd2Δ | adhE, gldA, DAK1 | adhE, gldA, dhaK | HIS3 |
|---|---|---|---|---|---|---|
| RN1041 | | | | | | |
| RN1151 | | | | | | pRN347 |
| RN1197 | | pRN593 | | | | pRN347 |
| RN1198 | | | | | | pRN347 |
| RN1199 | | pRN593 | pRN594 | | | pRN347 |
| RN1200 | pRN753 | | | pRN957 | | |
| RN1201 | pRN753 | | | | pRN977 | |
| RN1202 | pRN753 | pRN593 | | pRN957 | | |
| RN1203 | pRN753 | pRN593 | | | pRN977 | |
| RN1204 | pRN753 | | pRN594 | pRN957 | | |
| RN1205 | pRN753 | | pRN594 | | pRN977 | |
| RN1206 | pRN753 | pRN593 | pRN594 | pRN957 | | |
| RN1207 | pRN753 | pRN593 | pRN594 | | pRN977 | |

3. Anoxic Fermentations in Sterile Yeast Extract Peptone Medium with Constructed Strains in the Presence and Absence of Glycerol and or Acetic Acid The proof of principle of concomitant reduction of acetic acid and oxidation of glycerol was obtained by using a medium containing 1% yeast extract and 1% peptone. Experiments were run in chemostat culture (1 liter working volume) at D=0.05 $h^{-1}$ and the pH was kept at 5.5 by automatic addition of either KOH or $H_2SO_4$. Glucose (50 g/l) and xylose (50 g/l) were added as carbon and energy source to the yeast extract peptone medium. For these experiments demonstrating the proof of principle, no arabinose was included. Where relevant, acetic acid was added to the yeast extract peptone medium at 4 g/l and glycerol at 10 g/l. The temperature was kept at 32° C.

Precultures of strains are prepared by inoculating a frozen glycerol stock culture of the yeast in an YP (Yeast extract at 1% w/v and Peptone at 1% w/v) medium with addition of each of the sugars glucose and xylose (each at 1% w/v) at 32° C. and pH 5.5. After 24 h incubation under oxic conditions in shake flasks, 50 ml of this culture is used to inoculate the chemostat cultures.

At steady state of the fermentations (5 volume changes), a sample was taken for analysis of sugar (glucose and xylose) consumption, consumption of acetic acid, and metabolite (ethanol and glycerol). Ethanol, glycerol and acetic acid concentrations are monitored by HPLC analysis. To determine the sugar consumption, glucose and xylose are determined by HPAEC (Dionex) analysis.

Strain RN1151 is not able to reach a steady state situation in the medium containing 4 g/l acetic acid either in the presence or absence of glycerol. If no acetic acid is added to the medium, the organism at steady state consumed all glucose and xylose (less than 1 g/l remaining) No glycerol was consumed, but instead it was produced.

Strains RN1200 and RN1201 are similarly tested on media with acetic acid and either with or without glycerol added. These strains perform distinctly different from strain RN1151. In the glycerol-containing medium the sugars glucose and xylose are consumed almost to completion (less than 1 g/l remaining) Acetic acid levels decreases to 0.5 g/l and the concentrations of glycerol at the end of the fermentation is 3 g/l in all three instances. The amounts of ethanol produced by strain RN1200 and RN1201 ranged between 43 and 47 g/l in various experiments. In the medium not containing glycerol, but containing 4 g/l acetic acid, no stable steady state was obtained. The strains cannot grow under these conditions. From these results we conclude that expression of the *E. coli* gldA and adhE genes in combination with upregulation of DAK1 or expression of *C. freundii* dhaK, has a profound effect on the performance of the strains. In the presence of glycerol, they are able to consume glycerol and acetic acid, Strains RN1202 to RN1207 are similar to strains RN1200 and RN1201 except for the fact that GPD1 and/or GPD2 genes have been deleted. In the medium containing 4 g/l acetic acid, the sugars glucose and xylose are consumed almost to completion (less than 1 g/l remaining) if glycerol is added to the medium as is the case for strains RN1200 and RN1201. If no glycerol is added, no steady state is obtained.

4. Anoxic Fermentations with the Constructed Strains in Acetic Acid Comprising Lignocellulosic Hydrolysates in the Presence or Absence of Glycerol The corn fiber hydrolysate contains: glucose (38 g/l), xylose (28 g/l), arabinose (12 g/l) and acetic acid (4 g/l). It had been prepared by treating corn fibers at 160 C and at pH 3.0 during 20 minutes, followed by enzymatic hydrolysis by cellulases and hemicellulases. Acetic acid was added to this hydrolysate resulting in a total concentration of acetic acid in the hydrolysate of 10 g/l. The pH of this hydrolysate enriched in acetic acid was restored to pH=4.5 by KOH addition. Yeast extract was added to this hydrolysate to reach a final concentration of 5 g/l. In all subsequent experiments, this enriched hydrolysate was employed. The pH during fermentations was kept at 6.5 by automatic addition of either KOH or $H_2SO_4$.

Precultures of strains are prepared by inoculating a frozen glycerol stock culture of the yeast in an YP (Yeast extract at 1% w/v and Peptone at 1% w/v) medium with addition of each of the sugars glucose, xylose and arabinose (each at 1% w/v) at 32° C. and pH 5.5. After 24 h incubation under oxic conditions in shake flasks, 50 ml of this culture is used to inoculate the fermenter cultures. Fermentations are performed in a fed-batch fermentation setup. Hydrolysate (either with or without glycerol added at 50 g/l) is pumped into the fermenter. If no glycerol was added, then 40 ml of water was added. During the first 6 hours, the flow rate for hydrolysate is set at a rate of 5 ml per hour. During the next 6 hours, the flow rate is set at 10 ml per hour. Subsequently, for another 43 hours, the flow rate is set at 20 ml per hour. The total volume at the end of the fermentation reaches 1000 ml. These anoxic fed-batch fermentations are performed at about pH=4.5 with gentle stirring at 100 rpm. The temperature during the fermentations is set at 32° C. To minimize infection, the hydrolysates are heated for 10 min at 105° C. prior to fermentations and the antibiotic kanamycine with at final concentration of 50 μg/ml is added.

At the end of the fermentations after 55 h, a sample was taken for analysis of sugar (glucose, xylose and arabinose) consumption, consumption of acetic acid, and metabolite (ethanol and glycerol). Ethanol, glycerol and acetic acid concentrations over time are monitored by HPLC analysis. To determine the sugar consumption, glucose, xylose, and arabinose are determined by HPAEC (Dionex) analysis.

Strain RN1151 (=RN1041 complemented with HIS3) is tested on hydrolysate either with or without glycerol added. In both instances, the concentration of glucose at the end of the fermentation run (55 h) is 35 g/l whereas xylose and arabinose remain at their initial concentrations of 28 and 12 g/l, respectively. The amounts of ethanol produced are 2 g/l and acetic acid is present at 9.5 g/l. No glycerol consumption is detected in the glycerol-containing hydrolysate. The fermentation of the sugars halts during the course of the fed-batch operation because of increasing levels of acetic acid. Initially, no acetic acid is present in the fermenter, but while pumping the hydrolysate that contained toxic levels of acetic acid, the concentration quickly reaches toxic levels.

Strains RN1200 and RN1201 are similarly tested on hydrolysate either with or without glycerol added. These strains perform distinctly different from strain RN1151. In the glycerol-containing hydrolysate, the sugars glucose, xylose and arabinose are consumed to completion. Acetic acid levels decreases to 2 g/l and the concentrations of glycerol at the end of the fermentation is 29.5 g/l in all three instances. The amounts of ethanol produced by strains RN1200 and RN1201 are 51.7, and 52.2 g/l, respectively. In the hydrolysate that did not contain glycerol, considerably less sugar is consumed. Xylose and arabinose levels are unchanged at 28 and 12 g/l, respectively. Glucose is consumed but to a limited extent only. At the end of the fermentation, the remaining concentration is 32 g/l in all three instances with ethanol reaching a concentration of 3 g/l. The concentration of acetic acid drops to 9.1 g/l at the end of the fermentation whereas some glycerol is produced (less than 0.5 g/l). From these results we conclude that expression of the *E. coli* gldA and adhE genes in combination with upregulation of DAK1 or expression of *C. freundii* dhaK, has a profound effect on the performance of the strains. In the presence of glycerol, they are able to consume glycerol and acetic acid, and produce additional ethanol (as compared to strain RN1151). In the absence of glycerol, the strains consume some acetic acid. But during the fermentation, the acetic acid level rises to toxic levels.

Strains RN1202 to RN1207 are similar to strains RN1200 and RN1201 except for the fact that GPD1 and/or GPD2 genes have been deleted. In the glycerol-containing hydrolysate, the sugars glucose, xylose and arabinose are consumed to completion as was the case for strain RN1200. Acetic acid levels similarly decrease to approximately 2 g/l and the concentrations of glycerol at the end of the fermentation is 28 g/l in these three instances. The amounts of ethanol produced for strains RN1202, RN1203, RN1204, RN1205, RN1206 and RN1207 are 51.6, 52.9, 52.1, 52.5, 53.1 and 52.3 g/l, respectively. In the hydrolysate that not containing glycerol, considerably less sugar is consumed. Xylose and arabinose levels are unchanged at 28 and 12 g/l, respectively. Glucose is consumed but to a limited extent only. At the end of the fermentation, the remaining concentration in the non-glycerol hydrolysate for glucose is 31 g/l in all three instances with ethanol reaching a concentration of 3 g/l. The concentration of acetic acid drops to 9.1 g/l at the end of the fermentation whereas some glycerol is produced (less than 0.5 g/l). From these results we conclude that deleting GPD1 and/or GPD2 genes along with the other modifications in RN1202, RN1203, RN1204, RN1205, RN1206 and RN1207 result in strains that can perform the desired reactions.

Materials and Methods for Examples 5-8

General Molecular Biology Techniques

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Media

The media used in the experiments was either YEP-medium (10 g/l yeast extract, 20 g/l peptone) or solid YNB-medium (6.7 g/l yeast nitrogen base, 15 g/l agar), supplemented with sugars as indicated in the examples. For solid YEP medium, 15 g/l agar was added to the liquid medium prior to sterilization.

In the AFM experiments, Mineral Medium was used. The composition of Mineral Medium has been described by Verduyn et al. (Yeast (1992), Volume 8, 501-517) and was supplemented with 2,325 g/l urea and sugars as indicated in the examples.

Transformation of Yeast Cells

Yeast transformation was done according to the method described by Schiestl and Gietz (Current Genetics (1989), Volume 16, 339-346).

Colony PCR

Genomic DNA was extracted from single yeast colonies for PCR according to the method described by LÕoke et al. (BioTechniques (2011), Volume 50, 325-328).

AFM Procedure

The Alcohol Fermentation Monitor (AFM; Halotec, Veenendaal, the Netherlands) is a robust and user-friendly laboratory parallel bioreactor that allows for accurate comparisons of carbon conversion rates and yields for six simultaneous anaerobic fermentations.

The starting culture of the AFM experiment contained 50 mg of yeast (dry weight). To determine this, a calibration curve was made of the RN1041 strain of biomass vs. OD700. This calibration curve was used in the experiment to determine the volume of cell culture needed for 50 mg of yeast (dry weight).

Prior to the start of the AFM experiment, precultures were grown as indicated in the examples. For each strain the $OD_{700}$ was measured and 50 mg of yeast (dry weight) was inoculated in 400 ml Mineral Medium (Verduyn et al. (Yeast (1992), Volume 8, 501-517), supplemented with 2,325 g/l urea and sugars as indicated in the examples.

Glyceroldehydrogenase Activity Assay

The method for the determination of the glyceroldehydrogenase activity assay was adopted from Lin and Magasanik (1960) J Biol Chem. 235:1820-1823.

TABLE 5

| Assay conditions | |
|---|---|
| 1.0M Carbonate/bicarbonate buffer pH 10 | 800 μl |
| 1.0M ammoniumsulfate | 33 μl |
| 0.1M NAD+ | 33 μl |
| Cell Free Extract | 5 μl |

Cell free extract was prepared by harvesting cells by centrifugation. Cells were harvested in the exponential phase. The cell pellet was washed once with 1 M carbonate/bicarbonate buffer (pH10) and a cell free extract was prepared in the same by the addition of glass beads and vortexing at maximum speed for 1 minute intervals until the cells were disrupted. The latter was checked microscopically.

Shake Flask Experiments

Anaerobic shake flask experiments were performed as indicated in the examples. Typical experiments use 100 ml Erlenmeyer flasks with 25 ml of medium. In order to ensure anaerobic conditions, the flask was closed with a waterlock.

For each time point, a separate shake flask was inoculated, thereby omitting aeration during sampling.

Strains

The parent strain used in the experiments described in examples 5 through 8 is RN1041.

RN1041 has been described in WO 2012067510. This strain has the following genotype:

MAT a, ura3-52, leu2-112, his3::loxP, gre3::loxP, loxP-pTPI1::TAL1, loxP-pTPI1::RKI1, loxP-pTPI1-TKL1, loxP-pTPI1-RPE1, delta::pADH1-XKS1-tCYC1-LEU2, delta::URA3-pTPI1-xylA-tCYC1

MAT a=mating type a ura3-52, leu2-112, HIS3::loxP mutations in the URA3, LEU2 and HIS3 genes respectively. The ura3-52 mutation is complemented by the URA3 gene on the xylA overexpression construct; the leu2-112 mutation is complemented by the LEU2 gene on the XKS1 overexpression construct. The deletion of the HIS3-gene causes a histidine auxotrophy. For this reason, RN1041 needs histidine in the medium for growth.

gre3::loxP is a deletion of the GRE3 gene, encoding aldose reductase. The loxP site is left behind in the genome after marker removal.

loxP-pTPI1 designates the overexpression of genes of, in the experiments described herein, the non-oxidative pentose phosphate pathway by replacement of the native promoter by the promoter of the TPI1 gene. The loxP site upstream of the strong, constitutive TPI1 promoter remains in the genome after marker removal (Kuyper et al, FEMS Yeast Research 5 (2005) 925-934).

delta:: means chromosomal integration of the construct after recombination on the long terminal repeats of the Ty1 retrotransposon.

Example 5

Construction of Strains

The following strains were constructed:

TABLE 6

| strains constructed | |
|---|---|
| RN1041 | Parent strain (see above) |
| RN1067 | RN1041 gpd1::hphMX |
| RN1068 | RN1041 gpd2::natMX |
| RN1069 | RN1041 gpd1::hphMX gpd2::natMX |
| RN1186 | RN1041 + pRN977 |
| RN1187 | RN1067 + pRN977 |
| RN1188 | RN1068 + pRN977 |
| RN1189 | RN1069 + pRN977 |

The deletion of the GPD1-gene (gpd1) and/or the GPD2-gene (gpd2) was brought about as described in Example 2.

Strains RN1041, RN1067, RN1068 and RN1069 were transformed with plasmid pRN977. This plasmid contains the following features: the HIS3-gene for selection of transformants, the 2μ origin of replication, the ampicillin resistance marker for selection in *E. coli*, the adhE-gene from *E. coli* under control of the PGK1-promoter and the ADH1-terminator, the DAK1-gene from *S. cerevisiae* under control of the TPI1-promoter and the PGI1-terminator and the *E. coli* gldA-gene, under control of the ACT1-promoter and CYC1-terminator. All promoters and terminators are from *S. cerevisiae*. The sequence of plasmid pRN977 is set out in SEQ ID NO: 39.

After transformation of strains RN1041, RN1067, RN1068 and RN1069, single colony isolates were subjected to colony PCR analysis, in order to check the presence of plasmid pRN977. A representative colony of each transformation was selected for further experimentation. These selected strains are designated RN1186, RN1187, RN1188 and RN1189.

Similarly, transformants were generated with the following specifications:

TABLE 7

| transformants | |
|---|---|
| RN1190 | RN1041 + pRN957 |
| RN1191 | RN1067 + pRN957 |
| RN1192 | RN1068 + pRN957 |
| RN1193 | RN1069 + pRN957 |

Plasmid pRN957 is similar to pRN977; however, the DAK1-gene from *S. cerevisiae* has been replaced by the dhaK-gene from *Citrobacter freundii*. The sequence of this plasmid, pRN957, is set out in SEQ ID NO: 37.

As a control strain, strain RN1041 was transformed with plasmid pRN595 (RN1041+pRN595). This plasmid, pRN595, is similar to pRN977; however, it lacks the gldA and DAK1 genes. The sequence of plasmid pRN595 is set out in SEQ ID NO: 30.

Example 6

Shake Flask Experiments

The performance of the constructed strains was tested in an anaerobic shake flask experiment. To this end, cells were pregrown in Mineral Medium (Verduyn) supplemented with glucose as carbon source. The cultures were incubated overnight in a rotary shaker at 280 rpm and 30° C.

An aliquot of the cells was taken from the overnight cultures for inoculation of the anaerobic cultures. The amount of cells was such, that the anaerobic culture had an initial optical density at 600 nm of approximately 0.1.

The carbon composition of the Mineral Medium: 2.5% glucose, 2.5% xylose, 1% glycerol and 2 g/l HAc. The pH was adjusted to pH 4.5. The shake flasks were closed with a waterlock in order to ensure anaerobic conditions. For each time point, a separate flask was inoculated.

The results of net glycerol increase or decrease, after 94 hours of fermentation, and the HAc consumption, are indicated in the table below.

TABLE 8

Glycerol and HAc consumption, and ethanol production values per strain

| Strain | Net Glycerol Increase (+) or Decrease (−) (in grams/liter) | HAc consumption (in grams/liter) | Ethanol titer (in grams per liter) |
|---|---|---|---|
| RN1041 | +1.47 | 0.24 | 23.28 |
| RN1186 | −1.20 | 0.99 | 25.32 |
| RN1187 | −1.52 | 0.99 | 23.76 |
| RN1188 | −0.80 | 0.97 | 25.01 |
| RN1189 | −0.86 | 0.89 | 24.85 |
| RN1190 | −0.47 | 0.71 | 24.38 |
| RN1191 | −0.80 | 0.93 | 24.77 |
| RN1192 | +0.93 | 0.29 | 23.60 |
| RN1193 | −0.84 | 0.92 | 24.93 |

The strain indicated in table 8 as RN1041 was transformed with plasmid pRS323, a standard cloning vector containing the HIS3-gene and a 2μ origin of replication, thereby complementing the histidine auxotrophy.

The results show:

- RN1041 produces glycerol, which makes sense since both GPD1- and GPD2-genes are active and gldA and DAK1 are not overexpressed. Since adhE is not expressed in this strain, HAc consumption is low.
- Strains RN1186 through RN1189 show glycerol and HAc consumption, resulting in an increased ethanol titer as compared to RN1041.
- The experiments with the transformants RN1190, RN1191 and RN1193 show the same results, i.e. consumption of glycerol and acetate, however to a slightly lesser extent. Also here, the ethanol titer is higher as compared to RN1041. The result of strain RN1192 is an artefact, as later characterization showed that this strain had lost its plasmid pRN957.

Overexpression of either a homologous or heterologous dihydroxyacetone kinase, in combination with overexpression of gldA and adhE, results in a simultaneous consumption of acetate and glycerol under anaerobic conditions.

Example 7

AFM Experiments

The experiment described in Example 6 was repeated in a slightly different set-up, i.e. the AFM (Alcoholic Fermentation Monitor), which allows on-line carbondioxide determination, during the experiment.

The strains tested were RN1041, RN1041+pRN595, RN1186, RN1187, RN1188 and RN1189. The strain RN1041 was transformed with plasmid pRS323, a standard cloning vector containing the HIS3-gene and a 2μ origin of replication, thereby complementing the histidine auxotrophy.

The strains were pre-cultured overnight in Mineral Medium with 2% glucose as carbon source, in a rotary shaker at 280 rpm and 30° C.

The cells were harvested and an AFM experiment was started as described above.

Samples were taken at regular intervals and sugars, ethanol, glycerol and HAc were determined by HPLC.

Results are shown in the Table below.

TABLE 9

Glycerol and HAc consumption and ethanol production values per strain at time = 112 hours.

| Strain | Net glycerol increase (−) or decrease (+) (grams per litre) | HAc consumption (grams per litre) | Ethanol production (grams per litre) |
|---|---|---|---|
| RN1041 | +1.4 | 0.1 | 24.0 |
| RN1041+ pRN595 | +1.1 | 0.4 | 24.1 |
| RN1186 | −0.3 | 0.7 | 25.5 |
| RN1187 | −1.2 | 1.0 | 25.5 |
| RN1188 | −0.3 | 0.7 | 25.2 |
| RN1189 | −1.1 | 1.0 | 25.6 |

Figure 2:
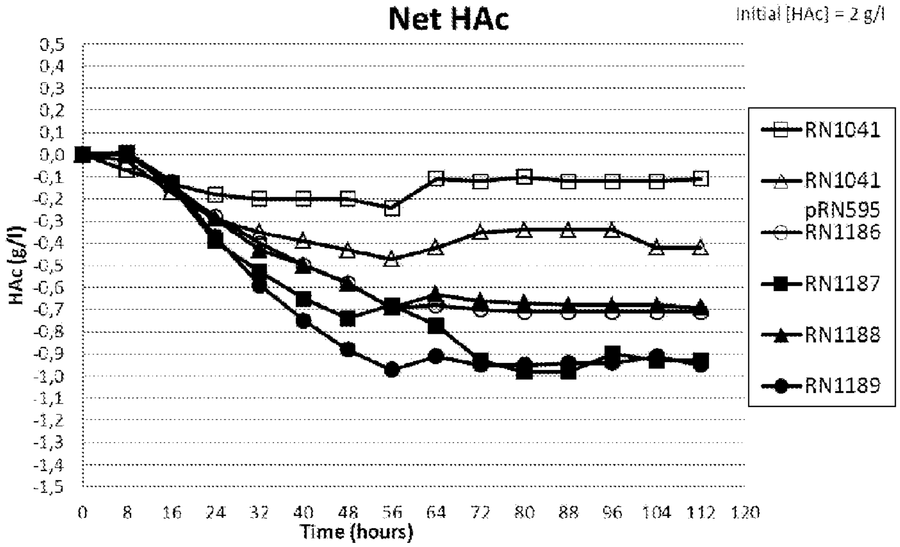
FIG. 2. The evolution of the net acetic acid levels (g/l) (i.e. production minus consumption) over time (hours) is shown for *S. cerevisiae* strains RN1041, RN1041+pRN595, RN1186, RN1187, RN1188 and RN1189.

The evolution of the glycerol and HAc levels in time are shown in FIGS. 1 and 2.

Strains RN1041 and RN1041+pRN595 are showing a net glycerol production. Strains RN1186 and RN1188 are initially showing glycerol production; however, after approximately 24 to 32 hours, glycerol consumption commenced and continued until in the end a net glycerol consumption was observed.

Strains RN1187 and RN1189 do not exhibit the initial glycerol production, as seen with RN1186 and RN1188. After 24 hours, glycerol consumption commences. The glycerol consumption is significantly higher in these strains as compared to RN1186 and RN1188. These results indicate that deletion of the GPD1-gene results in higher glycerol consumption than the deletion of the GPD2-gene.

Strain RN1041+pRN595 is showing a higher HAc consumption than the reference strain RN1041. RN1186 and RN1188 are exhibiting a higher HAc consumption than RN1041+pRN595. This result indicated that glycerol consumption enhanced HAc consumption. This effect is even stronger in strains RN1187 and RN1189.

Example 8

Glycerol Dehydrogenase Activity Assay

Cell free extracts (CFE) of strain RN1041 and RN1190 were prepared as described above. The glycerol dehydrogenase activity assay, adopted from the protocol of Lin and Magasanik (1960) J Biol Chem. 235:1820-1823, was performed. The results are shown in the Table below.

TABLE 10 glycerol dehydrogenase activity assay

| Sample | Cofactor | Increase in A340/min |
|---|---|---|
| RN1041 5 µl CFE | NAD+ | 0.00 |
| RN1190 5 µl CFE | NAD+ | 0.02 |
| RN1041 20 µl CFE | NAD+ | 0.00 |
| RN1190 20 µl CFE | NAD+ | 0.09 |

TABLE 10-continued glycerol dehydrogenase activity assay

| Sample | Cofactor | Increase in A340/min |
|---|---|---|
| RN1041 5 µl CFE | NADP+ | 0.00 |
| RN1190 5 µl CFE | NADP+ | 0.00 |
| RN1041 20 µl CFE | NADP+ | 0.00 |
| RN1190 20 µl CFE | NADP+ | 0.00 |

The strain indicated in table 10 as RN1041 was transformed with plasmid pRS323, a standard cloning vector containing the HIS3-gene and a 2µ origin of replication, thereby complementing the histidine auxotrophy.

These results indicate that: a) *E. coli* gldA, expressed in RN1190, is NAD+-dependent, and b) that increase in the amount of CFE resulted in a proportional increase of the conversion rate of NAD+, and hence of glycerol into dihydroxyacetone.

The invention claimed is:

1. A *Saccharomyces* cell which has been genetically modified to comprise:

(a) an exogenous gene encoding an enzyme with acetaldehyde dehydrogenase activity, that confers on the cell the ability to convert acetic acid into ethanol; and (b) a bacterial gene encoding an enzyme with $NAD^+$-linked glycerol dehydrogenase activity (EC 1.1.1.6), wherein the *Saccharomyces* cell does not comprise a genetic modification that reduces specific $NAD^+$-dependent formate dehydrogenase activity in the cell, wherein the exogenous gene encoding the enzyme with acetaldehyde dehydrogenase activity comprises a nucleotide sequence encoding the amino acid sequence of:

(i) SEQ ID NO:1, and/or (ii) SEQ ID NO:3, and/or (iii) SEQ ID NO:5; and/or a variant thereof, wherein the variant of (i), (ii), and/or (iii) is an enzyme in Tables 1, 2, and 3, respectively is 85% identical to SEQ ID NO:1, and/or SEQ ID NO:2, and/or (iii) SEQ ID NO:5, and wherein the bacterial gene encoding the enzyme with $NAD^+$-linked glycerol dehydrogenase activity comprises a nucleotide sequence encoding an amino acid sequence with at least 90% amino acid sequence identity to SEQ ID NO:7.

2. The *Saccharomyces* cell according to claim 1, wherein the cell further comprises a genetic modification that reduces specific $NAD^+$-dependent glycerol 3-phosphate dehydrogenase activity in the cell.

3. The *Saccharomyces* cell according to claim 2, wherein the genetic modification that reduces specific $NAD^+$-dependent glycerol 3-phosphate dehydrogenase activity in the cell is one or more genetic modifications that reduce the expression of an endogenous $NAD_+$-dependent glycerol 3-phosphate dehydrogenase and/or inactivates a gene encoding an endogenous $NAD_+$-dependent glycerol 3-phosphate dehydrogenase.

4. The *Saccharomyces* cell according to claim 3, wherein the NAD+-dependent glycerol 3-phosphate dehydrogenase is at least 90% identical to SEQ ID NO: 15 or 16.

5. A process for producing ethanol using the *Saccharomyces* cell of claim 1, comprising the step of fermenting a medium with a *Saccharomyces* cell, wherein the *Saccharomyces* cell has been genetically modified to comprise (a) an exogenous gene encoding an enzyme with acetaldehyde dehydrogenase activity, that confers on the cell the ability to convert acetic acid into ethanol, and (b) a bacterial gene encoding an enzyme with $NAD^+$-linked glycerol dehydrogenase activity (EC 1.1.1.6), wherein the *Saccharomyces* cell does not comprise a genetic modification that reduces specific $NAD^+$-dependent formate dehydrogenase activity in the cell, wherein the exogenous gene encoding the enzyme with acetaldehyde dehydrogenase activity comprises a nucleotide sequence encoding the amino acid sequence of:

(i) SEQ ID NO:1, and/or
(ii) SEQ ID NO:2, and/or
(iii) SEQ ID NO:5;
and/or a variant thereof,
wherein the variant of (i), (ii), and/or (iii) is an enzyme in Tables 1, 2, and 3, respectively is 85% identical to SEQ ID NO:1, and/or SEQ ID NO:2, and/or (iii) SEQ ID NO:5, and
wherein the bacterial gene encoding the enzyme with NAD+-linked glycerol dehydrogenase activity comprises a nucleotide sequence encoding an amino acid sequence with at least 90% amino acid sequence identity to SEQ ID NO:7; and (i) a source of at least one of hexose and a pentose; (ii) a source of acetic acid; and (iii) a source of glycerol,
the *Saccharomyces* cell ferments acetic acid, glycerol and at least one of the hexose and the pentose to ethanol, and the process optionally comprises a step of recovering the ethanol.

6. The process according to claim 5, wherein the *Saccharomyces* cell further comprises a genetic modification that increases the specific activity of dihydroxyacetone kinase, wherein the modification is overexpression of a nucleotide sequence encoding a dihydroxyacetone kinase, wherein the nucleotide sequence encoding the dihydroxyacetone kinase comprises a nucleotide sequence encoding an amino acid sequence with at least 90% amino acid sequence identity to SEQ ID NO:8, or SEQ ID NO:9, or SEQ ID NO:25.

7. The process according to claim 5, wherein the *Saccharomyces* cell further comprises a genetic modification that increases at least one of:

(i) specific acetyl-CoA synthetase activity; and
(ii) transport of glycerol into the cell.

8. The process according to claim 7, wherein (i) the nucleotide sequence encoding the acetyl-CoA synthetase encodes
(A) an acetyl-CoA synthetase with a higher maximum rate than acetyl-CoA synthetase encoded by *S. cerevisiae* ACS1 gene, or
(B) an acetyl-CoA synthetase with a higher affinity for acetate than the affinity of acetyl-CoA synthetase encoded by *S. cerevisiae* ACS2 gene, and
(ii) the genetic modification that increases transport of glycerol into the cell's overexpression of a nucleotide sequence encoding
(A) a glycerol uptake protein and/or
(B) a glycerol channel.

9. The process according to claim 7, wherein the genetic modification that increases the specific acetyl-CoA synthetase activity does so under anaerobic conditions.

10. The process according to claim 5, wherein the *Saccharomyces* cell comprises at least one of:

(i) a functional exogenous xylose isomerase gene, that confers on the cell the ability to isomerise xylose into xylulose; and
(ii) functional exogenous genes encoding an L-arabinose isomerase, an L-ribulokinase and an L-ribulose-5-phosphate 4-epimerase, which genes together confer on the cell the ability to convert L-arabinose D-xylulose 5-phosphate.

11. The process according to claim 5, wherein the *Saccharomyces* cell is a member of a species selected from the group consisting of *S. cerevisiae, S. exiguus*, and *S. bayanus*.

12. The process according to claim 5, wherein the medium contains or is fed with a lignocellulosic hydrolysate.

13. The process according to claim 5, wherein the *Saccharomyces* cell ferments under anaerobic conditions.

14. The process according to claim 7, wherein specific acetyl-CoA synthetase activity is modified by overexpression of a nucleotide sequence encoding an acetyl-CoA synthetase enzyme.

15. The process according to claim 8, wherein (A) the nucleotide sequence encoding the glycerol uptake protein comprises a nucleotide sequence encoding an amino acid sequence with at least 90% amino acid sequence identity to at least one of SEQ ID NO:10 and SEQ ID NO:11, and
(B) the nucleotide sequence encoding the glycerol channel comprises a nucleotide sequence encoding an amino acid sequence with at least 90% amino acid sequence identity to the amino acid sequence between residues 250 and 530 of SEQ ID NO:12.

16. The process according to claim 10, wherein the *Saccharomyces* cell comprises at least one additional genetic modification that results in a characteristic selected from the group consisting of:

(a) increased xylulose kinase specific activity;
(b) increased flux of the pentose phosphate pathway;
(c) reduced nonspecific aldose reductase specific activity;
(d) increased transport of xylose and/or arabinose into the host cell;
(e) decreased sensitivity to catabolite repression;
(f) increased tolerance to ethanol, osmolarity or organic acids; and
(g) reduced production of by-products.

* * * * *

UNITED STATES PATENT AND TRADEMARK OFFICE

CERTIFICATE OF CORRECTION

PATENT NO. : 9,988,649 B2
APPLICATION NO. : 14/361782
DATED : June 5, 2018
INVENTOR(S) : De Bont et al.

It is certified that error appears in the above-identified patent and that said Letters Patent is hereby corrected as shown below:

In the Claims

In Column 191, Line 61, in Claim 1, delete “SEQ ID NO:2” and insert --SEQ ID NO:3--, therefor.

In Column 193, Line 7, in Claim 5, delete “SEQ ID NO:2” and insert --SEQ ID NO:3--, therefor.

In Column 193, Line 12, in Claim 5, delete “SEQ ID NO:2” and insert --SEQ ID NO:3--, therefor.

Signed and Sealed this
Nineteenth Day of May, 2020

Andrei Iancu
*Director of the United States Patent and Trademark Office*